United States Patent [19]
Khoo et al.

[11] Patent Number: 5,994,295
[45] Date of Patent: Nov. 30, 1999

[54] THERAPEUTIC SYSTEM FOR DIETARY HEALTH MANAGEMENT

[75] Inventors: Chor San Heng Khoo, Mt. Laurel, N.J.; R. David MacNair, King of Prussia, Pa.

[73] Assignee: Campbell Soup Company, Camden, N.J.

[21] Appl. No.: 08/927,076

[22] Filed: Sep. 10, 1997

Related U.S. Application Data

[63] Continuation of application No. 08/466,893, Jun. 6, 1995, abandoned.

[51] Int. Cl.⁶ .......................... A61K 38/00; A61K 31/70; A61K 31/20; A61K 31/235
[52] U.S. Cl. ................. 514/2; 514/23; 514/558; 514/560; 514/533
[58] Field of Search ............... 514/2, 23, 558, 514/560, 533

[56] References Cited

U.S. PATENT DOCUMENTS

| | | |
|---|---|---|
| 3,852,497 | 12/1974 | Skelcey et al. |
| 3,950,547 | 4/1976 | Lemar, III et al. |
| 4,042,687 | 8/1977 | Gans et al. |
| 4,152,462 | 5/1979 | Hayward et al. |
| 4,192,860 | 3/1980 | Griffiths . |
| 4,267,199 | 5/1981 | Koshida et al. |
| 4,310,316 | 1/1982 | Thomann . |
| 4,544,550 | 10/1985 | Rodolfo . |
| 4,606,555 | 8/1986 | Adams . |
| 4,650,218 | 3/1987 | Hawke . |
| 4,652,241 | 3/1987 | McCarty . |
| 4,673,578 | 6/1987 | Becker et al. |
| 4,689,019 | 8/1987 | Tilney . |
| 4,751,085 | 6/1988 | Gaull . |
| 4,777,045 | 10/1988 | Vanderveer et al. |
| 4,795,653 | 1/1989 | Bommarito . |
| 4,806,354 | 2/1989 | Green . |
| 4,806,368 | 2/1989 | Reddy . |
| 4,828,498 | 5/1989 | Tilney . |
| 4,832,603 | 5/1989 | Basil . |
| 4,877,627 | 10/1989 | Leitz et al. |
| 4,900,566 | 2/1990 | Howard . |
| 4,950,164 | 8/1990 | Lenno-Thompson et al. |
| 4,973,467 | 11/1990 | Sahley . |
| 4,976,622 | 12/1990 | Clark . |
| 4,979,901 | 12/1990 | Robertson et al. |
| 5,017,391 | 5/1991 | Anders et al. |
| 5,034,378 | 7/1991 | Cox . |
| 5,044,958 | 9/1991 | Robertson et al. |
| 5,082,678 | 1/1992 | Margolis . |
| 5,122,379 | 6/1992 | Ohta et al. |
| 5,164,384 | 11/1992 | Paul . |
| 5,171,570 | 12/1992 | Takemori et al. |
| 5,186,963 | 2/1993 | Howman . |
| 5,221,668 | 6/1993 | Henningfield et al. |
| 5,223,285 | 6/1993 | DeMichele et al. |
| 5,252,351 | 10/1993 | Cox et al. |
| 5,268,367 | 12/1993 | Miwa et al. |
| 5,299,356 | 4/1994 | Maxwell, III . |
| 5,308,627 | 5/1994 | Umbdenstock, Jr. |
| 5,326,569 | 7/1994 | Acosta et al. |
| 5,332,579 | 7/1994 | Umbdenstock . |
| 5,338,202 | 8/1994 | Saari . |
| 5,340,315 | 8/1994 | Kaye . |
| 5,454,721 | 10/1995 | Kuch . |

FOREIGN PATENT DOCUMENTS

| | | |
|---|---|---|
| 0259167 | 9/1988 | European Pat. Off. |
| 0567433 | 10/1993 | European Pat. Off. |
| 2176569 | 2/1973 | France . |
| 2583958 | 1/1987 | France . |
| 2629685 | 10/1989 | France . |
| 2447266 | 3/1974 | Germany . |
| 4201504 | 9/1993 | Germany . |
| 588975 | 9/1947 | United Kingdom . |
| 589031 | 10/1947 | United Kingdom . |
| 9104757 | 4/1991 | WIPO . |

OTHER PUBLICATIONS

Sally Squires, Eat Your Veggies, The Washington Post, Jan. 2, 1996, Health at 12–15 and 17.

Part II—Food and Drug Administration, U.S. Department of Health and Human Services, 60 Fed. Reg. 67163–67224 (Dec. 28, 1995).

National Cancer Institute, Action Guide for Healthy Eating, National Institutes of health, U.S. Department of Health and Human Services, NIH Publ. No. 95–3877 (May 1995).

Martha M. Hamilton, Leaner Snacks, Fatter Sales, Demand Grows for New Products, The Washington Post, Apr. 20, 1995, at B10, B12.

diet to go! (Ordering information; 3 pgs) (Apr. 1995).

diet to go! (Sample menus; 4 pgs) (Feb. 1995).

American Diabetes Association, Medical Management of Non–Insulin–Dependent (Type II) Diabetes, 1–99 (3rd ed. Jun. 1994).

Part II—Food and Drug Administration, U.S. Department of Health and Human Services, 59 Fed. Reg. 349–469 (Jan. 4, 1994).

(List continued on next page.)

Primary Examiner—William R. A. Jarvis
Attorney, Agent, or Firm—Baker & Botts, LLP

[57] ABSTRACT

A dietary health management system for administration to a patient having at least one diet-responsive condition such as hypertension, hyperlipidemia, cancer, diabetes, and combinations thereof. In particular, the system comprises a plurality of prepackaged meals which may provide dietary fiber in the range of about 20 to 30 grams; vitamins and minerals at about 100% USRDA; less than about 2400 mg of sodium; at least about 3500 mg of potassium; less than about 96 grams of simple sugars; protein, such about 15 to 20% of caloric intake is derived from protein; and fat, such that about 20 to 30% of caloric intake is derived from fat. Comsumption of a daily diet comprising a plurality of the individual meals supplies the patient with the desired total daily calorie intake, improved quality of life, and sufficient nutritional enhancement to facilitate the management of the diet-responsive condition.

52 Claims, 8 Drawing Sheets

OTHER PUBLICATIONS

D.D. Bradford, D.L. Huffman, W.R. Egbert, and W.R. Jones, Low–Fat Fresh Pork Sausage Patty Stability in Refrigerated Storage With Potassium Lactate, 58 Journal of Food Science, 488 (1993).

National Heart, Lung, and Blood Institute, Report of the Expert Panel on Population Strategies for Blood Cholesterol Reduction—Executive Summary, National Institutes of Health, U.S. Department of Health and Human Services, NIH Publ. No. 93–3047 (Mar. 1993).

J.R. Unda, R.A. Mollins, and H.W. Walker, Clostridium sporogenes and Listeria monocytogenes: Survival and Inhibition in Microwave–ready Beef Roasts Containing Selected Antimicrobials, 56 Journal of Food Science 198 (1991).

Part II—Food Safety and Inspection Service, U.S. Department of Agriculture, and Part III & IV, Food and Drug Administration, Department of health and Human Services 56 Fed. Reg. 60301–60891 (Nov. 27, 1991).

Laboratories Division, American Cyanamid Company, Dynatrim™ (Instruction Sheet) (1990).

Leora A. Shelef and Qian Yang, Growth Suppression of Listeria monocytogenes by Lactates in Broth, Chicken, and Beef, 54 Journal of Food Protection 283 (1990).

Johan M. Debevre,s The Effect of Sodium Lactate On the Shelf Life of Vacuum–Packed Coarse Liver Pâté,69 Fleischwirisch 223 (1989).

M.K. Fordyce–Baum, L.M. Langer, E. Mantero–Atienza, R.Crass, and R.S. Beach, Use of Expanded–Whole–Wheat Product int he Reduction of Body Weight and Serum Lipids in Obese Females, 50 The American Journal of Clinical Nutrition 30–36 (1989).

Jean A. Pennington, Bowes & Church's Food Values of Portions Commonly Used, 269–277 (J.B. Lippincott Company 15th ed. 1989).

National Researchs Council, Recommended Dietary Allowances, 1–9 (Ch. 1) and 247–261 (Ch. 11) (National Academy Press 10th ed. 1989).

National Research Council, Diet and Health Implications for Reducing Chronic Disease Risk, 3–22 (Executive Summary) and 665–710 (Ch. 28) (National Academy Press 1989).

The American Dietetic Association, Exchange Lists For Meal Planning (American Diabetes Association, Inc., 1989).

Ruth H. Mathews, Pamela R. Pehrsson, and Mojgan Farhat–Sabet, Sugar Content of Selected Foods: Individual and Total Sugars (U.S. Department of Agriculture 1988).

The Nutrition Committee, American Heart Association, Dietary Guidelines for Healthy American Adults, 77 Circulation No. 3 (4 pgs) (Mar. 1988).

Barbara J. Rolls, Marion Hetherington, and Victoria J. Burley, The Specificity of Satiety: The Influence of Foods and Different Macronutrient Content on the Development of Satiety, 43 Physiology & Behavior 145 (1987).

U.S. Department of Health and Human Services, Public Health Service, and National Institutes of Health, Diet, Nutrition & Cancer Prevention: The Good News (National Cancer Institute 1986).

Labels for cans of Slim–Fast® and ultra Slim–Fast® (1991).

D.A. McCarron, et al., *Nutritional Management of Cardiovascular Risk Factors: A Randomized Clinical Trial,* Arch Intern Med, vol. 157, 169–177 (1997).

Joint National Committee on Detection, Evaluation, and Treatment of High Blood Pressure. The Fifth Report of the Joint National Committee on Detection, Evaluation, and Treatment of High Blood Pressure (JNC V), Arch Intern Med, vol. 153, 54–183 (1993).

Working Group on Management of Participants with Hypertension and High Blood Cholesterol, National Education Programs Working Group Report on the Management of Patients With Hypertension and High Blood Cholesterol, Ann Intern Med, vol. 114, 224–237 (1991).

DHHS (U.S. Department of Health and Human Services,) The Surgeon General's Report on Nutrition and Health, Government Printing Office, Washington D.C., Publication No. 88–50201, pp. 82–137 (1988).

R.M. Krauss et al., Dietary Guidelines for Healthy American Adults: A Statement for Health Professionals From the Nutrition Committee, American Heart Association, Circulation, vol. 94, 1795–1800 (Oct. 1, 1996).

American Diabetes Association, Nutrition Recommendations and Principles for People with Diabetes Mellitus, Diabetes Care, vol. 19, 516–519 (Jan. 1, 1996).

G.A. MacGregor, et al., Double–Blind Randomized Crossover Trial of Moderate Sodium Restriction in Essential Hypertension, The Lancet Ltd, 351–354 (1982).

J.M. Geleijnse, et al., Reduction in Blood Pressure With a Low Sodium, High Potassium, High Magnesium Salt in Older Subjects With Mild to Moderate Hypertension, BMJ, vol. 309, 436–440 (1994).

R.P. Mensink, et al., Effect of a Diet Enriched With Monounsaturated or Polyunsaturated Fatty Acids on Levels of Low–Density and High–Density Lipoprotein Cholesterol in the Healthy Women and Men, The New England Journal of Medicine, vol. 321, 436–441 (1989).

A. Garg, et al., Effects of Varying Carbohydrate Content of Diet in Patients with Non–Insulin–Dependent Diabetes Mellitus, JAMA, vol. 271, No. 18, 1421–1428 (1994).

R. Stamler, et al., Primary Prevention of Hypertension by Nutritional–Hygienic Means, JAMA, vol. 262, No. 13, 1801–1807 (1989).

The Trials of Hypertension Prevention Collaborative Research Group, The Effects of Nonpharmacologic Interventions on Blood Pressure of Persons With High Normal Levels: Results of the Trials of Hypertension Prevention, Phase I, JAMA, vol. 267, No. 9, 1213–1220 (1992).

P.D. Wood, et al., The Effects on Plasma Lipoproteins of a Prudent Weight–Reducing Diet, With or Without Exercise, in Overweight Men and Women, The New England Journal of Medicine, vol. 327, No. 7, 461–466 (1991).

G. Schuler, et al., Regular Physical Exercise and Low–Fat Diet: Effects on Progression of Coronary Artery Disease, Circulation, vol. 86, 1–11 (1992).

J. Dollahite, et al., Problems Encountered in Meeting the Recommended Dietary Allowances for Menus Designed According to the Dietary Guidelines for Americans, Journal of the American Dietetic Association, vol. 95, No. 3, 341–344, 347 (1995).

American Diabetes Association and American dietetic Association, Exchange Lists for Meal Planning, The American Diabetes Association, Inc., and The American Dietetic Association, Chicago, IL (1995).

S.H. Croog, et al., Hypertensive Black Men and Women: Quality of Life and Effects of Antihypertensive Medications, Arch Intern Med, vol. 150, 1733–1741 (1990).

M. Angell, et al., Clinical Research—What Should the Public Believe?, The New England Journal of Medicine, vol. 331, No. 31, 189–190 (1994).

G.M. Reaven, Insulin Resistance, Hyperinsulinemia, and Hypertriglyceridemia in the Etiology and Clinical Course of Hypertension, The American Journal of Medicine, vol. 90 (suppl 2A), 2A–7S–2A12S (1991).

O. Samuelsson, et al., The Role of Diabetes Mellitus and Hypertriglyceridaemia as Coronary Risk Factors in Treated Hypertension: 15 years of Follow–Up of Antihypertensive Treatment in Middle–Aged Men in the Primary Prevention Trial in Göteborg, Sweden, Journal of Internal Medicine, vol. 235, 217–227 (1994).

F.M. Sacks, et al., Rationale and Design of the Dietary Approaches to Stop Hypertension Trial (DASH): A Multi-center Controlled–Feeding Study of Dietary Patterns to Lower Blood Pressure, Ann Epidemiol, vol. 5, No. 2, 108–118 (1995).

R.W.F. Wilson, et al., Coronary Risk Prediction in Adults (The Framingham Heart Study), The American Journal of Cardiology, vol. 59, 91G–94G (1987).

Icy Containers, Packaging Digest (May 1995).

H. Shamoon, et al., The Effect of Intensive Treatment of Diabetes on the Development and Progression of Long–Term Complications in Insulin–Dependent Diabetes Mellitus, The New England Journal of Medicine, vol. 329, No. 14, 977–986 (1993).

The Diabetes Control and Complications Trial Research Group, Influence of Intensive Diabetes Treatment on Quality–of–Life Outcomes in the Diabetes Control and Complications Trial, Diabetes Care, vol. 19, No. 3 (Mar. 1996).

D.L. Sackett, et al., Compliance in Health Care: The Magnitude and Compliance of Noncompliance, The Johns Hopkins University Press (1989).

Subcommittee on the Tenth Edition of the RDSs Food and Nutrition Board, Commission on Life Sciences, National Research Council, Recommended Dietary Allowances 10th Edition, National Academy Press, 284–285 (1989).

The Chicago Dietetic Association and The South Suburban Dietetic Association, Manual of Clinical Dietetics, Fourth Edition, The American Dietetic Association, 17–18 (1992).

G.R. Warnick, et al., Dextran Sulfate–$Mg^{2+}$ Precipitation procedure for Quantitation of High–Density–Lipoprotein Cholesterol, Clinical Chemistry, vol. 28, No. 6 (1982).

W.T. Friedewald, et al., Estimation of the Concentration of Low–Density Lipoprotein Cholesterol in Plasma, Without Use of the Preparation Ultracentrifuge, Clinical Chemistry, vol. 18, No. 6 (1972).

C.T. Veit, et al., The Structure of Psychological Distress and Well–Begin in General Populations, Journal of Consulting and Clinical Psychology, vol. 51, No. 5, 730–742 (1983).

H.N. Ginsburg, New Directions in Dietary Studies and Heat Disease: The national Heart, Lung and Blood Institute Sponsored Multicenter Study of Diet Effects on Lipoproteins and Thrombogenic Activity, Nutrition and Biotechnology in Heart Disease and Cancer, vol. 369, 241–247 (1995).

C. Bae, et al., Plasma Lipid Response and Nutritional Adequacy in Hypercholesterolemic Subjects on the American Heart Association Step–One Diet, American Medical Association (1992).

National Heart, Lung, and Blood Institute, National Institutes of Health, and U.S. Department of Health and Human Services, National Cholesterol Education Program: Report of the Expert Panel on Population Strategies for Blood Cholesterol Reduction: Executive Summary, Arch Intern Med, vol. 151, 1071–1085 (1991).

J.E. Ware, Jr., et al., Conceptualization and Measurement of Health for Adults in the Health Insurance Study: vol. III, Mental Health, Rand Health Insurance Study (1979).

Edward D. Frohlich, M.D., et al., Recommendations for Human Blood Pressure Determination by Sphygmomanometers, AHA News, 502A–514A, 1989.

National Research Council, Implications for Reducing Chronic Disease Risk, Diet and Health, 1989.

Bundesverband der Pharmazeutischen Industrie e.V., Rote Liste 1987, (Items 61011–61049) 1987.

Vanessa O'Connell, How Campbell Saw a Breakthrough Menu Turn Into Leftovers, Wall Street Journal, A1, A12 (Oct. 6, 1998).

Specific Daily Dietary Allotments Differing Calorie Levels

| Kcal/day: | 1200–1399 | 1400–1599 | 1600–1799 | 1800–1999 | | 2000–2199 | | 2200–2399 | | 2400–2599 | |
|---|---|---|---|---|---|---|---|---|---|---|---|
| Profile Option | 1 | 1 | 1 | 1 | 2 | 1 | 2 | 1 | 2 | 1 | 2 |
| Kcal(actual): | 1241 | 1441 | 1535 | 1722 | 1826 | 1910 | 2014 | 2097 | 2117 | 2285 | 2305 |
| Kcal w/bonus: [a] | 1361 | 1561 | 1655 | 1842 | 1946 | 2030 | 2134 | 2217 | 2237 | 2405 | 2425 |
| Fat(g): | 26.2 | 29.7 | 30.7 | 32.7 | | 34.7 | | 36.7 | | 38.7 | |
| Fat(%):[b] 14–19 (mean=16.6%) | 19.0 | 18.5 | 18.0 | 17.1 | | 16.4 | | 15.8 | | 15.2 | |
| CHO(g): | 183.7 | 216.9 | 234.2 | 268.7 | | 303.2 | | 337.7 | | 372.2 | |
| CHO(%): 59–66 (mean=63.1%) | 59.2 | 60.2 | 61.0 | 62.4 | | 63.5 | | 64.4 | | 65.2 | |
| Protein(g): | 67.5 | 76.5 | 80.5 | 88.5 | | 96.5 | | 104.5 | | 112.5 | |
| Protein(%): 19–22 (mean=20.4%) | 21.7 | 21.2 | 21.0 | 20.6 | | 20.2 | | 19.9 | | 19.7 | |
| Sodium(mg) [e] | 1702 | 1770 | 1837 | 1972 | | 2107 | | 2242 | | 2377 | |
| Breakfast | 1 | 1 | 1 | 1 | 1 | 1 | 1 | 1 | 1 | 1 | 1 |
| Lunch | 1 | 1 | 1 | 1 | 1 | 1 | 1 | 1 | 1 | 1 | 1 |
| Dinner | 1 | 1 | 1 | 1 | 1 | 1 | 1 | 1 | 1 | 1 | 1 |
| Fruit/Veg/Diary | c | 1 | 1 | 1 | 1 | 1 | 1 | 1 | 1 | 1 | 1 |
| Snack Meal | 0 | d | 1A | 2A | 1A,1B[f] | 3A | 2A,2B | 4A | 1A,2B | 5A | 2A,2B |
| Bonus | 1 | 1 | 1 | 1 | 1 | 1 | 1 | 1 | 1 | 1 | 1 |

[a] Prescriptions include a daily selection from the "bonus" food list (mean caloric value of 120 kcal).
[b] Percentages are based on caloric level without bonus.
[c] Select 1 fruit and 1 vegetable serving or 1 dairy serving on alternate days.
[d] Select 1 snack meal A on alternate days
[e] Does not include bonus or fruit/veg/dairy serving in calculation.
[f] Snack B is the high-calorie snack meal.

FIG. 2

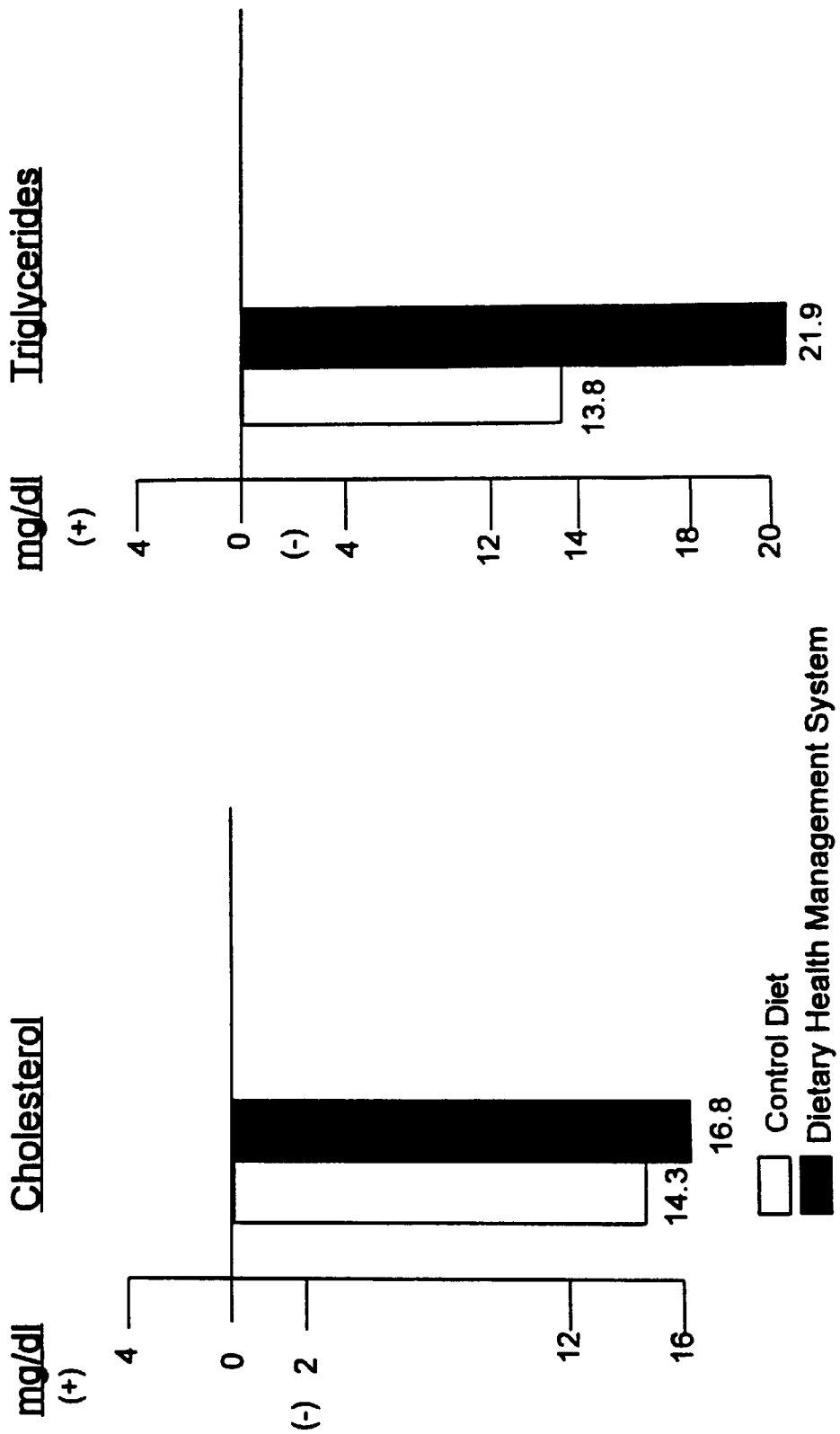

THERAPEUTIC SYSTEM FOR DIETARY HEALTH MANAGEMENT

This application is a continuation of application Ser. No. 08/466,893, filed Jun. 6, 1995, now abandoned.

BACKGROUND OF THE INVENTION

1. Field of the Invention

This invention relates generally to therapeutic systems and methods for dietary health management, i.e., the prevention, treatment, or reduction of risk factors associated with diet-responsive conditions, or a combination thereof. In particular, it relates to systems providing a choice of prepackaged, easy to prepare, and good tasting, therapeutic meals which are intended to improve the health and quality of life of patients utilizing the system. Further, it relates to the fortification of meals and food products for use with such a system. As confined by clinical trials, the systems and methods disclosed herein achieve improvements in quantifiable indicators of diet-responsive conditions, improved quality of life, and a high degree of compliance.

2. Description of the Related Art

People have become increasingly aware of the importance of a proper diet for health maintenance and disease prevention and treatment. Unfortunately, because numerous different and often conflicting dietary guidelines are presented in such complex manners, it is often very difficult for a person attempting to follow a diet for health and disease management (hereinafter a "patient") to understand and fully and effectively implement a healthy diet. For example, a diet which maximizes health and disease management concerns might control the intake of simple sugars, cholesterol, and different quantities and types of fat, as well as calories, while also attempting to optimize levels of macro- and micronutrients, e.g., protein, carbohydrates, and fat, and vitamins and minerals, and to provide adequate dietary fiber. As suggested above, however, the problem of planning and maintaining a healthful diet goes beyond the usual health concerns and exists with respect to special diet situations, including those associated with diet-responsive conditions, such as cardiovascular disease (hypertension and hyperlipidemia), diabetes and cancer.

Diet planning assistance available to patients has been of limited value and often fails to satisfy long term compliance. Much additional planning has been left in the hands of patients who usually lack sufficient knowledge in the field of nutrition to fully and properly implement an adequate diet plan as part of a system or method for health management. More specifically, prior approaches to the planning and maintenance of a patient's diet have supplied the patient with general food and beverage categories to be consumed or avoided: for example, meat, eggs, and fish; fruits and vegetables; breads and cereals; and dairy products. Such approaches generally fail to achieve their desired goal, however, because patients do not consume general food and beverage categories; instead, they consume complex meals composed of specific foods and beverages. Even within these broad categories, specific foods and beverages are so diverse that it is often difficult for patients to convert the broad categories into meals, i.e., to plan actual diets, while still maintaining adequate consumption of protein, carbohydrates, fat, sugars, cholesterol, fiber and other macro- and micronutrients meeting the dietary guidelines.

Previous approaches to health management have included various physical devices to assist the patient in counting macro- or micronutrients or otherwise planning and maintaining his or her diet. These have included manipulatable devices, as shown, for example, in U.S. Pat. Nos. 4,606,555 and 4,625,675; various coupon and label systems, as shown, for example, in U.S. Pat. Nos. 4,310,316, 4,652,241, and 4,689,019; and card menus identifying meal exchanges, as shown, for example, in U.S. Pat. No. 4,950,164. Nevertheless, these devices, coupons, labels, and the like do not solve the problems addressed above of assisting patients by providing a simple, daily plan for consuming convenient meals composed of appropriate foods and beverages which satisfy the complex goals of a healthy diet over a period of time.

One procedure for providing a diet which is highly specific as to recommended foods and beverages is simply to provide a single fixed list of meals for a given day, week, or other time period or to provide the actual meals described on such a list. However, a fixed list or daily menu has the disadvantage of being too rigid and monotonous and, therefore, generally unappealing to patients after a relatively short period of time. Moreover, even a single fixed list of meals for a given day requires that patients purchase the components of the listed meals and assemble or prepare those meals. Both of these steps are time consuming and depending on the meals listed may require some degree of skill in the assembly or preparation. If it is more inconvenient, i.e., costly, difficult, or time consuming, to comply with the dietary recommendations, the satisfaction and compliance with the diet will be low. Moreover, if these nutritional goals are not met, malnutrition may result.

Nutrient imbalance may lead to physiological effects in humans, such as compromising cellular functions, i.e., immunoresponse, and, therefore, may negatively impact a patient's quality of life. Researchers have shown that, in many cases, these problems may be treated by orthomolecular therapy, such as that discussed in U.S. Pat. No. 4,973,467. Orthomolecular therapy is the treatment of a condition in a patient by varying the concentration of nutrients normally present in humans. These nutrients may include micronutrients, such as vitamins, minerals, trace elements, hormones, amino acids, and enzymes. If the concentration of any of these substances in a patient's system is low, it may disturb biochemical homeostasis, which may result in increased patient anxiety and/or stress. Thus, such imbalances may adversely impact quality of life. Regulating the concentration of these substances in the body helps to attain and maintain improved quality of life and health.

Another condition often associated with improper diet and health management is excess weight. Excess weight is associated with an increased risk of several chronic disorders, including non-insulin dependent (or Type II) diabetes, hypertension, and cardiovascular disease, such as coronary heart disease (CHD) and atherosclerotic disease. These risks, however, appear to decline following a sustained reduction in weight. Nevertheless, neither large fluctuations in body weight nor extreme restrictions in food intake are desirable.

In the North American population and other westernized societies, body weight and body mass index are increasing in spite of a reduction in overall caloric intake in some populations. Additionally, physical activity is decreasing. These trends as well as the association of moderate, regular physical activity with reduced risks of heart disease have led to the recommendation that the U.S. population increase its physical activity level and that all healthy people maintain physical activity at a moderately active level, and moderate their dietary intake to maintain appropriate caloric intake and body weight.

Diet may also have an effect on hypertension. It is probable that hypertension susceptibility to salt (salt sensitivity) is genetically determined, but a reliable genetic marker for salt sensitivity has not yet been identified. Thus, individuals with hypertension, who are salt sensitive, are most likely to benefit from salt reduction. The American Heart Association (AHA) recommends consumption of no more than about 3000 mg of sodium per day. However, even in salt-sensitive patients, a sodium intake of less than about 3000 mg is unlikely to contribute to blood pressure elevation and may even lead to blood pressure reduction. There is some evidence to suggest that frequent consumption of salt-preserved or salt-pickled foods increases the risk of stomach cancer.

A large and convincing body of evidence from studies in humans and laboratory animals shows that diets low in saturated fatty acids (SFAs) and cholesterol are associated with lower risks and rates of cardiovascular diseases than diets that are high in fat and cholesterol. High-fat diets are also linked to a high incidence of some types of cancer (e.g., colon and breast cancer) and obesity. Thus, reducing total fat and SFA intake seems likely to lower the rates and variety of these diet-related chronic diseases.

Different types of fatty acids have different effects on health. SFAs and dietary cholesterol tend to increase serum, low density (LDL) and very low density (VLDL) lipoproteins, and cholesterol and, consequently, the risk of cardiovascular disease. The evidence linking high-fat diets, i.e., diets which provide greater than 40% calories from fat, to increased cancer risk may be less firmly established than that associating SFAs and dietary cholesterol to CHD. The weight of evidence indicates that high-fat diets, which are also high in saturated fats, are associated with a higher risk of some cancers, especially of the colon, prostate, and breast. Most studies with humans suggest that diets with high total fat or SFA content adversely affect cancer risk. Few studies in humans have yet examined the benefits of changing to low-fat diets; however, such evidence exists from experiments in animal trials. The combined evidence from human epidemiologic and laboratory animal studies suggests that reduction of total dietary fat is likely to reduce the risk of these cancers. Concern that an increase in polyunsaturated fatty acids (PUFAs) intake may increase risk of certain cancers derives primarily from studies of animals on very-high-PUFA diets. Given the absence of human diets naturally very high in total PUFAs and the lack of information about the long-term consequences of high PUFA intake, PUFA intake has not been increased above about 10%.

Another diet-responsive condition which may be helped by improved health management is non-insulin dependent diabetes. Generally, the bodies of patients suffering from non-insulin dependent diabetes produces insulin, but the insulin produced does not function properly. Insulin dependent diabetics do not produce any insulin and must receive injections of insulin to avoid ketoacidosis, i.e., the build-up of ketones in the blood stream. Some non-insulin dependent diabetics may control their diabetes simply by limiting the amount and types of foods and beverages that they consume and increasing their physical activity levels or losing weight. However, many must also take oral hypoglycemic agents or insulin in order to metabolize their glucose.

The America Diabetes Association (ADA) states that non-insulin dependent diabetics may use a combination of diet, exercise, and medication to lower plasma glucose and plasma lipid levels. Diet is important not only to control plasma glucose and lipid levels, but to maintain control over body weight. As noted above, obesity may be linked to the onset or progression of non-insulin dependent diabetes. Moreover, insulin functions better in persons near their appropriate body weight. Weight increases also may cause diabetes-related problems, such as hypertension or CHD. Therefore, an appropriate diet for diabetics generally is calculated to include management of caloric intake and body weight.

In addition, the ADA recommends a diet low in fat and sugars, especially simple sugars. This is important in order to keep plasma glucose and plasma lipid levels under control. A low-fat diet, which is also low in sodium, further may reduce the likelihood of related problems such as hypertension and CHD. Moreover, a diet which is low in fat, simple sugars, and sodium is also generally high in fiber and complex carbohydrates. Dietary fiber has been shown to reduce plasma glucose and plasma lipid levels. In addition, foods high in complex carbohydrates, e.g., grains, legumes, vegetables, and fruits, are also excellent sources of vitamins, minerals, and calories.

Observational epidemiological studies and clinical experiments also have generated a number of hypotheses about the role of dietary factors in the etiology of various types of cancer. As discussed in U.S. Pat. No. 4,777,045, epidemiologic studies have identified low intake of dietary fiber as one of the factors associated with an increased rate of cancer of the colon and rectum. The presence of fiber in the intestinal tract may decrease food transit time, which reduces contact time between potential carcinogens and the mucosa, and dilute the intestinal contents. Thus, the presence of fiber may reduce the interaction of procarcinogens with bacteria. Although there currently appears to be no definitive definition of the material which is generally referred to as "fiber," the term "dietary fiber" has been applied to the plant cell wall constituents that are not digested by the secretions of the human digestive tract. The National Cancer Institute (NCI) currently recommends that patients consume about 20 to 30 grams of dietary fiber daily. Excessive consumption of fiber, e.g., greater than about 35 grams daily, however, may cause adverse health management effects.

The NCI also suggests that diets rich in foods containing Vitamin C and Vitamin A from fruits and vegetables may also reduce the risk of cancer. Epidemiologic studies have shown that diets high in Vitamin A and Vitamin C are associated with lower risks of some kinds of cancers. Therefore, the NCI recommends consumption of a variety of fruits and vegetables, including fruit and vegetable juices that are high in Vitamin A and Vitamin C. Especially beneficial are cruciferous vegetables which are good sources of fiber, as well as vitamins and minerals.

It also is increasingly appreciated that hypertension, non-insulin dependent diabetes, and various dyslipidemias frequently coexist. Further, these conditions may share common pathophysiological features including insulin resistance, hyperinsulinemia, and abnormal sodium or calcium metabolism, or both. The association of each of these conditions with accelerated atherosclerotic disease has been termed Generalized Cardiovascular and Metabolic Disease (GCMD).

In an attempt to facilitate management of GCMD, complex therapeutic strategies for each of these conditions emphasize nutritional interventions as one of the primary strategies for treatment. Diet alone may be a first choice of treatment for a large number of patients with one or more of these conditions, and diet, alone or in combination with other lifestyle changes, e.g., increased physical activity and cessation of smoking, or with pharmacological agents. Included in the nutritional interventions generally are a dietary sodium restriction; calcium supplementation; reduced intake of simple sugars; and controlled intake of saturated fat and cholesterol coupled with increased intake of dietary fiber and PUFAs.

In practice, choosing the proper combinations of therapeutic meals that implement a health management system appropriate for GCMD is difficult. For many patients, this complexity in choosing meals is so difficult that compliance will be inadequate to achieve desired health improvement. Consequently, a simple to follow, comprehensive health management system designed specifically for individuals diagnosed with one or more cardiovascular or metabolic conditions, or both, is needed. Simplicity and comprehensiveness are both essential if adequate compliance is to be achieved.

Various health organizations have developed individual dietary guidelines aimed at interventions for specific conditions. While such interventions have the potential to greatly reduce health risks, unfortunately, they often are performed in isolation from each other. Thus, a nutritional health management system targeted at simultaneously achieving a desirable therapeutic balance of vitamin, mineral, fiber, carbohydrate, protein, and fat content has been lacking.

A successful health management system comprising healthy meals composed of specific foods and beverages includes a mechanism for providing sufficient variety and versatility to maintain the interest of patients for an extended, or even an indefinite, period of time. If a diet is tasty, simple to understand, and easy to follow and the meals are simply and quickly obtained and prepared, compliance with the diet also will be high. Taste and appearance also may be critical factors in attaining adequate compliance. If the patient does not enjoy consuming the meals included in the diet, he or she is less likely to remain on the diet.

Thus, a need exists for a system and method which provides to the patient highly specific, yet flexible, meal, i.e., food and beverage, information that will satisfy the majority of the complex health guidelines applicable to the patient. These guidelines include meeting recommended dietary levels for calories, fat, proteins, simple sugars, sodium, cholesterol, or macro- and micronutrients. Further, such systems and methods should be sufficiently flexible to permit day-to-day variation of their selected variety of foods and beverages within the system and should involve an exchange mechanism which may be easily and conveniently utilized by patients.

SUMMARY OF THE INVENTION

In light of the above described need, it is an object of the present invention to provide a dietary health management system which adequately supplies desired levels of macro- and micronutrients. It is also an object of this invention that such a system provide specific directions which may readily be followed by patients to achieve successful implementation while providing sufficient variety, taste, and versatility to achieve adequate compliance. Further, it is an object of this invention that the system provide prepackaged therapeutic meals which are readily obtainable and easily prepared by patients and which may be stored, i.e., frozen or shelf-stable, without loss of nutritional benefits. An advantage of such meals is that their preparation is simple and convenient to the patient. Thus, patients are more likely to achieve higher dietary satisfaction and compliance. It is a feature of this invention that sufficient levels of macro- and micronutrients are added, such that meals may be initially processed, packaged, stored, either frozen or non-frozen, for extended periods, and prepared, e.g., heated, rehydrated, or cooked, for consumption within a reasonable period from packaging, e.g., within a range of about three (3) to twelve (12) months and preferably, at least about nine (9) months, and still provide the desired level of macro- and micronutrients when consumed.

In addition, it is an object of the present invention to provide a method for dietary health management, i e., preventing or treating and reducing risk factors associated with diet-responsive conditions, such as: obesity; hyperlipidemia; non-insulin dependent diabetes; hypertension; and cancer, for example, colo-rectal cancer; by supplying a diet providing recommended dietary levels of macro- and micronutrients. In addition to treating such conditions, this method may assist in the reduction of the dosages and quantities of pharmaceuticals administered to patients suffering from these conditions. This method is convenient to enable ready compliance, while ensuring that nutritional needs are met.

With regard to the system and method described above, it is another object of the present invention to provide a prepackaged therapeutic meal which supplies a predetermined percentage of a Dietary Food Enhancement Agent (DFEA) containing the desired micronutrients to meet a patient's daily needs. A plurality of such meals may be used as part of the system or method described above. Because it is preferable to fortify different food products to different levels, it is desirable that the fortified meal be packaged, such that the various components remain separate during storage.

In another object, the present invention is to provide a DFEA containing desired amounts of micronutrients, such as vitamins and minerals, for use in fortifying therapeutic meals and particular meal components. Various combinations of macro- and micronutrients are desirable to address specific needs in treating and preventing diet-responsive conditions, as well as maintaining general good health. The addition of the DFEA may be used in connection with controlling levels of sodium, simple sugars, cholesterol, fat, carbohydrates, proteins and fatty acids.

In one embodiment, the invention provides a dietary health management system for administration to a patient having at least one diet-responsive condition. Such diet-responsive condition may include obesity, hypertension, hyperlipidemia, cancer, diabetes, and combinations thereof. The system may comprise a meal program containing a plurality of prepackaged individual meals. Each of these individual meals may contain a predetermined level of nutritional enhancement, whereby consumption of a diet comprising a plurality of the individual meals supplies the patient with the desired total daily calorie content, improved quality of life, and sufficient nutritional enhancement to facilitate management of the diet-responsive condition. Such a diet may be designed to provide a core calorie content, i.e., about 1200 to 1500 calories per day, and individual meals may be fortified, such that the total daily diet provides up to 100% of a DFEA daily portion. Therefore, the DFEA may be designed to meet 100% of the USRDA or NAS/NRC RDA.

The dietary health management system of the present invention preferably is intended to be supplemented with foods and beverages selected from the group consisting of dairy products, fruits, and vegetables. These supplemental foods and beverages add to the variety and versatility of the diet; and because they are selected by the patient, they are more likely to be satisfactory to a particular patient's taste. Further, diet adjustors, i.e., snack meals, may be used to increase the level of micronutrients consumed by the patient and/or to increase the diet's calorie content depending on the patient's daily needs.

In another embodiment, the invention provides a dietary health management planning and control system for providing nutritionally enhanced dietary management to a patient having at least one diet-responsive condition, as described above. The system may comprise a plurality of prepackaged individual meals. Each of these meals is included within a group and has a group identifying code corresponding to the type of meal. For example, the type of the meals may comprise breakfast, lunch, and dinner, and the group identifying code may be selected from the group consisting of alphabetic indicia, numeric indicia, color indicia, graphic indicia, and combinations thereof. Moreover, each of the meals also may include at least one category identifying code corresponding to a particular diet-responsive condition. This category identifying code also may be selected from the group consisting of alphabetic indicia, numeric indicia, color indicia, graphic indicia, and combinations thereof. Each of the individual meals contains a predetermined level of nutritional enhancement, whereby consumption of a daily diet comprising a plurality of the individual meals supplies the patient with a desired total daily calorie content, improved quality of life, and sufficient nutritional enhancement to facilitate management of the diet-responsive condition.

In still another embodiment, the invention provides a method for treating patients having a diet-responsive condition. The method may comprise the steps of identifying at least one quantifiable indicator of the condition and administering to the patient a daily diet. The diet may comprise a plurality of prepackaged individual meals. Each of the individual meals contains a predetermined level of nutritional enhancement, whereby consumption of the diet comprising a plurality of the individual meals supplies the patient with the desired total daily calorie content, improved quality of life, and sufficient nutritional enhancement to facilitate management of the diet-responsive condition. The method further may comprise the step of monitoring the previously identified at least one indicator of the diet-responsive condition.

In yet another embodiment, the invention provides a prepackaged therapeutic meal, such as a frozen or shelf-stable meal, for administration to a patient having at least one diet-responsive condition. The meal may comprise a plurality of separate meal components. At least one of the meal components contains a predetermined level of nutritional enhancement, whereby consumption of a diet comprising a plurality of the meals supplies the patient with the desired total daily calorie content, improved quality of life, and sufficient nutritional enhancement to facilitate management of the diet-responsive condition. Although the nutritional enhancement may be concentrated in a single meal component, it is preferable to nutritionally enhance a plurality of meal components. Further, because patients may consume meal components selectively, by enhancing a plurality of meal components, the likelihood that the patient will consume some, if not all, of the DFEA additions is increased.

In an additional embodiment, the invention provides a food product for administration to a patient having at least one diet-responsive condition. The product comprises a nutritionally enhanced meal component selected from the group consisting of meats, baked goods, i.e., rolls, muffins and breads; sauces, e.g., vegetable, pasta, and meat sauces; starch sources, i.e., whipped potatoes and rice; soups; cereals; desserts; and fruit or vegetable juice beverages. The meal component supplies dietary fiber in a range of up to about 10 grams (0.35 ounces); vitamins and minerals in a range of about 5 to 35% the U.S. Recommended Dietary Allowance (USRDA); protein, such that caloric intake of up to about 20% is derived from protein; and fat, such that caloric intake of up to about 30% is derived from fat.

In a further embodiment, the invention is a DFEA, for fortifying food products comprising predetermined amounts of vitamins and minerals. In particular, the DFEA may include combinations of essential vitamins and minerals selected from the group consisting of vitamins and minerals for which a recommended dietary allowance as determined by governmental or national health organizations, such as the National Academy of Sciences (NAS) or by the U.S. Food and Drug Administration (FDA) for USRDA, has been established. Such a DFEA may comprise varying amounts of the following vitamins and minerals: Vitamins A, $B_1$, $B_2$, $B_3$, $B_6$, $B_{12}$, C, D, E, and K, and Biotin, Calcium, Copper, Folic Acid, Iodine, Iron, Magnesium, Manganese, Pantothenic Acid, Phosphorus, and Zinc.

In still another embodiment of the invention is a compliance support package for improving the compliance of a patient with a dietary health management system, which provides a predetermined daily calorie content and level of nutritional enhancement. The compliance support package includes portion identification aids, in which portion sizes of meal components are identified. Such portion identifications aids may include measuring devices, e.g., measuring cups, bowls, or spoons, for determining portion sizes, drawings and diagrams depicting the size of portions of various food products, and templates for identifying portion sizes on serving plates. Further, it includes food exchange lists, in which the meal components are identified by the calorie content and level of nutritional enhancement per portion size. Food record sheets are also included for recording daily consumption of meal components and the calorie content and nutritional enhancement corresponding to the portion sizes consumed. In addition, the package contains a "survival kit" which includes information and food products that enable the patient to stay within the guidelines of the dietary health management system when traveling or when meal components of the system are otherwise unavailable.

In another embodiment, the invention is a method for improving the compliance of a patient with a dietary health management system which provides a predetermined daily calorie content and level of nutritional enhancement. This method includes the steps of providing the patient with portion identification aids for identifying portion sizes of meal components consumed, providing the patient with food record sheets for recording daily consumption of the meal components and the calorie content and nutritional enhancement corresponding to the portion sizes, and providing the patient with food exchange lists determining the calorie content and nutritional enhancement per portion sizes consumed. The method further comprises the step of conferring with the patient on a regular basis to review the food record sheets and provide counseling regarding food consumption patterns. Moreover, the method includes the step of providing the patient with the survival kit described above.

Yet a further embodiment of the invention is a method for determining the effectiveness of a diet program for administration to a patient having at least one diet-responsive condition. This method includes the steps of selecting a plurality of patients, each having at least one quantifiable indicator of each of the conditions. The at least one quantifiable indicator of each of the diet-responsive conditions may then be identified and measured for each of the patients during a baseline period. Further, each of the patients may be monitored during the baseline period, e.g., about four weeks, to determine a baseline quality of life. The plurality of patients then may be randomly divided between a first group and a second group, and the diet program may be administered to each of the patients in the first group during an intervention period, e.g., about 10 weeks. During that same period, however, each of the patients in the second group is maintained on a control diet, e.g., the AHA diet, with known beneficial effects on the at least one indicator. The at least one indicator of each of the conditions is monitored for each of the patients after the intervention period.

The diet program may include the dietary health management system described above including a plurality of the individual meals, which supply the patient with a desired total daily calorie content, improved quality of life, and sufficient nutritional enhancement to facilitate management of the diet-responsive condition. Moreover, each of the patients may also be tested to determine his or her quality of life before (e.g., during the baseline period) and after the intervention period. In addition, initial serum vitamin, iron, and trace mineral levels may be determined for each patient at a beginning and an end of the baseline period and after the intervention period. By assessing changes in serum vitamin, iron, and trace mineral levels at a beginning and an end of the baseline period and after the intervention period, dietary adequacy and adverse effects may be assessed.

It is a technical advantage of this invention, confined by clinical trials, that the system and method claimed herein achieve weight loss, improved quality of life, improvements in quantifiable indicators of diet-responsive conditions, and a high degree of compliance.

Other objects, features, and advantages will be apparent to those of ordinary skill in the art when the following detailed description of the invention and the drawings are considered.

BRIEF DESCRIPTION OF THE DRAWINGS

FIG. 2 shows a chart for determining specific dietary allotments at differing caloric levels.

FIGS. 4a–c show charts depicting the reductions in systolic and diastolic blood pressure measurements and cholesterol, triglyceride, HDL, and LDL levels for a patient with hyperlipidemia over a ten (10) week clinical trial period.

DETAILED DESCRIPTION OF THE INVENTION

Dietary Health Management System

Figure 1:
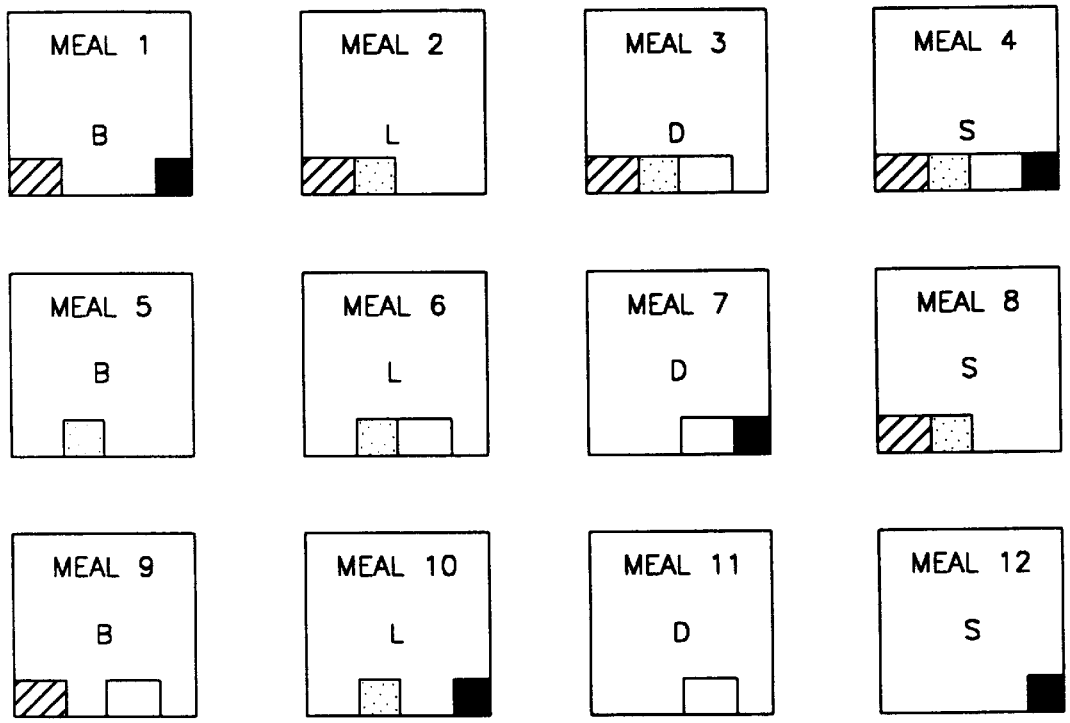
FIG. 1 depicts a schematic representation of the relationship between the categories, meal groups, and meals in a diet planning and control system.

In one embodiment, the present invention provides a therapeutic dietary system for a patient having at least one diet-responsive condition. Such diet-responsive conditions may include obesity, hypertension, hyperlipidemia, cancer, diabetes, and combinations thereof. The system comprises a meal program containing a plurality of prepackaged individual meals. Each of the individual meals contains a predetermined level of nutritional enhancement. Consumption of a plurality of the individual meals, optionally with the addition of supplemental foods, supplies the patient with the desired total daily calorie content and sufficient nutritional enhancement to facilitate management of the diet-responsive condition.

Generally, nutritional enhancement involves fortification of meal components of the prepackaged meals with macro- or micronutrients, or both, and controlling of the levels of other elements within those components. Thus, nutritional enhancement may include fortifying one or more components of a meal with vitamins, minerals, or a combination of these elements. In addition, nutritional enhancement may involve adding or controlling dietary fiber; controlling of the amounts of simple sugars through the use of fructose or sugar substitutes, or both, and controlling of levels and types of fat and protein and the levels of cholesterol and sodium in the meal. Preferably, after nutritional enhancement, a daily diet of prepackaged meals provides: (1) dietary fiber in the range of about 20 to 30 grams (0.71 to 1.06 ounces); (2) vitamins and minerals at about 100% of levels recommended by authoritative governmental (e.g., National Academy of Sciences, National Research Council, Food and Nutrition Board Subcommittee on the Recommended Dietary Allowances) and scientific/professional organization (e.g., National Cancer Institute, American Diabetes Association, American Heart Association, and American Dietetic Association); (3) sodium in an amount less than about 3000 mg; (4) protein, such that about 15% to 20% of caloric intake is derived from protein; and (5) fat, such that about 20 to 30% of caloric intake is derived from fat.

The degree of fortification is determined by a variety of factors, including the methods of processing, packaging, storing, and preparing the meals; the duration of storage; and the amounts of these elements desired for effective management of the diet-responsive condition. The meal components may include a meat component, e.g., beef, pork, fish, or poultry, and under the present therapeutic system, nutritional enhancement may be applied to either the meat or non-meat components or both. Because fortification of some meal components may require approval by a governmental regulatory authority, such as the U.S. Department of Agriculture (USDA), the meals may employ compartmentalized containers to segregate the fortified meal components from those which are not fortified.

The micronutrients are added to the meals with overages that are designed to deliver levels of these nutrients when the meals are consumed by the patient. Thus, the micronutrient overages must be sufficiently high to provide the desired levels after processing, e.g., the mixing, precooking and cooking; freezing, dehydrating, or freeze-drying; storing, e.g., maintaining the meal in a frozen or dry condition for an extended period; and preparing, e.g., the reheating or final cooking, of the meal. Preferably, such meals may be reheated or cooked by placing the meal on a stove top, in a conventional, or microwave oven or by submerging a sealed cooking bag in boiling water. Because the system is designed to be used over extended periods of time, the individual meals preferably have a sufficiently long storage or shelf-life that they may be purchased and stored well in advance of consumption.

A storage or shelf-life under retail conditions in a range of about nine to twelve months is desirable, but preferably the storage or shelf-life is not less than about nine months. Under retail conditions, frozen meals are maintained at a temperature of about −18° C. (0° F.) and may have a shelf-life of about twelve months. Because storage temperatures of residential frozen storage equipment vary greatly, shelf-life of meals stored in residences is less predictable.

Supplemental foods may include at least one food selected from one or more of the following categories of fruits, vegetables, and dairy products. The selection of supplemental foods involves the active participation of the patient, and the supplemental foods may be consumed with or between consumption of the prepackaged individual meals. For example, a selection from the dairy product group may include a serving, e.g., about 237 mL (8 ounces), of slim milk; light, non-fat, or plain yogurt; or the like. For example, a selection from the fruit group may include an apple, banana, orange, pear, plum, or the like, or a predetermined serving size of assorted types of berries (e.g., about 1¼ cup), grapefruit (e.g., ½ grapefruit), melon (e.g., ⅓ melon), or cherries or grapes (e., about one cup—about 12 cherries or 15 grapes). Alternatively, the fruit selection may comprise about ½ cup of chopped, cooked, or canned unsweetened fruit, or fruit juice. For example, a selection from the vegetable group may include a serving of asparagus, beets, tomatoes, mushrooms, carrots, zucchini, green beans, broccoli, or the like. These vegetables may be consumed raw (e.g., 1 cup) or cooked (e.g., ½ cup). Further, the vegetable selection may consist of a bowl of tossed salad including controlled amounts of low-calorie and low-sodium salad dressing. For example, a dairy product such as skim milk, may be consumed with the breakfast meals including a fortified cereals an apple much as an apple may be consumed with the lunch meals; and a vegetable such as a tossed salad, may be consumed with the dinner meals. Thus, a wide variety of fruits, vegetables, and dairy products may be chosen to comply with the health management system. The foregoing examples emphasize this versatility.

The dietary health management systems and methods of the present invention are designed to provide a controlled and consistent daily caloric level. For example, the systems and methods may provide a core caloric level of between about 1200 and 1500 calories per day. This core level is provided by the consumption of a diet comprising a breakfast meal, a lunch meal, a dinner meal, a snack meal, and supplemental foods selected from the group consisting of dairy products, fruits, and vegetables.

No single caloric level or range is appropriate for all patients. A caloric level, however, may be calculated for patients based on their sex, present body weight, height, and level of activity. Such calculations may be made using the Harris-Benedict equations described herein in Example 14, infra. Because dietary health management most often will include some degree of weight loss, the systems and methods of the present invention are designed to provide a daily caloric intake for achievement of weight loss while consuming a healthier diet.

In addition, using known relationships between calculated caloric intake needs (e.g., from Harris-Benedict equations) and actual caloric intake, it is possible to estimate the amount of weekly weight loss. Similarly, for patients who have caloric levels above the core caloric level of the systems and methods of the present invention it is possible to accurately anticipate unintended or unwanted weight loss. For example, a patient with a caloric level of about 1600 calories per day, who consumes a core diet providing about 1500 calories per day, will lose about 0.91 kg (2 lbs.) each week during which the patient consumes that diet. Such weight loss can be avoided by the consumption of adjustors, e.g., snack meals, which increase the daily caloric intake by incremental amounts.

Snack meals may include, for example, frozen low-fat yogurt, pretzels, bagels, popcorn, and low-fat corn or potato chips. By consuming an appropriate number of such snacks meals, the patient may increase his or her daily caloric intake to a desired range. For example, if desired daily caloric intake is in a range of about 1600 to 1700 calories, a patient may consume one snack meal. If, however, he or she desires to increase daily caloric intake to between about 1800 and 1900 calories, the patient may consume two snack meals. Preferably, each of the adjustors has the same content of calories and macro- and micronutrients, so that a patient may choose to consume the appropriate number of a variety of adjustors or of the same adjustor, depending upon individual tastes or changing desires.

Vitamins and Minerals

The vitamins and minerals that form a part of the nutritional enhancement of the present invention are generally provided in the form of a DFEA. The composition of the DFEA may vary, but typically includes the following: Vitamins A, $B_1$, $B_2$, $B_3$, $B_6$, $B_{12}$, C, D, E, and K, and Biotin, Calcium, Copper, Folic Acid, Iodine, Iron, Magnesium, Manganese, Pantothenic Acid, Phosphorus, and Zinc. For example, as noted above, the plurality of meal groups may comprise a breakfast meal group, a lunch meal group, and a dinner meal group. Breakfast meals and the dinner meals each may be fortified with the DFEA to provide about 35% of the desired daily level of the vitamins and minerals, and lunch meals may be fortified to provide about 30% of the desired daily level of the vitamins and minerals. See Table I, infra. Adjustors may be fortified to provide about 5% of the desired daily level of the vitamins and minerals. Thus, adjustors may be used to add vitamins and minerals to a patient's diet, as well as to increase caloric intake.

By complying with the steps in the health management system including consuming supplemental foods in addition to a plurality of fortified meals each day, the patient receives a predetermined amount of the daily desired level (e.g., USRDA, where applicable) of vitamins and minerals. In general, total daily fortification provided by the health management system may be at least about 50% and preferably at least about 75% and more preferably at least about 90% of the USRDA. In the most preferred embodiment, the fortification is at least about 100% of the USRDA.

Simple Sugars

The ADA has recommended for diabetics that the intake of simple sugars be restricted and that complex carbohydrates be increased. Typical 1500 calorie menus for the ADA show simple sugars to be within a range of about 96 to 107 grams of sugar from fruits and vegetables from the ADA exchange lists. In order to reduce the amount of simple sugars in each meal (such as sucrose, table sugar, and glucose), fructose or sugar substitutes, such as aspartame and the like, may be added to meal components in place of the simple sugars. The diet of the present invention is intended to supply less than about 96 grams of simple sugars per day mainly in the form of fructose. Preferably, however, the therapeutic meals provide no more than about 65 grams of simple sugar per day. This amount is significantly lower than the amount calculated for 1500 ADA caloric menus. As noted above, good or pleasing taste is important to high compliance with a health management system. However, it achieves this result in part because fructose and sugar substitutes are generally sweeter than simple sugars, and, therefore, less sugar may be required to obtain the desired flavor.

Fiber

As discussed above, the levels of dietary fiber, as well as the levels of sodium in a diet may effect blood pressure. The addition of fiber to meal components brings the daily fiber supply to within the recommended range of about 20 to 30 grams per day in accordance with the recommendations of the NCI. Dietary fiber added to the meal components or adjustors may be selected from any of the known commercially available fiber-providing sources such as pectin; maltodextrin products; gum arabic, and hydrolyzed guar gum, xantham gum, and the like. Other sources of fiber, such as apple, wheat, citrus pulp, citrus, cellulose, corn, cottonseed, oat, pea, rice, soy, sugarbeet fiber, and the like, may also be used. However, due to the importance of good taste and appearance to diet compliance, the addition of fiber is controlled, so that the appearance, consistency, taste, and aroma of the meal components remain substantially unaffected. Further, because excessive amounts of dietary fiber may result in adverse effects, in the present invention, daily dietary fiber intake does not exceed about 35 grams per day.

Sodium

Sodium content of meals is controlled, such that total daily sodium intake is less than about 3000 mg. Preferably, total daily sodium intake is less than about 2400 mg, e.g., in a range of about 2000 to 2400 mg. Sodium, especially that derived from the use of salt (NaCl) to flavor meals, may be replaced with other elements or "non-salt" compositions to reduce overall sodium content. The primary "non-salt" compositions for sodium replacement are potassium salts, such as potassium chloride (KCl) or potassium lactate.

Potassium

In the present invention, daily potassium intake under the diet may be at least about 3000 mg, preferably in a range of about 3150 to 3850 mg and more preferably, about 3500 mg. Meal components may be modified with "non-salt" flavor enhancers such as those containing potassium, to preserve flavor in view of the addition of macro- and micronutrients during the fortification process. In addition to its beneficial use as a "salt" substitute, the addition of potassium to a patient's diet has positive health effects. In epidemiologic and animal studies, the risk of stroke-related deaths has been shown to be inversely related to potassium intake. These results have been observed over a range of blood pressures. However, the relationship appears to be dependent upon daily intake. In addition to the potassium chloride or lactate sources, nutritional enhancement by increasing potassium content may be achieved through the addition of food grade potassium salts such as potassium citrate.

The combination of a low sodium diet with a high potassium diet may result in lower blood pressure levels. Moreover, such a diet may result in reduced frequency of stroke.

Protein

In accordance with recommendations by the National Academy of Science, National Research Council and Food and Nutrition Board Subcommittee on the Recommended Dietary Allowances, diets preferably provide about 20 to 30% of calories from fat, about 15 to 20% from protein, and about 55 to 60% from carbohydrates. These guidelines are met by the system and method of the present invention. Further, mixed protein from plant and animal sources are used whenever possible. Moreover, when animal proteins are utilized lean and medium-fat meats, poultry, and fish are the preferred source. The precise amount of protein consumed by a patient daily is dependent on the total calories to be consumed.

Fats

Under the present invention, calories from fat are preferably limited about 20 to 30% of the daily total calories. In particular, under the systems and methods described herein, SFA intake is reduced, such that less than about 10% of calories each day is derived from SFA, and preferably, calories derived from SFAs are in a range of about 7 to 10%. Such further reductions may be best achieved by substituting additional complex carbohydrates and monounsaturated fatty acids (MUFAs) for SFAs in the diet. Similarly, intake of PUFAs are also strictly controlled. Currently, North Americans derive about 7% of daily calorie needs (caloric intake) from PUFAs. Although studies have shown an increase in colon and breast cancer at very high PUFA intake levels, where PUFAs are partially substituted for SFAs, PUFA intake accounting for up to about 10% of daily caloric intake does not appear to significantly increase the risk of cancer. In the systems and methods of the present invention, about 10% of daily calories are derived from PUFAs. Finally, the remainder of the decrease is SFA intake is met by a relative increase in MUFA intake. Studies have indicated that the substitution of MUFAs for SFAs may reduce cancer risks, especially with respect to colo-rectal cancer. Under the systems and methods of the present invention, more than about 10% of daily caloric intake is derived from MUFAs and preferably, daily calories derived from MUFAs are in a range of about 10 to 13%.

Preferably, fat intake may be reduced by curtailing the major sources of dietary fat rather than by eliminating whole categories of foods. For example, by substituting fish, poultry without skin, lean meats and low- or non-fat dairy products for high-fat foods, a patient may lower total fat and SFA intake while ensuring an adequate intake of iron and calcium—two nutrients of special importance to female patients. Dietary fat may also be reduced by limiting intake of baked goods containing high levels of fat and spreads and dressings containing fat and oils.

In addition to SFA intake, cholesterol intake is a major dietary determinant of serum total and LDL cholesterol levels. Thus, the reduction of SFA intake is preferably coupled with a reduction in cholesterol intake. In particular, it is desirable to maintain cholesterol intake at less than about 300 mg per day. The systems and methods described herein preferably supply cholesterol in a range of about 200 to 300 mg per day. This is accomplished in part by the reduction or elimination of fatty meats and whole-milk dairy products from the preparation of therapeutic meals. Further, as noted above, the use of oils and fat in meal component preparation is strictly controlled.

Diet-Responsive Conditions

OBESITY

For adult patients of normal weight, the systems and methods of the present invention permit the ingestion of adequate calories to meet most essential nutrient needs. Physicians may prescribe caloric reduction, e.g., less than maintenance caloric level, for overweight patients. The systems and methods take into account the caloric requirements of the patient based on height, weight, sex, age, and activity level. Although the health management system is designed to provide a core of between about 1200 and 1500 calories daily, this amount may be increased through the addition of adjustors, i., snacks, to increase caloric levels to desired targets. However, if weight loss is desired, it is strictly controlled, such that after the first two weeks employing the system or utilizing the method, weight loss does not exceed about 0.91 kg (2 lbs.) per week. Weight loss may continue until a weight loss goal or endpoint, individually determined for a patient by a nutritionist, is reached.

HYPERTENSION

The systems and methods of the present invention provide low daily sodium intake levels. Therapeutic meals are designed to provide less than about 2400 mg of sodium per day, and preferably, a daily sodium intake in a range of about 2000 to 2400 mg.

Benefits from the lowering of sodium may accrue to any patient. However, the systems and methods described herein are not intended to replace antihypertensive medication where such medication is appropriate. In some cases, however, proper utilization of the systems and methods of this invention limiting sodium intake may reduce or eliminate the need for such medication. The monitorable indicator for the use of the systems and methods to control diet-responsive hypertension is blood pressure. Patients most likely to achieve a reduction are patients who are without antihypertensive medication that have blood pressure (sitting) with a systolic pressure in a range of about 140 to 180 mmHg or a diastolic pressure in a range of about 90 to 105 mmHg, or with antihypertensive medication, that have a blood pressure (sitting) with a systolic pressure in a range of about 135 to 180 mmHg or a diastolic pressure in a range of about 85 to 100 mmHg.

Additionally, the systems and methods of the present invention, may achieve a reduction of systolic and diastolic blood pressure measurements in a range of at least about 1 to 10 mmHg. However, in a preferred embodiment the reduction in blood pressure is greater than about 5 mmHg.

HYPERLIPIDEMIA

The systems and methods of the present invention provide that the PUFA intake of patients not significantly exceed about 10% of total calories. The appropriate health management endpoints, i.e., monitorable indicators, are total serum cholesterol, LDL, and triglycerides. Further the systems and methods described herein are not intended to replace any lipid lowering medication where such medication is appropriate. In some cases, however, through proper utilization of the systems and the methods of this invention lowering cholesterol levels may reduce or eliminate the need for such medication. Patients most likely to achieve reductions in cholesterol and triglyceride levels are patients who are without lipid lowering medication that have cholesterol levels in a range of about 220 to 300 mg/dl or triglyceride levels in a range of about 200 to 1000 mg/dl, or both, or with lipid lowering medication that have cholesterol levels in a range of about 200 to 260 mg/dl or triglycerides in a range of about 200 to 1000 mg/dl.

The systems and methods of the present invention may achieve significant reductions in serum cholesterol levels. Cholesterol may be reduced by an amount in a range of about 10 to 20 mg/dl, and more preferably, by at least about 15 mg/dl. Triglycerides may be reduced by an amount in a range of about 10 to 25 mg/dl, and more preferably, by an at least about 20 mg/dl. LDL may also be reduced by an amount in a range of about 5 to 20 mg/dl, and more preferably, by at least 15 mg/dl. In addition to reductions in serum cholesterol, this invention may result in reductions in systolic and diastolic blood pressure in a range of about 1 to 10 mmHg for a patient suffering from hyperlipidemia. More preferably, the patient's systolic blood pressure may be reduced by an amount in a range of less than about 5 mmHg, and the patient's diastolic blood pressure may be reduced by about 1 mmHg.

DIABETES

The indicators associated with diet-responsive diabetes are determined for the individual patient. The diet is designed to control plasma glucose and plasma lipid levels and maintain body weight at a level appropriate for the particular patient. As noted above, the systems and methods described herein formulate appropriate caloric diets tailored to the patient's height, weight, age, sex and activity level and which provide about 15 to 20% of calories from protein, about 20 to 30% of calories from fat, and about 55 to 60% of calories from carbohydrates. The diet provides between about 20 and 30 grams of dietary fiber each day. Finally, by using fructose and sugar substitutes, such as aspartame, less than about 96 grams of simple sugars are consumed daily by the patient, and preferably, about 65 grams of simple sugars are consumed daily.

Patients most likely to benefit from the systems and methods of the present invention are non-insulin dependent diabetics who take no hypoglycemic agents and have fasting plasma glucose levels of greater than about 140 mg/dl and $HbA_{1c}$ levels of not greater than about 200% of median for assay, i.e., less than about 15.4, or who take oral hypoglycemic agents and have $HbA_{1c}$ levels of between about 100 and 175% of median for assay, i.e., between about 7.7 and 13.48 mg/dl.

The systems and methods of the present invention may achieve stabilization or significant reductions in $HbA_{1c}$. For example, both medically stabilized and non-medically stabilized diabetics may obtain reductions in $HbA_{1c}$ of at least about 1%, and in a preferred embodiment, the reduction in $HbA_{1c}$ may be up to about 2% when comparing baseline period to the end of the intervention period. Further, non-medically stabilized diabetics may experience reductions in plasma glucose levels while employing the systems and methods described herein. Medically stabilized diabetics may experience increased ease in maintaining plasma glucose level stability or reducing plasma glucose levels while employing these systems and methods.

CANCER

The systems and methods of the present invention are designed to provide dietary fiber in the ranges recommended by the NCI and to limit fat consumption to no more than about 30% of daily caloric intake. Moreover, the addition of the DFEA to therapeutic meals for inclusion in the health management systems and methods is intended to ensure that the patient receives the daily recommended allowances of numerous vitamins and minerals, including Vitamins A and C. Further, as noted above, the systems and methods disclosed herein provide for selection of supplemental foods by the patient from among the groups consisting of fruits, vegetables, and low-fat dairy products. All of these approaches reduce the risk factors associated with various types of cancers, as discussed above.

Compliance and Quality of Life

Compliance is perhaps the single most important element in a successful dietary health management system or method. The level of compliance depends in part on the motivation and drive of the patient. Nevertheless, it may also be influenced by identifiable and controllable factors, such as the ease with which the system may be utilized or the method may be followed; the taste, appearance, and in general, the desirability of consuming the prescribed meals; the flexibility of the system or method; and the degree of satisfaction, e.g., the improvement in quality of life experienced by the patient.

In support of the systems and methods of the present invention, patients are supplied with a Compliance Support Package (CSP). This CSP includes (1) food record sheets, (2) dietary information, including exchange lists and portion size control information, and (3) a survival kit. The food record sheets allow patients to record daily food consumption and are useful during counseling sessions to confirm that the diet is being followed. The exchange lists allow a patient to select meals suitable to a variety of diet-responsive conditions (meal categories) from a variety of meal groups. Further, the exchange lists identify various supplemental foods which may be selected by the patients to fulfill the requirements of the dietary health management system or method. The portion size control information allows the patient to understand and better control portion sizes consumed. Other dietary information instructs the patient as to how the system or method operates and why the patient should or should not consume various foods or foods prepared in a particular manner. Also included is information on exercise behavior modification and proper nutrition.

The CSP includes a survival kit which allows a patient to consume foods when prescribed meals or food exchange items are not available without forcing the patient to abandon the system or method. In this manner, the patient may avoid "cheating" on his or her diet even in an emergency. Survival kits may be especially appropriate to persons who travel frequently for business or pleasure or who, for other reasons, are denied the facilities to prepare a meal recommended by the system or method. Not only may the survival kit identify possible substitutes, but such kits may contain emergency snacks to satisfy an immediate need while preserving the progress achieved by the system or method.

As clinical results have shown, this CSP achieves improved compliance, and, therefore, improves the effectiveness of the systems and methods of the present invention. In addition, use of the CSP of this invention has been shown to improve compliance regardless of the diet used. Thus the CSP of this invention can be used with other diets.

In addition to the health benefits of a successful health management system, the patient's attitudes, mental health and outlook, and overall sense of well-being, i e., the patient's quality of life, may also be positively impacted. This impact may be measured by relatively objective criteria such as improved compliance with the health management system's dietary requirements, and improved function in daily activities. It may also be reflected in more subjective, but equally measurable, criteria, such as stress levels, perception of mental health, satisfaction with the dietary health management system, assessment of personal appearance, and self esteem.

Quality of life may be measured by various empirical tests. These may consist of established quality of life assessments along with three new scales that were designed to assess the impact of nutritional interventions on quality of life. Thus, these tests provide a broad profile on quality of life that is sensitive to dietary manipulations. The primary indices of quality of life are the Mental Health Index and the General Health Perceptions scale. The instruments were developed by the Rand Corporation for the Health Insurance Study and are considered among the best available instruments for measuring quality of life. Additional tests may be administered which measure nutritional affect, work performance, daily activity, sexual function, nutritional health perceptions, nutritional hassles, and the impact of nutrition on social function. When the dietary health management system of the present invention is employed by patients, they consistently demonstrate statistically significant, e.g., $p<0.05$ level, higher scores on these quality of life assessments as compared to when these same patients are not employing the systems or methods of the present invention, e.g., intervention vs. baseline assessment.

Dietary Health Management Planning and Control System

A health management planning and control system, according to this invention, may provide nutritionally enhanced dietary management to a patient having at least one of the diet-responsive conditions discussed above. This system comprises a plurality of prepackaged individual meals wherein each of the meals is associated with a particular group. Each meal has a group identifying code corresponding to the type of meal, e.g., meal occasion, such as breakfast. Moreover, each of the meals further includes at least one category identifying code corresponding to a particular diet-responsive condition. Each of the individual meals contains a predetermined level of nutritional enhancement. By consuming a plurality of the individual meals having the appropriate category identifying code, the patient is supplied with a desired total daily calorie content and sufficient nutritional enhancement to facilitate management of the diet responsive condition. A typical desired total daily caloric intake may be between about 1200 and 1500 calories per day. If necessary, this daily caloric intake may be adjusted by the consumption of adjustors, such as frozen low-fat yogurt; health food bars, such as granola bars; popcorn; low-fat potato or corn chips; bagels, pretzels, fruit and vegetable juice beverages, and the like.

Referring to FIG. 1, a schematic representation of a preferred embodiment a health management planning and control system according to the present invention is depicted. Twelve meals are depicted, which have been divided into four groups: breakfast meals (B), lunch meals (L), dinner meals (D), and snack meals (S). Each group has a group identifying code, i., B, L, D, and S. Nevertheless, the group identifying codes may be selected from the group consisting of a plurality of letters, numbers, colors, shapes, textures, or combinations thereof.

These group identifying codes are used to exchange or substitute items of a meal group within a category or to select meals suitable to more than one category. These categories may include groups of meals that address conditions such as (1) hypertension, e.g., meals with low sodium content; (2) hyperlipidemia, e.g., meals low in cholesterol and SFAs; (3) non-insulin dependent diabetes, e.g., low in simple sugars and high in fiber; (4) cancer prevention, e.g., high in fiber low in cholesterol and SFAs. In FIG. 1, for example, meals in a meal group associated with a first dietary category, hypertension, may be identified with a thatched box, while a second dietary category, hyperlipidemia, may be identified with a dotted box. As shown in the figure, individual meals may be associated with more than one category. In FIG. 1, the categories are identified by graphically unique boxes, but in accordance with the foregoing description, a variety of colors, shapes, or the like may be used.

In another example, meals in a meal group associated with a first dietary category may be identified with a blue circle. Similarly, meals in a meal group associated with a second dietary category may be identified with a red star. Meals in a meal group, which are suitable for inclusion in the first and second dietary categories, may be identified with a blue circle and a red star, or some combination of the features of the two identifying codes, e.g., a blue star. Thus, meals are not limited to inclusion in a single dietary category.

Dietary Health Management Method

In accordance with this invention, a method for dietary health management comprises treating a diet-responsive condition by adherence to particular recommended dietary levels. Such methods include the step of identifying quantifiable treatment indicators of the diet-responsive condition.

For example, when disease state is obesity, the quantifiable treatment indicator usually will be body weight and Body Mass Index (BMI). Similarly, when the condition is non-insulin dependent diabetes mellitus, the quantifiable treatment indicators may be fasting plasma glucose level and $HbA_{1c}$. When the condition is hyperlipidemia, the quantifiable treatment indicators may be total serum cholesterol, LDL, and triglycerides; and when the condition is hypertension, the quantifiable treatment indicators may be average sitting diastolic blood pressure and average sitting systolic blood pressure. Thus, unique quantifiable treatment indicators are identifiable for the majority of diet-responsive conditions.

The method further includes the step of administering a complete daily diet comprising a plurality of prepackage individual meals to the patient. Each of the individual meals contains a predetermined level of nutritional enhancement. Consumption of a diet comprising a plurality of the individual meals supplies the patient with the desired total daily sustenance and sufficient nutritional enhancement to facilitate management of the diet-responsive condition. As noted above, this diet preferably is supplemented by the patient's selection of foods from each of three groups consisting of fruits, vegetables, and dairy products. Further, the method may include the step of monitoring the condition treatment indicators.

Prepackaged Therapeutic Meals

According to an embodiment of the invention, a prepackaged therapeutic meal may be used by a patient having at least one diet-responsive condition. Such meals comprise a plurality of separate meal components. At least one of these meal components may include a predetermined level of nutritional enhancement. By consuming a plurality of these meals along with appropriate adjustors and supplemental foods chosen by the patient, the patient receives the desired total daily calories and sufficient nutritional enhancement to facilitate management of the diet-responsive condition.

The meal components may include a meat component, e.g., beef or pork, fish, or poultry. The health management system may apply the nutritional enhancement to either the meat or non-meat components or both. Because fortification of some meal components, may require approval by a governmental agency, such as the USDA with respect to meats, the meals are packaged in compartmentalized containers to segregate the meal components. As discussed above, the degree of fortification is determined by a variety of factors, including the methods of processing, packaging, storage, and preparation of the meals; the duration of storage; the amounts of these elements desired for effective treatment of the diet-responsive condition, and meal appearance. The prepackaged, individual meals may be frozen for storage or in some cases packaged for room temperature storage, e.g., retorted soups, stews, and pastas.

In a preferred embodiment, as shown in Table I, the breakfast and dinner meals may contain about 35% of the DFEA and the lunch meal may contain about 30% of the DFEA. The preparation of DFEA in the various meals may of course be varied to suit particular patients needs. Because patients may not desire to consume all of the components of a particular meal on any given day or because additional calories or micronutrient levels are desired, the breakfast, lunch, and dinner meals may be supplemented with an adjustor, each containing about 5% of the DFEA. As noted above, such adjustors may also be used to increase the caloric content of a diet. Suitable adjustors may include low-fat frozen yogurt, granola bars, bagels, popcorn, low-fat potato or corn chips, and pretzels.

TABLE I

| | Daily Desired Level of Fortification | | |
|---|---|---|---|
| Nutrient | Breakfast Meal (35%) | Lunch Meal (30%) | Dinner Meal (35%) |
| VITAMIN A, (IU) | 1750 | 1500 | 1750 |
| VITAMIN D, (IU) | 140 | 120 | 140 |
| VITAMIN E, (IU) | 10.5 | 9 | 10.5 |
| VITAMIN C, (mg) | 35 | 30 | 35 |
| VITAMIN $B_1$, (mg) | 0.53 | 0.45 | 0.53 |
| VITAMIN $B_2$, (mg) | 0.6 | 0.51 | 0.6 |
| VITAMIN $B_3$, (mg) | 7 | 6 | 7 |
| VITAMIN $B_6$, (mg) | 0.7 | 0.6 | 0.7 |
| VITAMIN $B_{12}$, (mcg) | 2.1 | 1.8 | 2.1 |
| BIOTIN, (mcg) | 105 | 90 | 105 |
| FOLIC ACID, (mg) | 0.14 | 0.12 | 0.14 |
| PANTOTHENIC ACID, (mg) | 3.5 | 3 | 3.5 |
| VITAMIN K, (mcg) | 28 | 24 | 28 |
| CALCIUM, (mg) | 420 | 360 | 420 |
| COPPER, (mg) | 1.05 | 0.9 | 1.05 |
| IRON, (mg) | 6.3 | 5.4 | 6.3 |
| MAGNESIUM, (mg) | 105 | 90 | 105 |
| MANGANESE, (mg) | 1.75 | 1.5 | 1.75 |
| PHOSPHORUS, (mg) | 262.5 | 225 | 262.5 |
| ZINC, (mg) | 5.25 | 4.5 | 5.25 |
| IODINE, (mcg) | 52.5 | 45 | 52.5 |

As seen in the embodiments of Table II, it is preferred to distribute the DFEA among at least two food components. This distribution helps to avoid problems with taste and insure at least partial benefits of the fortification when the patient does not consume any one fortified component.

TABLE II

| Type | Meal Component - % DFEA (Approx.) |
|---|---|
| A. BREAKFASTS | |
| Pancakes | Pancakes - 15% (2 Pancakes) |
| | Orange Juice Beverage - 20% |
| French Toast | French Toast - 15% (2 Slices) |
| | Orange Juice Beverage - 20% |
| Scrambled Eggs | Apple Oatmeal Muffins - 15% (2 Muffins) |
| | Orange Juice Beverage - 20% |
| Breakfast Sandwich | English Muffin - 15% |
| | Orange Juice Beverage - 20% |
| B. LUNCHES | |
| Beef Soup | Roll - 20% |
| | Apple Cinnamon Sauce - 10% |
| Chicken Noodle Soup | Roll - 20% |
| | Apple Crisp - 10% |
| Split Pea Soup | Corn Bread - 20% |
| | Cherry Crisp - 10% |
| Pasta Dinner | Garlic Roll - 25% |
| | Fruit Compote - 5% |
| Turkey Sandwich | Apple Crisp - 18% |
| | Whipped Potatoes - 12% |
| C. DINNERS | |
| Pot Roast | Roll - 20% |
| | Sauce for Corn - 5% |
| | Peach Crisp - 10% |
| Traditional Turkey | Roll - 20% |
| | Sauce for Vegetables - 5% |
| | Cheesecake - 10% |
| Sirloin Tips | Roll - 20% |
| | Sauce for Vegetables - 5% |
| | Cheesecake - 10% |
| Glazed Turkey | Sauce for Vegetables - 10% Total (5% for each vegetable) |
| | Pasta Sauce - 15% |
| | Apple Crisp - 10% |

TABLE II-continued

| Type | Meal Component - % DFEA (Approx.) |
|---|---|
| Barbecue Chicken | Garlic Roll - 25% |
| | Rice Mixture - 5% |
| | Sauce for Vegetables - 5% Total |
| | (2.5% for each vegetable) |
| Grilled Mustard Chicken | Roll - 25% |
| | Rice Mixture - 5% |
| | Sauce for Vegetables - 5% Total |
| | (2.5% for each vegetable) |
| Meatloaf | Sauce for Vegetables - 5% |
| | Mushroom Sauce - 5% |
| | Cheese Sauce - 15% |
| | Cheesecake - 10% |
| Salisbury Steak | Sour Cream Sauce - 15% |
| | Sauce for Vegetables - 5% |
| | Mushroom Sauce - 5% |
| | Apple Crisp - 10% |
| Herb Roasted Chicken | Roll - 20% |
| | Sauce for Vegetables - 5% |
| | Cherry Crumb - 10% |
| Beef Stew | Corn Bread - 20% |
| | Sauce for Vegetables - 5% |
| | Apple Cinnamon Sauce - 10% |

Food Products

An embodiment of the invention also includes a food product for administration to a patient having at least one diet-responsive condition. The product comprises a nutritionally enhanced meal component selected from the group consisting of meats, baked goods, sauces, starch sources, soups, cereals, desserts, and fruit and vegetable juice beverages. The component supplies dietary fiber in an amount of up to about 30 grams; vitamins and minerals at a range of about 5 to 35% of the USRDA, see Table III, infra, containing recently determined USRDA values; sodium in an amount less than about 2400 mg; protein, such that up to about 20% of daily caloric intake is derived from protein; and fat, such that up to about 30% of daily caloric intake is derived from fat. Although the meal components may include a meat component, preferably, the nutritionally enhanced meal components are non-meat components. As noted above, the nutritionally enhanced meal component may include baked goods, e.g., rolls, muffins, and breads; sauces, e.g., vegetable sauces, pasta sauce, and meat sauces; starch sources, e.g., whipped potatoes and rice; cereals; soups; desserts; and fruit and vegetable juice beverages.

Examples of meal components of which may be fortified by adding the DFEA at a specified level, include meats, such as poultry, fish or beef, i.e., Salisbury Steak and Meatloaf; baked goods, such as rolls, i.e., garlic rolls, muffins and breads; cereals; soups; desserts, i.e., apple crisp; starch sources, i.e., whipped potatoes; fruit or vegetable juice beverages, i.e. orange juice drink; and fruit compotes; and sauces for vegetables and meats, i.e., sour cream sauce. See Tables XI–XVIII, infra, which details the fortification of particular food components.

Dietary Food Enhancement Agent

A DFEA for fortifying food products may comprise predetermined amounts of vitamins and minerals. As discussed above, various vitamins and minerals included in the DFEA may include a combination of essential vitamins and minerals for which a recommended dietary allowance, such as the USRDA, has been established. In a preferred embodiment, the combination of essential vitamins and minerals comprises A, B, C, D, and E Vitamins and Calcium, Phosphorus, Magnesium, and Iron. In a more preferred embodiment, the combination of essential vitamins and minerals may comprise Vitamins A, $B_1$, $B_2$, $B_3$, $B_6$, $B_{12}$, C, D, E, and K, and Biotin, Calcium, Copper, Folic Acid, Iodine, Iron, Magnesium, Manganese, Pantothenic Acid, Phosphorus, and Zinc. Preferably, the vitamins and minerals are premixed to provide a powdered, free-flowing, stable DFEA useful for fortification of various food components.

The vitamins and minerals included in the DFEA may be present in amounts equivalent to those present in a recommended dietary allowance as determined by governmental or national health organizations, e.g., USRDA. Vitamins and minerals, for which a USRDA amount has been established, are identified in Table III.

TABLE III

U.S. Recommended Dietary Allowance USRDA)

| NUTRIENT | USRDA |
|---|---|
| VITAMIN A | 5000 IU |
| VITAMIN $B_1$ | 1.5 mg |
| VITAMIN $B_2$ | 1.7 mg |
| VITAMIN $B_3$ | 20 mg NE[1] |
| VITAMIN $B_6$ | 2 mg |
| VITAMIN $B_{12}$ | 6 mcg |
| VITAMIN C | 60 mg |
| VITAMIN D | 400 IU |
| VITAMIN E | 30 IU |
| VITAMIN K | NONE ESTABLISHED |
| BIOTIN | 300 mcg |
| CALCIUM | 1000 mg |
| COPPER | 2 mg |
| FOLIC ACID | 400 mcg |
| IODINE | 150 mcg |
| IRON | 18 mg |
| MAGNESIUM | 400 mg |
| MANGANESE | NONE ESTABLISHED |
| PANTOTHENIC ACID | 10 mg |
| PHOSPHORUS | 1000 mg |
| ZINC | 15 mg |

[1]Niacin Equivalent.

The DFEA may also include various vitamins and minerals in the ranges depicted on Table IV. The precise composition of vitamins and minerals selected from about the ranges disclosed on Table IV, depend on the type of meal component to which the DFEA is to be added and the method of preparation of that meal component and its method of storage. The DFEA also optionally contains an excipient in an amount up to about 20% by weight of the mixture. Known food grade excipients such as those based on maltodextrins may be used. The form (both chemical and physical) of the food grade vitamins and minerals employed to make the DFEA should be selected to maintain good taste and attractive appearance of food products an meals containing the DFEA. The vitamin and mineral forms also should have sufficient stability to remain active after the processing and storage conditions discussed above. Any of the conventional forms of vitamins having the desired characteristics set out above can be used to formulate the DFEA. Mineral fortification to the extent contemplated by this invention, however, may require selection of nonconventional forms to avoid problems with taste and appearance. In one preferred embodiment this objective is achieved by employing calcium citrate and dicalcium phosphate as a mixed source of calcium; employing dicalcium phosphate additionally as a source of phosphorus; and employing magnesium phosphate as an additional source of phosphorus and a source of magnesium.

TABLE IV

DFEA Compositions

| NUTRIENT | CONCENTRATION RANGE |
|---|---|
| VITAMIN A | 1125–9900 IU |
| VITAMIN $B_1$ | 0.41–2.07 mg |
| VITAMIN $B_2$ | 0.23–2.24 mg |
| VITAMIN $B_3$ | 6.3–25.3 mg NE |
| VITAMIN $B_6$ | 0.54–2.75 mg |
| VITAMIN $B_{12}$ | 1.08–8.58 mcg |
| VITAMIN C | 31.5–330 mg |
| VITAMIN D | 36–682 IU |
| VITAMIN E | 9.45–49.5 IU |
| VITAMIN K | 0–110 mcg |
| BIOTIN | 94.5–412.5 mcg |
| CALCIUM | 108–1333.2 mg |
| COPPER | 0.95–3.63 mg |
| FOLIC ACID | 126–660 mcg |
| IODINE | 47.25–189.75 mcg |
| IRON | 5.67–20.79 mg |
| MAGNESIUM | 72–339.9 mg |
| MANGANESE | 1.58–6.05 mg |
| PANTOTHENIC ACID | 2.7–13.75 mg |
| PHOSPHORUS | 33.75–841.65 mg |
| ZINC | 4.05–17.66 mg |

Encapsulation technology may be employed during the processing of the various meal components to ensure that vitamins and minerals are delivered in sufficient quantity and remain stable during meal processing, storage, and preparation. Any method of encapsulation capable of achieving these results may be used. In the vitamin and mineral mixture described above, for example, the vitamins and minerals may be enclosed within edible microcapsules. One preferred form of microencapsulation technology is described in U.S. patent application Ser. No. 08/076,709 filed Jun. 15, 1993, entitled "Encapsulated Additives," which is incorporated herein by reference. The microcapsules may have cores containing the vitamins and minerals, which is insoluble in water, but which melts and releases the vitamins and minerals at water temperatures above about 35° C. (95° F.). Each core may be completely surrounded by an outer shell. This shell may comprise a shell forming material that has a thermal gelation temperature within a range of about 35 to 77° C. (95 to 171° F.). In particular, the outer shell may comprise methylcellulose.

Clinical Testing Method

Accurate clinical testing is important to the development and implementation of a dietary health management system. Clinical testing, however, does not cease when such a system enters use. Continued clinical testing is used to ensure the continued efficacy of therapeutic meals and therapeutic products, to introduce additional varieties of therapeutic meals and therapeutic products, and to identify areas for improvement in the manufacture and implementation of the system.

A clinical testing method for determining the effectiveness of a diet program, such as a dietary health management system, for administration to a patient having at least one diet-responsive condition includes the steps of selecting a plurality of patients, each having at least one quantifiable indicator of at least one of the conditions. Patients continue their usual diet during a baseline period. The baseline period serves several functions in the clinical testing method. First, it allows test supervisors to identify unsuitable patients and remove them from the patient population before the dietary health management system is administered to a group of the patient population. Further, each of the patients may be monitored during the baseline period to determine a baseline quality of life. Moreover, the at least one indicator for the at least one diet-responsive condition, as well as other health criteria, may be measured for each patient during the baseline period. Thus, all of the patients may be placed on a more equal footing by gathering data and eliminating unacceptable members of the patient population before the testing a dietary health management system, and the patients may be educated on how to use a dietary health management system. In addition, during the baseline period, the test supervisors may educate the patients on the purpose of the dietary health management system and benefits of a nutritionally enhanced diet in addressing diet-responsive conditions.

At least one quantifiable indicator of each of the diet-responsive conditions is identified and measured for each of the patients during a baseline period. Each of the patients is monitored during the baseline period to determine a baseline quality of life. The plurality of patients then is randomly divided between a first group and a second group. The system then is administered to each of the patients in the first group during an intervention period. Each of the patients in the second group, however, is maintained on a control diet, e.g., a diet that follows the AHA guidelines, with known beneficial effects on the at least indicator of each of the conditions. These indicators are monitored for each of the patients after the intervention period. As described above, the system includes a plurality of prepackaged individual meals, such as the therapeutic meals, which supply the patients with a desired total daily calorie content, improved quality of life, and sufficient nutritional enhancement to facilitate management of the diet-responsive. Because the control diet is has known benefits, this method allows the test supervisors to compare active diets.

Referring to Tables V–VII, the activities involved in a clinical testing method are described in greater detail. The clinical test described in these tables is essentially the same test described herein at Example 14. The test includes a four week baseline period followed by a ten week intervention period. Table V describes the clinical events scheduled for each period. These events include the physical testing of the patients during each period, the administration of quality of life questionnaires, and the like. In Table VI, the clinical schedule for laboratory testing is set forth. These tests include some initial screening tests for identifying unacceptable members of the patient population and initial and final tests for the intervention period. Table VII describes the nutrition related activities during the baseline and intervention periods. Each of the activities, events, and tests is described in more detail with respect to Example 14, infra.

TABLE V

Clinical Schedule

| Activity | \-4 | \-3 | \-2 | \-1 | 0 | 1 | 2 | 3 | 4 | 5 | 6 | 7 | 8 | 9 | 10 |
|---|---|---|---|---|---|---|---|---|---|---|---|---|---|---|---|
| | BASELINE | | | | INTERVENTION | | | | | | | | | | |
| Consent signed | X | | | | | | | | | | | | | | |
| Inclusion/Exclusion | X | | | | | | | | | | | | | | |
| History | | X | | | | | | | | | | | | | |
| Physical | | X | | | | | | | | | | | | | X |
| ECG | | X | | | | | | | | | | | | | |
| Weight and BP | X | X | X | X | X | | X | | X | | X | | X | | X |
| Waist/Hip Measure | | | | | X | | | | | | | | | | X |
| Temperature | | | | | X | | | | | | | | | | X |
| Medication Record | X | X | X | X | X | | X | | X | | X | | X | | X |
| Adverse Events | | X | X | X | X | | X | | X | | X | | X | | X |
| BMI | X | | | | | | | | | | | | | | |
| Questionnaires | | | XL | | XL | | X | | XL | | X | | X | | XL |
| DC Vitamins | X | | | | | | | | | | | | | | |
| Randomized | | X | | | | | | | | | | | | | |
| Lab Draws | X | X | | | X | | | | X | | | | X | | X |
| Disp for 24-hr urine | | | | X | | | X | | | | | | X | | |
| Instruct to Fast for Next Visit | | X | | X | | | | X | | | | X | | X | |

TABLE VI

Clinical Schedule for Laboratory Analyses

| ACTIVITY | \-4 | \-3 | \-2 | \-1 | 0 | 1 | 2 | 3 | 4 | 5 | 6 | 7 | 8 | 9 | 10 |
|---|---|---|---|---|---|---|---|---|---|---|---|---|---|---|---|
| | BASELINE | | | | INTERVENTION | | | | | | | | | | |
| CBC | X | | | | | | | | | | | | | | |
| Chemistry Profile | X | | | | X | | | | | | | | | | X |
| Plasma Glucose | | | | | X | | | | X | | | | | | X |
| $Hb_{A1C}$ | X | | | | X | | | | | | | | | | X |
| Fructosamine | | | | | X | | | | | | | | | | X |
| Lipoprotein Profile | | | X | | X | | | | X | | | | X | | X |
| Insulin | | | | | X | | | | | | | | | | X |
| S-PTH | | | | | X | | | | | | | | | | X |
| S-1,25(OH)$_2$D and S-25-OH-D | | | | | X | | | | | | | | | | X |
| Trace minerals | | | | | X | | | | | | | | | | X |
| Vitamins | | | | | X | | | | | | | | | | X |
| U/A with micro | X | | | | | | | | | | | | | | |
| Collect 24-hr urine | | | | | X | | | | X | | | | | | X |

TABLE VII

Clinical Schedule of Nutritionist-Related Activities

| ACTIVITY | \-4 | \-3 | \-2 | \-1 | 0 | 1 | 2 | 3 | 4 | 5 | 6 | 7 | 8 | 9 | 10 |
|---|---|---|---|---|---|---|---|---|---|---|---|---|---|---|---|
| | BASELINE | | | | INTERVENTION | | | | | | | | | | |
| Administer Preliminary Diet Questionnaire | | X | | | | | | | | | | | | | |
| Instruct participant to maintain usual diet during baseline period | | X | X | X | | | | | | | | | | | |
| Food record instructions (distribute 3-day food record booklet) | | X | | | | | | | | | | | | | |
| Distribute food record form with pre-selected collection days | | X | X | | X | | X | | X | | X | | X | | |
| Review food record with participant | | | X | X | | | X | | X | | X | | X | | X |
| Determine diet prescription | | | X | | | | | | | | | | | | |
| Fax Diet Prescription Worksheet | | | X | | | | | | | | | | | | |
| Fax Nutritionist Notes | | | X | X | | | X | | X | | X | | X | | X |

TABLE VII-continued

Clinical Schedule of Nutritionist-Related Activities

| | WEEK OF STUDY | | | | | | | | | | | | | | |
|---|---|---|---|---|---|---|---|---|---|---|---|---|---|---|---|
| | BASELINE | | | | | INTERVENTION | | | | | | | | | |
| ACTIVITY | -4 | -3 | -2 | -1 | 0 | 1 | 2 | 3 | 4 | 5 | 6 | 7 | 8 | 9 | 10 |
| Food Vouchers to Control Group | | | | | X | | X | | X | | X | | X | | |
| Menu Selection for Experimental Group | | | | X | X | | X | | X | | X | | | | |
| Fax Menu Selection to Distribution Site | | | | X | X | | X | | X | | X | | | | |
| Prepare participant manual for Week 0 visit (add diet prescription sheet/sample menus) | | | | | X | | | | | | | | | | |
| Diet instruction on appropriate intervention | | | | | | | X | | X | | | | | | |

EXAMPLES

The invention may be further understood by a consideration of the following examples, which are intended to be purely exemplary of the use of the invention.

Example 1

This example demonstrates the preparation of DFEAs suitable for use according to the present invention. The composition of a vitamin and mineral mixture comprising one preferred DFEA for use in fortifying meals and meal components of this invention, which are to be frozen before consumption, is shown in Table III.

TABLE VIII

Vitamin and Mineral Mixture (Frozen Foods)

| NUTRIENT | CONCENTRATION | FORM |
|---|---|---|
| VITAMIN A | 9000 IU | Vitamin A Palmitate |
| VITAMIN $B_1$ | 1.88 mg | Thiamine Mononitrate |
| VITAMIN $B_2$ | 2.04 mg | Riboflavin |
| VITAMIN $B_3$ | 23 mg NE | Niacinamide |
| VITAMIN $B_6$ | 2.5 mg | Pyridoxine Hydrochloride |
| VITAMIN $B_{12}$ | 7.8 mcg | Vitamin $B_{12}$ |
| VITAMIN C | 300 mg | Ascorbic Acid |
| VITAMIN D | 620 IU | Vitamin $D_3$ |
| VITAMIN E | 45 IU | Vitamin E Acetate |
| VITAMIN K | 100 mcg | Vitamin $K_1$ |
| BIOTIN | 375 mcg | Biotin |
| CALCIUM | 1212 mg | Calcium Citrate/Dicalcium Phosphate |
| COPPER | 3.3 mg | Copper Gluconate |
| FOLIC ACID | 600 mcg | Folic Acid |
| IODINE | 172.5 mcg | Potassium Iodine |
| IRON | 18.9 mg | Ferric Orthophosphate |
| MAGNESIUM | 309 mg | Magnesium Phosphate |
| MANGANESE | 5.5 mg | Manganese Sulfate |
| PANTOTHENIC ACID | 12.5 mg | Calcium Pantothenate |
| PHOSPHORUS | 765.14 mg | Magnesium Phosphate/Dicalcium Phosphate |
| ZINC | 16.05 mg | Zinc Oxide |

The vitamin and mineral concentrations given in Table VIII include sufficient overage percentages to insure that the desired concentrations are available for consumption after processing, storing, e.g., about a nine month frozen retail storage period, and preparing of the therapeutic meals.

The DFEA of Table VIII was prepared as follows: first, the following vitamin components (available from Roche Vitamins and Fine Chemicals) were combined in a Day mixer at room temperature and under controlled humidity, e.g. in a range of about 35 to 75% RH, to produce a homogenous vitamin mix: 36 mg of Vitamin A Palmitate (250 micron spray dried); 300 mg of Ascorbic Acid; 6.2 mg of Vitamin $D_3$-100 S.D.; 90 mg of Vitamin E acetate 50% (CWS/F); 10 mg of Vitamin $K_1$, 1% (spray dried); 1.88 mg of Thiamine Mononitrate; 2.04 mg of Riboflavin; 23 mg of Niacinamide; 3.03 mg of Pyridoxine Hydrochloride; 0.6 mg of Folic Acid; 7.8 mg of Vitamin $B_{12}$, 0.1% (spray dried); 0.375 mg of Biotin; and 13.63 mg of Calcium Pantothenate. Second, a mineral mix was separately prepared in a Day mixer under similar conditions to those discussed above by combining 1.65 grams of Dicalcium Phosphate; 3.45 grams of Calcium Citrate; 2.2 grams of Magnesium Phosphate; 67.5 mg of Ferric Orthophosphate; 20.06 mg of Zinc Oxide; 0.25 mg of Potassium Iodide; 23.57 mg of Copper Gluconate; and 15.85 mg of Manganese Sulfate. The vitamin and mineral mixes were then combined in a Day mixer along with less than about 20% by weight of maltodextrin (as an excipient) and mixed under the above described controlled atmospheric conditions until the product was free flowing and homogenous, and would not separate.

Similarly, Table IX sets forth another embodiment of a DFEA for use in cereals according to this invention. The cereals are intended to be consumed with about 237 mL (8 ounces) of skim milk, i.e., a dairy product selected as a supplemental food by the patient. The skim milk supplies some of the vitamins and minerals, e.g., calcium, supplied in larger quantities in the DFEA described in Table VIII.

TABLE IX

Vitamin and Mineral Mixture (Cereals)

| NUTRIENT | CONCENTRATION | FORM |
|---|---|---|
| VITAMIN A | 2500 IU | Vitamin A Palmitate |
| VITAMIN $B_1$ | 0.59 mg | Thiamine Mononitrate |
| VITAMIN $B_2$ | 0.32 mg | Riboflavin |
| VITAMIN $B_3$ | 7.7 mg NE | Niacinamide |
| VITAMIN $B_6$ | 0.84 mg | Pyridoxine Hydrochloride |
| VITAMIN $B_{12}$ | 2.4 mcg | Vitamin $B_{12}$ |
| VITAMIN C | 140 mg | Ascorbic Acid/Sodium Ascorbate |
| VITAMIN D | 80 IU | Vitamin $D_3$ |
| VITAMIN E | 15.75 IU | Vitamin E Acetate |
| BIOTIN | 141.75 mcg | Biotin |
| CALCIUM | 123.6 mg | Calcium Carbonate |
| COPPER | 1.16 mg | Copper Gluconate |
| FOLIC ACID | 210 mcg | Folic Acid |
| IODINE | 60.38 mcg | Potassium Iodide |
| IRON | 6.62 mg | Ferric Orthophosphate |
| MAGNESIUM | 82.4 mg | Magnesium Phosphate/Magnesium Oxide |
| MANGANESE | 1.93 mg | Manganese Sulfate |
| PANTOTHENIC ACID | 4.5 mg | Calcium Pantothenate |

TABLE IX-continued

Vitamin and Mineral Mixture (Cereals)

| NUTRIENT | CONCENTRATION | FORM |
|---|---|---|
| PHOSPHORUS | 38.63 mg | Magnesium Phosphate |
| ZINC | 4.73 mg | Zinc Oxide |

Table X sets forth yet another embodiment of a DFEA for use in fortifying soups, stews, pastas, and other retorted, shelf-stable meals and meal components of this invention.

TABLE X

Vitamin and Mineral Mixture (Soups and Other Retorted Meals)

| NUTRIENT | CONCENTRATION | FORM |
|---|---|---|
| VITAMIN A | 9000 IU | Vitamin A Palmitate |
| VITAMIN $B_1$ | 2.63 mg | Thiamine Mononitrate |
| VITAMIN $B_2$ | 2.04 mg | Riboflavin |
| VITAMIN $B_3$ | 23 mg NE | Niacinamide |
| VITAMIN $B_6$ | 2.5 mg | Pyridoxine Hydrochloride |
| VITAMIN $B_{12}$ | 7.8 mcg | Vitamin $B_{12}$ |
| VITAMIN C | 300 mg | Ascorbic Acid |
| VITAMIN D | 620 IU | Vitamin $D_3$ |
| VITAMIN E | 45 IU | Vitamin E Acetate |
| VITAMIN K | 100 mcg | Vitamin $K_1$ |
| BIOTIN | 375 mcg | Biotin |
| CALCIUM | 1212 mg | Calcium Citrate/Dicalcium Phosphate |
| COPPER | 3.3 mg | Copper Gluconate |
| FOLIC ACID | 600 mcg | Folic Acid |
| IODINE | 172.5 mcg | Potassium Iodide |
| IRON | 18.9 mg | Ferric Orthophosphate |
| MAGNESIUM | 309 mg | Magnesium Phosphate |
| MANGANESE | 5.5 mg | Manganese Sulfate |
| PANTOTHENIC ACID | 12.5 mg | Calcium Pantothenate |
| PHOSPHORUS | 765.14 mg | Magnesium Phosphate/Dicalcium Phosphate |
| ZINC | 16.05 mg | Zinc Oxide |

Example 2
Bread Products

A nutritionally enhanced garlic roll component according to the present invention was formulated as follows:

| Ingredient | Percentage (by weight) |
|---|---|
| Water | 35.6916 |
| Flour, std patent | 29.78 |
| Butter | 2.98 |
| Salt (NaCl) | 0.67 |
| Wheat Gluten | 7.45 |
| Yeast Compressed | 1.2384 |
| Fructose (Crystalline) | 1.49 |
| S-500 Blue Dough Conditioner[2] | 0.6 |
| Traviata Flavoring[3] | 0.6 |
| Solka Floc Fiber[4] | 8.94 |
| Lac Prodan Protein[5] | 2.98 |
| DFEA | 6.33 |
| Onion Powder | 1.19 |
| Garlic Powder | 0.06 |
| | 100% |

[2] Available from Puratos Corporation of Cherry Hill, N.J.
[3] Available from Puratos Corporation of Cherry Hill, N.J.
[4] Available from Fiber Sales & Development Corporation of Urbana, Ohio.
[5] Available from Royal Proteins Corporation of Rosemont, Ill.

To prepare the garlic roll, the water, flour, wheat gluten, and yeast slurry were automatically scaled to a Stefan Mixer for mixing. The remaining ingredients were hand scaled to the mixer. The dough was mixed at a temperature of about 28° C.±0.55° (83° F.±1°). The dough was then divided, relaxed, and shaped into uncooked rolls with a length in a range of about 5.08 to 5.72 cm (2 to 2.25 in.). The uncooked rolls were then proofed for about 55 minutes at a temperature in a range of about 27 to 32° C. (80 to 90° F.). The proofed rolls were then baked for about 17 minutes at a temperature in a range of about 188 to 221° C. (370 to 430° F.). After baking, the rolls were spiral cooled for about 55 minutes to a temperature of about 13° C. (55° F.). After cooling the rolls were blast frozen. Table XI depicts the vitamin and mineral content of the resulting fortified garlic roll, which contains about 25% of daily DFEA in about a 29 gram serving.

TABLE XI

Garlic Roll

| Nutrient | Fortification Level |
|---|---|
| VITAMIN A, (IU) | 2250 |
| VITAMIN D, (IU) | 155 |
| VITAMIN E, (IU) | 11.25 |
| VITAMIN C, (mg) | 75 |
| VITAMIN $B_1$, (mg) | 0.47 |
| VITAMIN $B_2$, (mg) | 0.51 |
| VITAMIN $B_3$, (mg NE) | 5.75 |
| VITAMIN $B_6$, (mg) | 0.63 |
| VITAMIN $B_{12}$, (mcg) | 1.95 |
| BIOTIN, (mcg) | 93.75 |
| FOLIC ACID, (mcg) | 150 |
| PANTOTHNIC ACID, (mg) | 3.13 |
| VITAMIN K, (mcg) | 25 |
| CALCIUM, (mg) | 303 |
| COPPER, (mg) | 0.83 |
| IRON, (mg) | 4.73 |
| MAGNESIUM, (mg) | 77.25 |
| MANGANESE, (mg) | 1.38 |
| PHOSPHORUS, (mg) | 191.29 |
| ZINC, (mg) | 4.01 |
| IODINE, (mcg) | 43.13 |

Example 3
Cereal Products

A cereal product, e.g., a raisin bran cereal component, obtained from Gilster-Mary Lee Corporation of Chester, Ill., may be nutritionally enhanced according to the present invention by adding DFEA thereto and supplemented with about 237 mL (8 ounces) of skim milk to form a breakfast meal. Table XII depicts the vitamin and mineral content of the fortified raisin bran cereal, which when combined with about 237 mL (8 ounces) of skim milk, contains about 35% of the daily DFEA in about a 56 gram serving of the raisin bran cereal.

TABLE XII

Raisin Bran Cereal

| Nutrient | Fortification Level |
|---|---|
| VITAMIN A, (IU) | 2500 |
| VITAMIN D, (IU) | 80 |
| VITAMIN E, (IU) | 15.75 |
| VITAMIN C, (mg) | 140 |
| VITAMIN $B_1$, (mg) | 0.59 |
| VITAMIN $B_2$, (mg) | 0.32 |
| VITAMIN $B_3$, (mg NE) | 7.7 |
| VITAMIN $B_6$, (mg) | 0.84 |
| VITAMIN $B_{12}$, (mcg) | 2.4 |

TABLE XII-continued

Raisin Bran Cereal

| Nutrient | Fortification Level |
|---|---|
| BIOTIN, (mcg) | 141.75 |
| FOLIC ACID, (mcg) | 210 |
| PANTOTHENIC ACID, (mg) | 4.5 |
| CALCIUM, (mg) | 123.6 |
| COPPER, (mg) | 1.16 |
| IRON, (mg) | 6.62 |
| MAGNESIUM, (mg) | 82.4 |
| MANGANESE, (mg) | 1.93 |
| PHOSPHORUS, (mg) | 38.63 |
| ZINC, (mg) | 4.73 |
| IODINE, (mcg) | 60.38 |

Example 4

Dessert Products

A nutritionally enhanced glaze for dessert product, i.e., an apple crisp component, according to the present invention was formulated as follows:

| Ingredient | Weight (lbs) |
|---|---|
| Apple Concentrate | 147 |
| Natural Apple Flavoring | 2.5 |
| FT33 (Flavor Enhancer) | 0.42 |
| Ground Cinnamon | 3.36 |
| Fine Granulated Salt (NaCl) | 0.32 |
| DFEA | 37.6 |
| Aspartame | 0.84 |
| Starch Slurry | 141.75 to 156.75 |

To prepare the apple crisp glaze, about 57 liters (15 gallons) of water were placed in a kettle, and the apple concentrate was added to the water. The water and apple concentrate were agitated in the kettle, and during agitation, the cinnamon, salt, aspartame, flavor enhancer, DFEA, and natural apple flavoring were added. The mixture was then gauged to about 265 liters (70 gallons) and heated to a temperature of about 88° C. (190° F.). As agitation continued, the starch slurry was added to the kettle mixture and the temperature was simultaneously increased to about 91° C. (195° F.). Hot water, e.g., water at a temperature of about 91° C. (195° F.), was added to the kettle mixture to adjust the volume to about 379 liters (100 gallons). Agitation of the adjusted kettle mixture was continued until a satisfactory color and viscosity of the mixture was obtained. The kettle mixture was then transferred for garnishing of the apple crisp component.

Table XIII depicts the vitamin and mineral content of the resulting fortified apple crisp, which contains about 18% of the daily DFEA in about a 70 gram serving.

TABLE XIII

Apple Crisp

| Nutrient | Fortification Level |
|---|---|
| VITAMIN A, (IU) | 1620 |
| VITAMIN D, (IU) | 111.6 |
| VITAMIN E, (IU) | 8.1 |
| VITAMIN C, (mg) | 54 |
| VITAMIN $B_1$, (mg) | 0.34 |
| VITAMIN $B_2$, (mg) | 0.37 |

TABLE XIII-continued

Apple Crisp

| Nutrient | Fortification Level |
|---|---|
| VITAMIN $B_3$, (mg NE) | 4.14 |
| VITAMIN $B_6$, (mg) | 0.45 |
| VITAMIN $B_{12}$, (mcg) | 1.4 |
| BIOTIN, (mcg) | 67.5 |
| FOLIC ACID, (mcg) | 108 |
| PANTOTHENIC ACID, (mg) | 2.25 |
| VITAMIN K, (mcg) | 18 |
| CALCIUM, (mg) | 218.16 |
| COPPER, (mg) | 0.59 |
| IRON, (mg) | 3.4 |
| MAGNESIUM, (mg) | 55.62 |
| MANGANESE, (mg) | 0.99 |
| PHOSPHORUS, (mg) | 137.72 |
| ZINC, (mg) | 2.89 |
| IODINE, (mcg) | 31.05 |

Example 5

Starch Products

A nutritionally enhanced whipped potatoes component according to the present invention was formulated as follows:

| Ingredients | Weight (lbs) |
|---|---|
| Unsalted Butter | 19.4 |
| Non-fat Milk (Spray-dried) | 7.14 |
| White Brazilian Pepper (Pulverized) | 0.21 |
| Fine Granulated Salt (NaCl) | 1.26 |
| Water | 161.55 |
| Granular Potassium Chloride (KCl) | 0.85 |
| DFEA | 5.5 |
| Soy Fiber (Fibrim 1200 ®)[6] | 8 |
| Spice Mix | 1 |
| Dehydrated Potato Flakes | 54.6 |
| Water (for rehydration) | 161.55 |

[6] Available from Protein Technology of St. Louis, Mo.

To prepare the whipped potatoes components, the spray-dried non-fat milk and sufficient water to rehydrate the milk are added to a Norman mixer. Salt, potassium chloride, white pepper, soy fiber, DFEA, a fluid premix, and melted butter also are added to the mixer, and the combination is mixed until it forms a homogenous solution. The solution then is transferred via a C-Bucket or an equivalent to an AMF mixer equipped with a double-wing spade. The potato flakes and rehydrating water are added to the AMF mixer, and the AMF mixer is run at slow speed, e.g., about 40 rpms, until uniform, e.g., for about one minute. The mixer speed then is increased to a medium speed, e.g., about 100 rpms, until the solution is smooth, e.g., in a range of about 3 to 4 minutes. The whipped potatoes are packaged within about 30 minutes of the completion of mixing or may be covered and refrigerated for no more than about two hours prior to packaging.

Table XV depicts the vitamin and mineral content of the resulting fortified whipped potato component which contains about 12% of the daily DFEA in about an 80 gram serving.

TABLE XIV

Whipped Potatoes

| Nutrient | Fortification Level |
| --- | --- |
| VITAMIN A, (IU) | 1080 |
| VITAMIN D, (IU) | 74.4 |
| VITAMIN E, (IU) | 5.4 |
| VITAMIN C, (mg) | 36 |
| VITAMIN $B_1$, (mg) | 0.23 |
| VITAMIN $B_2$, (mg) | 0.25 |
| VITAMIN $B_3$, (mg NE) | 2.76 |
| VITAMIN $B_6$, (mg) | 0.3 |
| VITAMIN $B_{12}$, (mcg) | 0.94 |
| BIOTIN, (mcg) | 45 |
| FOLIC ACID, (mcg) | 72 |
| PANTOTHENIC ACID, (mg) | 1.5 |
| VITAMIN K, (mcg) | 12 |
| CALCIUM, (mg) | 145.44 |
| COPPER, (mg) | 0.4 |
| IRON, (mg) | 2.27 |
| MAGNESIUM, (mg) | 37.08 |
| MANGANESE, (mg) | 0.66 |
| PHOSPHORUS, (mg) | 91.82 |
| ZINC, (mg) | 1.93 |
| IODINE, (mcg) | 20.7 |

Example 6
Fruit or Vegetable Juice Products

A nutritionally enhanced orange juice drink component according to the present invention was formulated as follows:

| Ingredient | Percentage (by weight) |
| --- | --- |
| Citric Acid | 1.2 |
| Potassium Citrate | 0.93 |
| Keltrol ® TF Xanthan Gum[7] | 0.20 |
| Aspartame | 0.11 |
| Water | 50 |
| Fibersol ®[8] | 12.83 |
| DFEA | 2.9 |
| Orange Juice Concentrate | 25 |
| Glycerin | 3 |
| Beta Carotene 1% CWS | 0.06 |
| Orange Booster | 0.07 |
| Orange Flavor | 0.4 |
| Orange Pulp | 3.3 |
|  | 100% |

[7] Available from Kelco, a unit of Monsanto, of Okmulege, Okla.
[8] Available from Matsutami Co. of Itami City, Hyogo Japan.

To prepare the orange juice drink, one half of the batch weight of water and Fibersol® a Maltodextrin fiber source was blended in a Norman mixer for about one minute. A dry blend of citric acid, potassium citrate, Keltrol® xantham gum, aspartame, DFEA, and beta carotene was added to the ingredients in the Norman mixer. The combined mixture was then blended for about another two minutes. Finally, the orange flavors and glycerine were added to the combined mixture, and the contents of the Norman mixer are blended for about three more minutes.

After the initial blending was complete, the contents of the Norman mixer were transferred to a holding tank. The orange juice concentrate, orange pulp, and remaining water were added to the holding tank, and the contents of the holding tank were thoroughly mixed. After final mixing, the contents of the holding tank was transferred to about 60 gram±1 gram pouches. The pouches are enclosed in cartons and frozen with dry ice.

Table XV depicts the vitamin and mineral content of the resulting fortified orange juice drink, which contains about 20% of the daily DFEA in about a 60 gram serving.

TABLE XV

Orange Juice Drink

| Nutrient | Fortification Level |
| --- | --- |
| VITAMIN A, (IU) | 1800 |
| VITAMIN D, (IU) | 124 |
| VITAMIN E, (IU) | 9 |
| VITAMIN C, (mg) | 60 |
| VITAMIN $B_1$, (mg) | 0.38 |
| VITAMIN $B_2$, (mg) | 0.41 |
| VITAMIN $B_3$, (mg NE) | 4.6 |
| VITAMIN $B_6$, (mg) | 0.5 |
| VITAMIN $B_{12}$, (mcg) | 1.56 |
| BIOTIN, (mcg) | 75 |
| FOLIC ACID, (mcg) | 120 |
| PANTOTHENIC ACID, (mg) | 2.5 |
| VITAMIN K, (mcg) | 20 |
| CALCIUM, (mg) | 242.4 |
| COPPER, (mg) | 0.66 |
| IRON, (mg) | 3.78 |
| MAGNESIUM, (mg) | 61.8 |
| MANGANESE, (mg) | 0.66 |
| PHOSPHORUS, (mg) | 153.03 |
| ZINC, (mg) | 3.21 |
| IODINE, (mcg) | 34.5 |

Example 7

Soup Products

A nutritionally enhanced vegetable soup component according to the present invention was formulated as follows:

| Ingredient | Weight (lbs) |
| --- | --- |
| Dry Beef Stock | 6.81 |
| Dehydrated Granular Garlic | 0.81 |
| Granular KCl | 1.62 |
| Gum Arabic | 4.32 |
| Maltodextrin | 72.43 |
| Salted, Concentrated Beef Bone Stock | 10.81 |
| Beef Flavor | 1.08 |
| Tomato paste | 7.57 |
| Liquid, burnt sugar (50% concentration - 0.049 Gallon) | 0.5 |
| Fine Granulated Salt (NaCl) | 1.2 |
| Brine (26.4% Salt (NaCl) | 4.92 |
| Textured Vegetable Protein Strips (70% Protein) | 68.11 |
| Carrots (Fresh weight)* | 108.11 |
| Celery Stalks (Fresh) | 59.46 |
| Potatoes (Fresh weight)* | 75.68 |
| Potatoes (cubed-dehydrofrozen) | 37.84 |
| Beans (1" cut-blanched/frozen) | 34 |
| Corn (Yellow-Frozen) | 33 |
| Peas (Alaska) | 33 |
| Peas (Sweet - Std Grade) | 33 |
| Peas (Sweet - Grade B) | 33 |
| Tomatoes | 200 |
| Oil (Corn) | 10.81 |
| Oil (Cottonseed) | 10.81 |
| Oil (Cottonseed - Non hydrogenated) | 10.81 |
| Oil (Soybean - lightly hydrogenated) | 10.81 |
| Oil (Soybean) | 10.81 |
| DFEA | 8.32 |
| Potato Starch | 30 |

-continued

| Ingredient | Weight (lbs) |
|---|---|
| Yellow Dye | 9.73 |
| Flavor Enhancers | 2.62 |

*Blanched weight equals about 94.7% of fresh weight.

To prepare the vegetable soup, the potatoes and carrots were blanched for about one minute. The tomato paste, beef bone stock, beef flavor, burnt sugar, flavor enhancers, yellow dye, maltodextrin, garlic, KCl, salt, and gum arabic were combined with water at a temperature less than about 82° C. (180° F.) in a kettle. The kettle mixture was heated to a temperature of about 82° C. (180° F.), and the textured vegetable protein and DFEA were added to the kettle. The heating of the kettle was stopped, and the potato starch was mixed into the kettle mixture for about one minute. After the addition of the potato starch was complete, the green beans, peas, corn, potatoes, carrots, celery, tomato pieces, and oils were added to the kettle mixture, and the kettle weight was adjusted.

Table XVI depicts the vitamin and mineral content of the resulting fortified vegetable soup, which contains about 30% of the daily DFEA in about a 340 gram serving.

TABLE XVI

Vegetable Soup

| Nutrient | Fortification Level |
|---|---|
| VITAMIN A, (IU) | 2700 |
| VITAMIN D, (IU) | 186 |
| VITAMIN E, (IU) | 13.5 |
| VITAMIN C, (mg) | 90 |
| VITAMIN $B_1$, (mg) | 0.79 |
| VITAMIN $B_2$, (mg) | 0.61 |
| VITAMIN $B_3$, (mg NE) | 6.9 |
| VITAMIN $B_6$, (mg) | 0.75 |
| VITAMIN $B_{12}$, (mcg) | 2.34 |
| BIOTIN, (mcg) | 112.1 |
| FOLIC ACID, (mcg) | 180 |
| PANTOTHENIC ACID, (mg) | 3.75 |
| VITAMIN K, (mcg) | 30 |
| CALCIUM, (mg) | 363.6 |
| COPPER, (mg) | 0.99 |
| IRON, (mg) | 5.67 |
| MAGNESIUM, (mg) | 92.7 |
| MANGANESE, (mg) | 1.65 |
| PHOSPHORUS, (mg) | 229.54 |
| ZINC, (mg) | 4.82 |
| IODINE, (mcg) | 51.75 |

Example 8

Sauce Products

A nutritionally enhanced fruit sauce component according to the present invention was formulated as follows:

| Ingredient | Weight (lbs) |
|---|---|
| Apple Concentrate | 55.25 |
| Natural Apple Flavor | 2.15 |
| Beet Juice | 3.1 |
| Crystalline Fructose | 69.85 |
| Citric Acid | 1.64 |
| Fine Granulated Salt (NaCl) | 1.77 |
| Potassium Citrate | 1.77 |
| DFEA | 8.12 |
| Maize Starch | 151.05 to 166.95 |
| Water (for Starch Slurry) | 110 |

To prepare the fruit sauce, 57 liters (15 gallons) of water was placed in a kettle, and the apple concentrate, apple flavor, beet juice, fructose, salt, citric acid, DFEA, and potassium citrate were added to the water. The beet juice was diluted in a ratio of about 1:1 with water at a temperature less than about 88° C. (190° F.) before it was added to the kettle. The contents of the kettle were gauged to a volume of about 284 liters (75 gallons) and then stirred and heated to about 88° C. (190° F.). A starch slurry was formed by mixing the starch and water in a Norman mixer. After the initial heating, the starch slurry was screened and added to the kettle, and the kettle contents were reheated to about 91° C. (195° F.) to fully expand the thickener. The contents of the kettle were then gauged to a volume of about 379 liters (100 gallons).

Table XVII depicts the vitamin and mineral content of the resulting fruit sauce component, which contains about 5% of the daily DFEA in about a 90 gram serving.

TABLE XVII

Fruit Sauce

| Nutrient | Fortification Level |
|---|---|
| VITAMIN A, (IU) | 450 |
| VITAMIN D, (IU) | 31 |
| VITAMIN E, (IU) | 2.25 |
| VITAMIN C, (mg) | 15 |
| VITAMIN $B_1$, (mg) | 0.09 |
| VITAMIN $B_2$, (mg) | 0.1 |
| VITAMIN $B_3$, (mg NE) | 1.15 |
| VITAMIN $B_6$, (mg) | 0.13 |
| VITAMIN $B_{12}$, (mcg) | 0.39 |
| BIOTIN, (mcg) | 18.75 |
| FOLIC ACID, (mcg) | 30 |
| PANTOTHENIC ACID, (mg) | 0.63 |
| VITAMIN K, (mcg) | 5 |
| CALCIUM, (mg) | 60.6 |
| COPPER, (mg) | 0.17 |
| IRON, (mg) | 0.95 |
| MAGNESIUM, (mg) | 15.45 |
| MANGANESE, (mg) | 0.28 |
| PHOSPHORUS, (mg) | 38.26 |
| ZINC, (mg) | 0.8 |
| IODINE, (mcg) | 8.63 |

Example 9

Bagel

A bagel, obtained from Brooklyn Bagel Boys, Inc. of Franklin Park, Ill., may be nutritionally enhanced according to the present invention by adding DFEA thereto. Table XVIII depicts the vitamin and mineral content of the fortified bagel, which contains about 5% of the daily DFEA in about an 82 gram serving.

TABLE XVIII

Bagel

| Nutrient | Fortification Level |
|---|---|
| VITAMIN A, (IU) | 450 |
| VITAMIN D, (IU) | 31 |
| VITAMIN E, (IU) | 2.25 |
| VITAMIN C, (mg) | 15 |
| VITAMIN $B_1$, (mg) | 0.09 |
| VITAMIN $B_2$, (mg) | 0.1 |
| VITAMIN $B_3$, (mg NE) | 1.15 |
| VITAMIN $B_6$, (mg) | 0.13 |
| VITAMIN $B_{12}$, (mcg) | 0.39 |
| BIOTIN, (mcg) | 18.75 |
| FOLIC ACID, (mcg) | 30 |
| PANTOTHENIC ACID, (mg) | 0.63 |

TABLE XVIII-continued

Bagel

| Nutrient | Fortification Level |
|---|---|
| CALCIUM, (mg) | 60.6 |
| COPPER, (mg) | 0.17 |
| IRON, (mg) | 0.95 |
| MAGNESIUM, (mg) | 15.45 |
| MANGANESE, (mg) | 0.28 |
| PHOSPHORUS, (mg) | 38.26 |
| ZINC, (mg) | 0.8 |
| IODINE, (mcg) | 8.63 |

Example 10

Meats

A nutritionally enhanced Salisbury Steak component according to the present invention is formulated as follows:

| Ingredient | Percentage (by weight) |
|---|---|
| Beef Boneless 95% | 65.2500 |
| Soy Protein Isolate | 5.3500 |
| Salt | 0.2402 |
| Water | 16.3793 |
| Potassium Chloride | 0.2402 |
| Onions ¼ IQF | 2.4000 |
| Garlic (Ground) | 0.2500 |
| Mixed Spices | 0.0451 |
| Blk Pepper Gr. | 0.0378 |
| Onion Flavor | 0.0976 |
| Breading | 1.8000 |
| Mixed Spices (fluid) | 0.0671 |
| Beef Flavor | 2.0000 |
| Flavor Additive | 0.0732 |
| Sodium Phosphate | 0.3305 |
| Potassium Lactate | 1.6695 |
| DFEA | 3.7195 |
| Flavor Enhancer | 0.0500 |
| | 100% |

To prepare the Salisbury Steak, boneless beef is selected which has been slaughtered within about 75 days, and preferably, within about 30 days, of the preparation date. The beef is tempered to a temperature in a range of about −4 to −2° C. (25 to 28° F.) within about 36 hours of use. Further, the beef at about −2° C. (28° F.) is refrigerated and used within 12 hours of reaching −2° C. (28° F.).

The beef is then ground through a 1.6 cm (⅝ inch) die and is placed in a mixer, such as a Mepaco or Ribbon mixer. Water (e., 147.3 kgs (324 lbs)), soy protein, and DFEA are added to the mixer, and these ingredients are mixed at about 45 RPMs for about 30 seconds or until the ingredients are uniformly mixed.

The beef flavor, potassium lactate, flavor enhancer, mixed spices (fluid), flavor additive, and IQF Onions are then added to the ingredients in the mixer. The beef and fried onion flavors are diluted with water (e., 17 kgs (37.5 lbs) water) before they are added to the mixer. In addition, a dry preblend including salt, potassium chloride, sodium phosphate, garlic powder, mixed spices, black pepper, and breading is added to the ingredients in the mixer. These ingredients may be added to the mixer in various orders. The diluted onion flavor, however, is preferably added last. After all ingredients have been added to the mixer, the ingredients are mixed at about 45 RPMs until uniformly mixed, e.g., for about one to three minutes.

Up to 5% of the total mix weight may be added in the form of previously cooked Salisbury Steak patties. Such patties are reground through a 1.6 cm (⅝ inch) die before addition to the mixer. If the storage temperature of such previous cooked patties is in a range of about 0 to 4.4° C. (32 to 40° F.), they may be reground and added to the mixer within not more than 14 hours. However, previously cooked patties stored at about −18° C. (0° F.) in sealed plastic bags may be used within about 30 days of storage.

The combination of ingredients from the mixture is then reground through a 0.32 cm (⅛ inch) die. Moreover, the die plate in this grinding is preferably equipped with a bone collection device.

The reground mix is then formed into patties with a length of about 13.7 cm (5.4 inches), a thickness of about 1.2 cm (0.47 inches), and a width of about 7.9 cm (3.1 inches). Each of such raw patties weighs about 85 grams (3.1 ounces). The patties are cooked to a minimum internal temperature of about 69.4° C. (157° F.) and until a uniform browned surface color is achieved. Each cooked patty weighs about 82 grams (3 ounces).

Table XIX depicts the vitamin and mineral content of the resulting fortified Salisbury Steak patty, which contains about 30% of daily DFEA in about a 82 gram (3 ounces) serving.

TABLE XIX

Salisbury Steak

| Nutrient | Fortification Level |
|---|---|
| VITAMIN A, (IU) | 2700 |
| VITAMIN D, (IU) | 186 |
| VITAMIN E, (IU) | 13.5 |
| VITAMIN C, (mg) | 90 |
| VITAMIN $B_1$, (mg) | 0.54 |
| VITAMIN $B_2$, (mg) | 0.61 |
| VITAMIN $B_3$, (mg NE) | 6.9 |
| VITAMIN $B_6$, (mg) | 0.75 |
| VITAMIN $B_{12}$, (mcg) | 2.34 |
| BIOTIN, (mcg) | 112.1 |
| FOLIC ACID, (mcg) | 180 |
| PANTOTHENIC ACID, (mg) | 3.75 |
| VITAMIN K, (mcg) | 30 |
| CALCIUM, (mg) | 363.6 |
| COPPER, (mg) | 0.99 |
| IRON, (mg) | 5.67 |
| MAGNESIUM, (mg) | 92.7 |
| MANGANESE, (mg) | 1.65 |
| PHOSPHORUS, (mg) | 229.54 |
| ZINC, (mg) | 4.82 |
| IODINE, (mcg) | 51.75 |

Example 11

Meat Sauces

A nutritionally enhanced Salisbury Steak Gravy component according to the present invention is formulated as follows:

| Ingredient | Percentage (by weight) |
|---|---|
| Burnt Sugar | 0.1709 |
| Yeast Extract | 0.5100 |
| Beef Base | 0.2900 |
| Salt | 0.0200 |
| Potassium Chloride | 0.0200 |
| Beef Flavor | 5.9001 |
| Wheat Flour | 2.2100 |
| Mixed Spices (fluid) | 0.0900 |
| Tomato Paste | 1.1200 |
| Potassium Lactate | 1.5600 |

-continued

| Ingredient | Percentage (by weight) |
|---|---|
| Garlic (Granular) | 0.1400 |
| Onion Pd. | 1.2300 |
| Flavor Enhancer | 0.0500 |
| DFEA | 0.7857 |
| Modified Food Starch | 1.9700 |
| Water Suspension | 15.1801 |
| Water Batch | 56.9387 |
| SUBTOTAL | 88.1999 |
| Sauce From Above | 88.2008 |
| Onions IQF ¼ | 1.9700 |
| Mushrooms | 9.8201 |
|  | 100.0000 |

To prepare the Salisbury Steak Gravy, the tomato paste is diluted with water and added to a steam-jacketed kettle. The diluted tomato paste is then mixed until homogenous. The beef base, beef flavor, and water (e. about 38 liters (10 gallons)) is then added to the kettle and heated to a boil to dissolve the powdered ingredients. Additional hot water is added to the kettle to increase the volume of the combination in the kettle to about 152 liters (40 gallons). Moreover, salt, yeast extract, burnt sugar, potassium chloride, garlic granules, mixed spices (fluid), potassium lactate, and the flavor enhancer are added to the combination in the kettle and stirred thoroughly until dissolved. The volume of the kettle contents is then readjusted with hot water to about 303 liters (80 gallons), and the kettle contents are steam heated to at least about 88° C. (190° F.).

A thickener slurry is prepared by combining the modified food starch, wheat flour, onion powder, and DFEA with water in a Norman Mixer and mixing the combination thoroughly. The mixer combination is then passed through a 20# mesh screen. Within about 30 minutes of the preparation of the slurry, the screened slurry is mixed into the kettle contents, and the kettle contents are further heated to about 91° C. (195° F.). A final adjustment is made to the kettle contents to raise their volume to about 379 liters (100 gallons). The kettle contents are then left to stand for about five minutes, after which the volume is readjusted to about 379 liters (100 gallons) and the mixture is stirred until uniform.

The kettle mixture is then cooled to at least about 21.1° C. (70° F.). The kettle contents are transferred to a crazy kettle or soup cart, and the mushrooms and IQF Onions are added to the combination of ingredients. Before adding the mushrooms, however, they must be cleaned and collected in a cooling insert and immersed in boiling water. Although the mushrooms are boiled for about five minutes, they are rinsed with cold water before addition to the ingredient combination. Thus, the final gravy temperature is about 18.3° C.±2.7° C. (65° F±5° F.). Preferably, the gravy is applied to the Salisbury Steak patty within about three hours of preparation.

Table XX depicts the vitamin and mineral content of the resulting fortified Salisbury Steak Gravy, which contains about 5% of daily DFEA in about a 55 gram (2 ounces) serving.

TABLE XX

Salisbury Steak Gravy

| Nutrient | Fortification Level |
|---|---|
| VITAMIN A, (IU) | 450 |
| VITAMIN D, (IU) | 31 |
| VITAMIN E, (IU) | 2.25 |
| VITAMIN C, (mg) | 15 |
| VITAMIN $B_1$, (mg) | 0.09 |
| VITAMIN $B_2$, (mg) | 0.1 |
| VITAMIN $B_3$, (mg NE) | 1.15 |
| VITAMIN $B_6$, (mg) | 0.13 |
| VITAMIN $B_{12}$, (mcg) | 0.39 |
| BIOTIN, (mcg) | 18.75 |
| FOLIC ACID, (mcg) | 30 |
| PANTOTHENIC ACID, (mg) | 0.63 |
| VITAMIN K, (mcg) | 5 |
| CALCIUM, (mg) | 60.6 |
| COPPER, (mg) | 0.17 |
| IRON, (mg) | 0.95 |
| MAGNESIUM, (mg) | 15.45 |
| MANGANESE, (mg) | 0.28 |
| PHOSPHORUS, (mg) | 38.26 |
| ZINC, (mg) | 0.8 |
| IODINE, (mcg) | 8.63 |

Example 12

Meals

This example demonstrates the preparation of prepackaged meals according to the present invention. Soup meals were prepared by retorting as described above and other meals were frozen. The nutritional characteristics of certain breakfast meals are shown in Table XXI, lunch meals are shown in Table XXII, dinner meals are shown in Table XXIII, and snack meats are shown in Table XXIV.

TABLE XXI (Breakfast Meals)

| Breakfast Group | ENGLISH MUFFIN SANDWICH | FRENCH TOAST AND SAUSAGE | PANCAKES AND SAUSAGE | SCRAMBLED EGGS |
|---|---|---|---|---|
| Serving Size g (oz). | 177 (6.25) | 191 (6.75) | 184 (6.50) | 206 (7.25) |
| Servings Per Container | 1 | 1 | 1 | 1 |
| AMOUNT PER SERVING | | | | |
| Calories | 320 | 340 | 360 | 360 |
| Calories From Fat | 54 | 54 | 63 | 63 |
| Total Fat (g) | 6 | 6 | 7 | 7 |
| Saturated Fat (g) | 2 | 1 | 2 | 2 |
| Polyunsaturated Fat (g) | 2 | 2 | 3 | 2 |
| Monounsaturated Fat (g) | 2 | 3 | 2 | 3 |
| Cholesterol (mg) | 45 | 70 | 50 | 50 |
| Sodium (mg) | 420 | 390 | 370 | 420 |
| Potassium (mg) | 630 | 750 | 810 | 660 |
| Total Carbohydrate (g) | 46 | 57 | 60 | 57 |
| Dietary Fiber (g) | 7 | 7 | 7 | 6 |
| Sugar (g) | 18 | 33 | 35 | 23 |
| Protein (g) | 21 | 14 | 16 | 13 |

TABLE XXI-continued (Breakfast Meals)

| Breakfast Group | ENGLISH MUFFIN SANDWICH | FRENCH TOAST AND SAUSAGE | PANCAKES AND SAUSAGE | SCRAMBLED EGGS |
|---|---|---|---|---|
| PERCENTAGE OF U.S. RECOMMENDED DIETARY ALLOWANCES (USRDA) | | | | |
| Vitamin A | 35 | 35 | 35 | 35 |
| Vitamin C | 55 | 55 | 55 | 55 |
| Calcium | 40 | 40 | 40 | 40 |
| Iron | 35 | 35 | 35 | 35 |
| Vitamin D | 35 | 35 | 35 | 35 |
| Vitamin E | 35 | 35 | 35 | 35 |
| Thiamine | 35 | 35 | 35 | 35 |
| Riboflavin | 35 | 35 | 35 | 35 |
| Niacin | 35 | 35 | 35 | 35 |
| Vitamin $B_6$ | 35 | 35 | 35 | 35 |
| Folic Acid | 35 | 35 | 35 | 35 |
| Vitamin $B_{12}$ | 35 | 35 | 35 | 35 |
| Phosphorus | 25 | 25 | 25 | 25 |
| Iodine | 35 | 35 | 35 | 35 |
| Magnesium | 25 | 25 | 25 | 25 |
| Zinc | 35 | 35 | 35 | 35 |
| Copper | 50 | 50 | 50 | 50 |
| Biotin | 35 | 35 | 35 | 35 |
| Pantothenic Acid | 35 | 35 | 35 | 35 |
| Vitamin K (mcg)* | 28 | 28 | 28 | 28 |
| Manganese (mg)* | 1.75 | 1.75 | 1.75 | 1.75 |

*No USRDA Established. NAS/NRC allowance used.

TABLE XXII (Lunch Meals)

| Lunch Group | SPLIT PEA SOUP | CHICKEN NOODLE SOUP | TURKEY SANDWICH | PASTA MEAL |
|---|---|---|---|---|
| Serving Size g (oz). | 369 (13.00) | 383 (13.5) | 291 (10.25) | 354 (12.5) |
| Servings Per Container | 1 | 1 | 1 | 1 |
| AMOUNT PER SERVING | | | | |
| Calories | 347 | 340 | 320 | 350 |
| Calories From Fat | 72 | 54 | 54 | 36 |
| Total Fat (g) | 8 | 6 | 6 | 4 |
| Saturated Fat (g) | 2 | 2 | 2 | 2 |
| Polyunsaturated Fat (g) | 3 | 3 | 1 | 1 |
| Monounsaturated Fat (g) | 3 | 1 | 3 | 1 |
| Cholesterol (mg) | 60 | 45 | 20 | 10 |
| Sodium (mg) | 670 | 580 | 450 | 420 |
| Potassium (mg) | 987 | 800 | 680 | 710 |
| Total Carbohydrate (g) | 49 | 44 | 46 | 59 |
| Dietary Fiber (g) | 8 | 7 | 5 | 7 |
| Sugar (g) | 9 | 11 | 15 | 11 |
| Protein (g) | 19 | 26 | 20 | 20 |
| PERCENTAGE OF U.S. RECOMMENDED DIETARY ALLOWANCES (USRDA) | | | | |
| Vitamin A | 30 | 30 | 30 | 30 |
| Vitamin C | 50 | 50 | 50 | 50 |
| Calcium | 35 | 35 | 35 | 35 |
| Iron | 30 | 30 | 30 | 30 |
| Vitamin D | 30 | 30 | 30 | 30 |
| Vitamin E | 30 | 30 | 30 | 30 |
| Thiamine | 30 | 30 | 30 | 30 |
| Riboflavin | 30 | 30 | 30 | 30 |
| Niacin | 30 | 30 | 30 | 30 |
| Vitamin $B_6$ | 30 | 30 | 30 | 30 |
| Folic Acid | 30 | 30 | 30 | 30 |
| Vitamin $B_{12}$ | 30 | 30 | 30 | 30 |
| Phosphorus | 20 | 20 | 20 | 20 |
| Iodine | 30 | 30 | 30 | 30 |
| Magnesium | 20 | 20 | 20 | 20 |
| Zinc | 30 | 30 | 30 | 30 |
| Copper | 45 | 45 | 45 | 45 |
| Biotin | 30 | 30 | 30 | 30 |
| Pantothenic Acid | 30 | 30 | 30 | 30 |
| Vitamin K (mcg)* | 24 | 24 | 24 | 24 |
| Manganese (mg)* | 1.5 | 1.5 | 1.5 | 1.5 |

*No USRDA Established. NAS/NRC allowance used.

TABLE XXIII (Dinner Meals)

| Dinner Group | BBQ CHICKEN | GRILLED MUSTARD CHICKEN | HERB ROASTED CHICKEN | MEATLOAF | POT ROAST |
|---|---|---|---|---|---|
| Serving Size g (oz). | 326 (11.50) | 326 (11.50) | 354 (12.50) | 461 (16.25) | 425 (15.00) |
| Servings Per Container | 1 | 1 | 1 | 1 | 1 |
| AMOUNT PER SERVING | | | | | |
| Calories | 360 | 350 | 460 | 430 | 460 |
| Calories From Fat | 54 | 63 | 90 | 99 | 90 |

TABLE XXIII-continued

|  |  |  |  |  |  |
|---|---|---|---|---|---|
| Total Fat (g) | 6 | 7 | 10 | 11 | 10 |
| Saturated Fat (g) | 2 | 2 | 3 | 5 | 3 |
| Polyunsaturated Fat (g) | 2 | 2 | 3 | 1 | 2 |
| Monounsaturated Fat (g) | 2 | 3 | 4 | 5 | 5 |
| Cholesterol (mg) | 40 | 50 | 70 | 30 | 100 |
| Sodium (mg) | 670 | 640 | 750 | 650 | 590 |
| Potassium (mg) | 1060 | 720 | 1130 | 1410 | 1090 |
| Total Carbohydrate (g) | 52 | 48 | 61 | 55 | 58 |
| Dietary Fiber (g) | 9 | 7 | 7 | 7 | 8 |
| Sugar (g) | 7 | 8 | 6 | 13 | 18 |
| Protein (g) | 26 | 24 | 31 | 27 | 33 |
| PERCENTAGE OF U.S. RECOMMENDED DIETARY ALLOWANCES (USRDA) | | | | | |
| Vitamin A | 35 | 35 | 35 | 35 | 35 |
| Vitamin C | 55 | 55 | 55 | 55 | 55 |
| Calcium | 40 | 40 | 40 | 40 | 40 |
| Iron | 35 | 35 | 35 | 35 | 35 |
| Vitamin D | 35 | 35 | 35 | 35 | 35 |
| Vitamin E | 35 | 35 | 35 | 35 | 35 |
| Thiamine | 35 | 35 | 35 | 35 | 35 |
| Riboflavin | 35 | 35 | 35 | 35 | 35 |
| Niacin | 35 | 35 | 35 | 35 | 35 |
| Vitamin $B_6$ | 35 | 35 | 35 | 35 | 35 |
| Folic Acid | 35 | 35 | 35 | 35 | 35 |
| Vitamin $B_{12}$ | 35 | 35 | 35 | 35 | 35 |
| Phosphorus | 25 | 25 | 25 | 25 | 25 |
| Iodine | 35 | 35 | 35 | 35 | 35 |
| Magnesium | 25 | 25 | 25 | 25 | 25 |
| Zinc | 35 | 35 | 35 | 35 | 35 |
| Copper | 50 | 50 | so | 50 | 50 |
| Biotin | 35 | 35 | 35 | 35 | 35 |
| Pantothenic Acid | 35 | 35 | 35 | 35 | 35 |
| Vitamin K (mcg)* | 28 | 28 | 28 | 28 | 28 |
| Manganese (mg)* | 1.75 | 1.75 | 1.75 | 1.75 | 1.75 |

| Dinner Group | SALISBURY STEAK | SIRLOIN BEEF TIPS | TURKEY TRADITIONAL | TURKEY GLAZED | BEEF STEW |
|---|---|---|---|---|---|
| Serving Size g (oz). | 461 (16.25) | 390 (13.75) | 440 (15.50) | 454 (16.00) | 376 (13.25) |
| Servings Per Container | 1 | 1 | 1 | 1 | 1 |
| AMOUNT PER SERVING | | | | | |
| Calories | 380 | 430 | 540 | 490 | 380 |
| Calories From Fat | 81 | 90 | 90 | 117 | 81 |
| Total Fat (g) | 9 | 10 | 10 | 13 | 9 |
| Saturated Fat (g) | 4 | 4 | 3 | 4 | 4 |
| Polyunsaturated Fat (g) | 1 | 2 | 3 | 5 | 3 |
| Monounsaturated Fat (g) | 4 | 4 | 4 | 4 | 2 |
| Cholesterol (mg) | 30 | 35 | 35 | 60 | 70 |
| Sodium (mg) | 910 | 850 | 950 | 670 | 530 |
| Potassium (mg) | 1430 | 870 | 1400 | 1390 | 700 |
| Total Carbohydrate (g) | 49 | 56 | 71 | 66 | 50 |
| Dietary Fiber (g) | 7 | 11 | 8 | 8 | 9 |
| Sugar (g) | 12 | 10 | 11 | 19 | 15 |
| Protein (g) | 27 | 28 | 32 | 29 | 25 |
| PERCENTAGE OF U.S. RECOMMENDED DIETARY ALLOWANCES (USRDA) | | | | | |
| Vitamin A | 35 | 35 | 35 | 35 | 35 |
| Vitamin C | 55 | 55 | 55 | 55 | 55 |
| Calcium | 40 | 40 | 40 | 40 | 40 |
| Iron | 35 | 35 | 35 | 35 | 35 |
| Vitamin D | 35 | 35 | 35 | 35 | 35 |
| Vitamin E | 35 | 35 | 35 | 35 | 35 |
| Thiamine | 35 | 35 | 35 | 35 | 35 |
| Riboflavin | 35 | 35 | 35 | 35 | 35 |
| Niacin | 35 | 35 | 35 | 35 | 35 |
| Vitamin $B_6$ | 35 | 35 | 35 | 35 | 35 |
| Folic Acid | 35 | 35 | 35 | 35 | 35 |
| Vitamin $B_{12}$ | 35 | 35 | 35 | 35 | 35 |
| Phosphorus | 25 | 25 | 25 | 25 | 25 |
| Iodine | 35 | 35 | 35 | 35 | 35 |
| Magnesium | 25 | 25 | 25 | 25 | 25 |
| Zinc | 35 | 35 | 35 | 35 | 35 |
| Copper | 50 | 50 | 50 | 50 | 50 |
| Biotin | 35 | 35 | 35 | 35 | 35 |
| Pantothenic Acid | 35 | 35 | 35 | 35 | 35 |

TABLE XXIII-continued

| | | | | | |
|---|---|---|---|---|---|
| Vitamin K (mcg)* | 28 | 28 | 28 | 28 | 28 |
| Manganese (mg)* | 1.75 | 1.75 | 1.75 | 1.75 | 1.75 |

*No USRDA Established. NAS/NRC allowance used.

TABLE XXIV (Snack Meals)

| Snack Meals | BAGEL | PRETZEL | YOGURT CHOCOLATE | YOGURT VANILLA |
|---|---|---|---|---|
| Serving Size g (oz). | 64 (2.25) | 64 (2.25) | 149 (6 Fluid Oz.) | 149 (6 Fluid Oz.) |
| Servings Per Container | 1 | 1 | 1 | 1 |
| AMOUNT PER SERVING | | | | |
| Calories | 190 | 170 | 200 | 190 |
| Calories From Fat | 27 | 18 | 18 | 18 |
| Total Fat (g) | 3 | 2 | 2 | 2 |
| Saturated Fat (g) | 1 | 1 | 1 | 1 |
| Polyunsaturated Fat (g) | 1 | 1 | 1 | 1 |
| Monounsaturated Fat (g) | 1 | 0 | 0 | 0 |
| Cholesterol (mg) | 0 | 0 | 15 | 15 |
| Sodium (mg) | 115 | 150 | 140 | 135 |
| Potassium (mg) | 180 | 60 | 420 | 310 |
| Total Carbohydrate (g) | 39 | 34 | 33 | 32 |
| Dietary Fiber (g) | 2 | 1 | 3 | 2 |
| Sugar (g) | 2 | 1 | 9 | 11 |
| Protein (g) | 6 | 5 | 11 | 10 |
| PERCENTAGE OF U.S. RECOMMENDED DIETARY ALLOWANCES (USRDA) | | | | |
| Vitamin A | 4 | 4 | 4 | 4 |
| Vitamin C | 4 | 4 | & | 4 |
| Calcium | 4 | 4 | 4 | 4 |
| Iron | 4 | 4 | 4 | 4 |
| Vitamin D | 4 | 4 | 4 | 4 |
| Vitamin E | 4 | 4 | 4 | 4 |
| Thiamine | 4 | 4 | 4 | 4 |
| Riboflavin | 4 | 4 | 4 | 4 |
| Niacin | 4 | 4 | 4 | 4 |
| Vitamin $B_6$ | 4 | 4 | 4 | 4 |
| Folic Acid | 4 | 4 | 4 | 4 |
| Vitamin $B_{12}$ | 4 | 4 | 4 | 4 |
| Phosphorus | 4 | 4 | 4 | 4 |
| Iodine | 4 | 4 | 4 | 4 |
| Magnesium | 4 | 4 | 4 | 4 |
| Zinc | 4 | 4 | 4 | 4 |
| Copper | 4 | 4 | 4 | 4 |
| Biotin | 4 | 4 | 4 | 4 |
| Pantothenic Acid | 4 | 4 | 4 | 4 |
| Vitamin K (mcg)* | — | — | — | — |
| Manganese (mg)* | — | — | — | — |

Example 13

Organoleptic Storage Program

This example demonstrates the results of organoleptic testing of a nutritionally enhanced frozen meal according to the present invention. The meal comprises a pasta component, a garlic roll component and a fruit compote component. The test is designed to evaluate the ability of the therapeutic meals and therapeutic meal products to maintain flavor, aroma, appearance, and the like, when stored for periods up to nine months under retail storage conditions, i.e., at about −18° C. (0° F.). Results are set out on Tables XXIII, XXIV, and XXV below. In addition, a terminology key containing definitions and reference points is included for each therapeutic meal component described in the tables.

Intensity Scale 0.0=none 1.0=threshold 2.5=very slight 5.0=slight 7.5=moderate 10.0 =moderate 12.0=moderate to extreme 15.0=extreme NR=not rated V=variable Intensities

TABLE XXIII

Garlic Roll

| Storage Time (−18° C. (0° F.)) | INITIAL (≦2 Weeks) | 1 MONTH | 3 MONTHS | 6 MONTHS | 9 MONTHS |
|---|---|---|---|---|---|
| APPEARANCE | | | | | |
| Yellow (inside) | 3 | 4 | 3.5 | 4 | 3.5 |
| Brown (outside) | 6 | 7 | 7 | 7 | 7 |
| AROMA | | | | | |
| Stale Freezer | 5 | 3 | 4 | 5.5V | 5 V |
| Yeasty/Wheaty | 4 | 4.5 | 4 | 4.5 | 4 |
| Sour | 3 | 3 | 2.5 | 3 | 3 |
| Vegetable | 2.5 | 3 | 3 | 4 | 3 |
| Sweet Aromatics | 3 | 1.5 | 2 | 2 | 3 |
| Garlic Aroma | NR | NR | 2 | 0 | 0 |
| FLAVOR | | | | | |
| Stale Freezer | 5 | 5 | 4 | 5 | 5.5V |
| Yeasty/Wheaty | 4 | 5 | 4 | 4.5 | 4 |
| Sour | 3 | 3 | 2.5 | 2.5 | 2.5 |
| Vegetable | 3 | 2.5 | 3 | 4 | 3.5 |
| Sweet | 2 | 2 | 2.5 | 2 | 2 |
| Astringent | 3 | 3 | 2 | 3 | 2 |
| Garlic Flavor | NR | NR | 2.5 | 0 | 0 |
| Bitter Aftertaste (30 sec.) | 2 | 2.5 | 2 | 2 | 2.5 |
| Chalky Aftertaste | 3 | 3.5 | 4 V | 4.5 | 3.5V |
| TEXTURE | | | | | |
| Chewiness | 5 | 6 | 5 | 5.5V | 5.5V |
| Dryness | 13 | 11 | 12 | 12 | 10.5 |

TABLE XXIV

Pasta With Meat Sauce

| Storage Time (−18° C. (0° F.)) | INITIAL (≦2 Weeks) | 1 MONTH | 3 MONTHS | 6 MONTHS | 9 MONTHS |
|---|---|---|---|---|---|
| APPEARANCE | | | | | |
| Proportion of Vegetable Meat Sauce to Pasta | 11 | 11 | 10 V | 9 V | 9 |
| Orange/Red (Orange → Red) | 6 | 7 | 7 | 7 | 7 |
| Amount of Herb Particles | 5 | 4 | 4.5 | 5.5 | 4.5 |
| AROMA | | | | | |
| Green Bell Pepper | 6 | 5 | 7 V | 6.5V | 7.5V |
| Black Pepper | 3 | 3 | 5 V | 5 | 5 V |
| Italian Herbs | 6 | 5 | 7 | 8 | 7.5V |
| Cooked Tomato | 2 | 5 | 3.5 | 4 | 5 |
| FLAVOR | | | | | |
| Green Bell Pepper | 6 | 6 | 4.5 | 5.5 | 6 |
| Black Pepper | 4 | 4.5 | 5 | 6 | 6 V |
| Italian Herbs | 5.5 | 6.5 | 7 | 7 | 6 V |
| Chemical Heat | 7 | 6 | 6.5 | 6.5 | 6.5V |
| Cooked Tomato | 3 | 6 | 4 | 5 | 6 V |
| Sweet | 2.5 | 2 | 3 | 2.5 | 2.5 |
| Sour | 3 | 2 | 3 | 3 | 2 |
| Salt | 3 | 3 | 3 | 3.5 | 3 |
| Chemical Heat Aftertaste (30 sec.) | NR | 7 | 5.5 | 8.5 | 6.5 |
| Chemical Heat Atertaste (1 min.) | 10 | 8 | 7 | 7.5 | 5.5 |
| TEXTURE | | | | | |
| First Bite: Firmness (Pasta) - First Bite | 5 | 4 | 4 | 4 | 4 |
| Chew Down: Chewiness (Whole Product) | 4 | 4 | 4.5V | 4.5 | 3.5 |

TABLE XXV

Fruit Compote

| Storage Time (−18° C. (0° F.)) | INITIAL ≦2 weeks | 1 MONTH | 3 MONTHS | 6 MONTHS | 9 MONTHS |
|---|---|---|---|---|---|
| APPEARANCE | | | | | |
| Pink/Purple Color | 7 | 8 | 7.5 | 7.5 | 7.5 |
| Sauce/Fruit Ratio | 10 | 9 | 9 | 8 | 8 |
| Red Specks | 7.5 | 8 | 6 | 7 | 7 |
| Red Residue on Spoon/Bowl | 11 | 10 | 7.5 | 8.5 | 10 |
| AROMA | | | | | |
| Fermented | 5 | 5 | 6 | 6.5 | 6 V |
| Sweet Aromatics | 4 | 5 | 4 | 5 | 5 |
| Fruity | 7 | 7 | 6 | 5.5 | 5 |
| FLAVOR | | | | | |
| Cooked Apple | 5 | 4 | 4 | 4 | 4 |
| Stale Freezer | 3.5 | 2.5 | 2 | 3 | 2.5 |
| Cooked Pear | 2.5 | 2.5V (0–5) | 3 V | 3.5 | 4.5 |
| Sour | 6 | 5 | 4.5 | 4.5V | 4 V |
| Sweet | 5 | 4 | 4 V | 4.5V | 4.5 |
| Bitter | NR | NR | 2.5 | 2 | 2 |
| TEXTURE | | | | | |
| Firmness (Molars) | 7 | 6.5 | 7 | 6 | 6 |
| Viscosity of Sauce | 3.5 | 4 | 4.5V | 4.5 | 4 |
| Chewiness | 6.5 | 5 | 6 | 5 | 5 |

PASTA WITH MEAT SAUCE GARLIC ROLL DEFINITIONS OF TERMS

APPEARANCE

| | |
|---|---|
| Yellow Color | Intensity of yellow color going from light to dark (3.0 = Ivory Chalk). Rate inside of roll. |
| Brown Color | Intensity of brown color going from light to dark (7.5 = Raw Sienna Crayola ® Crayon, 15.0 = Sepia Crayola ® Crayon). Rate outside of roll. |

AROMA/FLAVOR

| | |
|---|---|
| Stale Freezer | Characteristic aroma/flavor of an undefrosted freezer. |
| Yeasty/Wheaty | Bakery-like aromatics reminiscent of yeast leavened wheat bread. |
| Sour Aroma | Aroma common to products that taste sour. |
| Vegetable | Aroma/flavor reminiscent of vegetables in general. |
| Sweet Aromatics | Aromatics common to products that taste sweet such as caramel, honey, brown sugar, maple syrup, and butterscotch. |
| Sour Flavor | One of the four basic tastes, perceived primarily on the sides of the tongue; common to acids such as citric acid and acetic acid (vinegar). |
| Sweet | One of the four basic tastes, perceived primarily on the tip of the tongue; common to sucrose and other sugars. |
| Astringent | Puckering or mouthdrying sensation felt in the oral cavity caused by substances such as tannins (in tea) and alum (in pickles). |
| Bitter Aftertaste | One of the four basic tastes, perceived primarily at the back of the tongue; common to caffeine and quinine. Bitter aftertaste rated about 30 seconds after expectorating. |
| Chalky Aftertaste | The lingering sensation of fine particulate matter similar to chalk powder. |

PASTA WITH MEAT SAUCE
GARLIC ROLL DEFINITIONS OF TERMS

TEXTURE

| | |
|---|---|
| Chewiness | Degree to which sample takes a large number of chews until ready for swallowing (not chewy to extremely chewy). |
| Dryness | Lack of moisture in product when chewed and manipulated. |

PASTA WITH MEAT SAUCE
PASTA COMPARTMENT DEFINITIONS OF TERMS

APPEARANCE

| | |
|---|---|
| Orange/Red Color | Amount of color (hue) present in the sample. Rated orange to red. (7.5 = Burnt Orange Crayola ® Crayon). |
| Amount of Herb Particles | Amount of herb-like particles perceived in products. |

AROMA/FLAVOR

| | |
|---|---|
| Green Bell Pepper | Aroma/flavor associated with green bell peppers. |
| Black Pepper | Characteristic aroma/flavor of ground black pepper. Rated none to extreme. |
| Italian Herbs | Aromatics reminiscent of Italian herbs such as basil, oregano, rosemary, tarragon, and thyme. |
| Cooked Tomato | Aromatics reminiscent of cooked tomato as demonstrated by canned tomato paste. |
| Chemical Heat | Burning sensation in the mouth caused by spicy foods such as capsaicin (red pepper) and piperine (black pepper). Not related to the temperature of the food. Rated none to extreme. Chemical heat aftertaste is rated one minute after expectorating. |
| Sweet | One of the four basic tastes, perceived primarily on the tip of the tongue; common to sucrose and other sugars. Rated none to extreme. |
| Sour | One of the four basic tastes, perceived primarily on the sides of the tongue; common to acids such as citric acid and acetic acid (vinegar). |
| Salty | One of the four basic tastes; perceived primarily on the side of the tongue; common to sodium chloride (table salt). Rated none to extreme. |
| Proportion of Vegetable Meat Sauce to Pasta | Proportion of sauce to pasta. A sample with an equal amount would be rated a 7.5 [rated from 100% sauce (i.e., 0) to 100% pasta (i.e., 15)]. |

TEXTURE

| | |
|---|---|
| Firmness of Pasta | The force to attain a given deformation; force to bite through with molars (incisors) or compress against palate (tongue). Rated soft to firm. |
| Chewiness of Whole Product | Degree to which sample takes a large number of chews until ready for swallowing. Rated not chewy to extremely chewy. |

PASTA WITH MEAT SAUCE
FRUIT COMPOTE DEFINITIONS OF TERMS

APPEARANCE

| | |
|---|---|
| Pink/Purple Color | Amount of color (hue) present in the sample. Rated pink to purple. (7.0 = Salmon Crayola ® Crayon). |
| Sauce/Fruit Ratio | Proportion of sauce to fruit. A sample with an equal amount of both shall be rated in the middle. (100% sauce to 100% fruit). |
| Red Specks | Amount of red specks appearing in sauce. Rated none to extreme. |
| Red Residue on Spoon/Bowl | Amount of red streaking and bleeding of color left on spoon and bowl after tasting. |

PASTA WITH MEAT SAUCE
FRUIT COMPOTE DEFINITIONS OF TERMS

AROMA/FLAVOR

| | |
|---|---|
| Fermented | Aromatic associated with products that have been fermented (e.g., wine, beer, bread) perceived at high levels in bread when the yeast has been fermented almost completely. Also, a characteristic flavor of fruit that has undergone fermentation during storage. |
| Sweet Aromatics | Aromatics common to products that taste sweet such as caramel, honey, brown sugar, maple syrup, and butterscotch. |
| Fruity | Aromatics common to fruits in general. |
| Cooked Apple | Characteristic aroma/flavor of cooked or baked apples. |
| Stale Freezer | Characteristic aroma/flavor of an undefrosted freezer. |
| Cooked Pear | Characteristic aroma/flavor of cooked pear. |
| Sour | One of the four basic tastes, perceived primarily on the sides of the tongue; common to acids such as citric acid and acetic acid (vinegar). |
| Sweet | One of the four basic tastes, perceived primarily on the tip of the tongue; common to sucrose and other sugars. Rated none to extreme. |

TEXTURE

| | |
|---|---|
| Firmness | The force to attain a given deformation; force to bite through with molars. |
| Viscosity of Sauce | Force required to manipulate sample with tongue. Rated thin to thick or none to extreme. |
| Chewiness | Degree to which sample takes a large number of chews until ready for swallowing. Rated not chewy to extremely chewy). |

REFERENCES FOR PASTA WITH MEAT SAUCE ROLL COMPARTMENT

| APPEARANCE | SCALE VALUE | | |
|---|---|---|---|
| Yellow Brown Color | 3.0 | | Alpha Ivory Chalk |
| | 7.5 | | Raw Sienna Crayola ® Crayon |
| | 10.0 | | Sepia Crayola ® Crayon |

| AROMA/ FLAVOR | AROMA SCALE VALUE | FLAVOR SCALE VALUE | |
|---|---|---|---|
| Yeasty/Wheaty | 6.0 | 4.0 | Bridgeford ® bread dough, thawed |
| Sour | — | 2.0 | about 0.025% citric acid in purified water |
| Sweet | | 2.0 | about 2% sucrose in purified water |
| Astringent | | 3.5 | about 0.04% alum |
| Chalky aftertaste | | 4.0 | Raw potato |

TEXTURE

| | | |
|---|---|---|
| Chewiness | 4.0 | Hebrew National ® Frankfurter |
| Dryness | 15.0 | Nabisco ® Unsalted Tops Premium Crackers |

REFERENCES FOR PASTA WITH MEAT SAUCE PASTA COMPARTMENT

| APPEARANCE | SCALE VALUE | |
|---|---|---|
| Vegetable Meat Sauce/Pasta Ratio | 0.0 | about 100% Sauce |
| | 7.5 | about 50% Sauce, about 50% Pasta |
| | 15.0 | about 100% Pasta |
| Orange/Red Color | 7.5 | Burnt Orange Crayola ®Crayon |
| Amount of Herb Particles | 4.0 | about 0.05% CVC parsley granules in water |
| | 6.0 | about 0.10% CVC parsley granules in water |
| | 9.0 | about 0.15% CVC parsley granules in water |
| | 11.0 | about 0.20% CVC parsley granules in water |

| AROMA/ FLAVOR | AROMA SCALE VALUE | FLAVOR SCALE VALUE | |
|---|---|---|---|
| Green Bell Pepper | 9.0 | 6.0 | Green bell pepper, 1" pieces cooked in boiling water for about 5 minutes |
| Black Pepper | 6.0 | 8.0 | about 0.2% Schilling ® black pepper in purified water |
| Italian Herbs | 10.0 | 8.0 | about 0.2% Schilling ® basil in purified water |
| Chemical Heat | — | 15.0 | Ortega ® jalapeno peppers |
| Cooked tomato | 10.0 | 10.0 | Contadina ® tomato paste |
| Sweet | — | 2.0 | about 2% sucrose in purified water |
| Sour | — | 2.0 | about 0.025% citric acid in purified water |
| Salt | — | 2.0 | about 0.2% sodium chloride in purified water |

| TEXTURE | | |
|---|---|---|
| Firmness | 4.5 | Kraft ® Deluxe American Cheese |
| Chewiness | 4.0 | Hebrew National ® Frankfurter |

REFERENCES FOR PASTA WITH MEAT SAUCE FRUIT COMPOTE COMPARTMENT

| APPEARANCE | SCALE VALUE | |
|---|---|---|
| Pink/Purple Color | 7.0 | Salmon Crayola ® Crayon |
| Sauce/Fruit Ratio | 0.0 | about 100% Sauce |
| | 7.5 | about 50% Sauce, about 50% Fruit |
| | 15.0 | about 100% Fruit |

-continued

| AROMA/ FLAVOR | AROMA SCALE VALUE | FLAVOR SCALE VALUE | |
|---|---|---|---|
| Fermented | 7.5 | — | Budweiser ® Beer |
| Sweet Aromatics | 8.0 | 8.0 | Brown Sugar |
| Fruity | 7.0 | 7.0 | Del Monte ® fruit cocktail |
| Cooked Apple | 4.0 | 4.0 | Red Delicious, 1" pieces cooked about 5 minutes in boiling water |
| Cooked Pear | 6.0 | 6.0 | Del Monte ® canned pear |
| Sour | | 5.0 | about 0.04% citric acid in purified water |
| Sweet | | 5.0 | about 5% sucrose in purified water |

| TEXTURE | | |
|---|---|---|
| Firmness | 7.0 | Starr Queen ® Size Spanish Olives, pimento removed |
| Viscosity | 4.0 | Carnation ® evaporated milk |
| | 5.0 | Heavy cream |
| Chewiness | 6.0 | Brach's ® Perky's Fruit Bunch |

Example 14

Clinical Trials

A clinical trial was conducted of a diet system which provided daily recommended dietary levels for vitamins and minerals as specified by the NAS/NRC Recommended Daily Allowances and followed the dietary guidelines of the AHA for total fat, saturated fat, cholesterol, and sodium and the American Diabetes Association recommendations for reducing simple sugar intake.

The objectives of this clinical trial were to investigate the acceptability of following a diet prepared according to the invention (hereinafter "Prepared Diet") in adults with sub-optimally controlled GCMD, to determine the difference between the control and experimental groups on the outcome variables: body weight, blood pressure, fructosamine, plasma glucose and plasma lipid levels, insulin, hemoglobin (Hb) $A_{1c}$, acceptability and satisfaction with diet, compliance with prescribed diet, and quality of life. The trial was also to monitor the safety of the Prepared Diet by monitoring nutritional intake in plasma vitamins (Vitamin A and Vitamin D) and mineral (iron), and trace minerals levels.

The trial was designed to be a multi-center randomized, prospective study consisting of two periods: Period 1: a four week baseline of usual diet and Period 2: a ten week intervention period of an individually prescribed diet using a Prepared Diet (i.e., the experimental group) vs. self-selected foods (i.e., the control group). During the baseline period, patients followed their usual diets. During the intervention period, the experimental group commenced the Prepared Diet. The patient population consisted of about 560 male and female patients (about 80 to 160 per category), who have been advised by a physician to modify their dietary lifestyle as the first approach or in conjunction with other medical therapy in order to manage any one of the following four diagnostic categories: Category $C_1$: mild to moderate essential hypertension; Category $C_2$: hyperlipidemia; Category $C_3$: non-insulin treated diabetes mellitus; and Category $C_4$: two or all three of the above Categories $C_1$–$C_3$. All subjects were required to meet the following criteria:

1. Age between about 25 to 70 years of age;
2. Females subjects of child bearing potential must use an accepted method of birth control;
3. Body Mass Index ≦ about 42 kg/m²;
4. Able to comply with following the Prepared Diet for all meals during the intervention period; and
5. Able to sign informed consent and comply with all study procedures.

Additionally, the diagnostic category specific criteria were:

CATEGORY $C_1$—Mild to Moderate Essential Hypertension. Either:
1. a. On no antihypertensive medication and b. Average sitting diastolic blood pressures of about 90 to 105* mmHg and/or sitting systolic blood pressures about 140 to 180* mmHg;

*Any patient who exceeds any upper limits in any category was not enrolled into the study in that or any other category or 2. a. Stabilized on antihypertensive medication for at least one month prior to study entry and b. Suboptimally Controlled with diastolic about 85 to 100 mmHg or systolic about 135 to 180 mmHg essential hypertension.

CATEGORY $C_2$—Hyperlipidemia. Either:
1. a. On no lipid lowering agent and b. Total cholesterol of about 220 to 300 mg/dL, and/or triglycerides about 200 to 1000 mg/dL;

or 2. a. Stabilized on lipid lowering agents for at least one month prior to study entry and b. Suboptimally controlled with cholesterol about 200 to 260 mg/dL and/or triglycerides about 200 to 1000* mg/dL.

*Any patient who exceeds any upper limits in any category was not enrolled into the study in that or any other category.

CATEGORY $C_3$—Non-insulin Dependent Diabetes. Either:
1. a. On no hypoglycemic agent and b. Fasting plasma glucose level ≦ about 140* mg/dL and $HbA_{1c}$, ≦ about 200% of median for assay (≦ about 15.4);

or 2. a. Stabilized on oral hypoglycemic agents for at least one month prior to entry and b. Suboptimally controlled with $HbA_{1c}$, about 100 to 175% of median for assay (about 7.7 to 13.48).

CATEGORY $C_4$: Meet the criteria for two or all three of the above diagnostic categories.

Other exclusion criteria included:
1. Serious abnormality on physical, screening blood work or ECG;
2. Renal disease with serum creatinine greater than about 1. 8 mg/dL;
3. Myocardial infarction within about 6 months, angina pectoris, congestive heart failure, insulin treatment for diabetes or secondary forms of hypertension;
4. Any chronic life-threatening disease including: active malignancy, active inflammatory bowel disease, active immunological disorders;
5. Any patient who exceeds any upper limits in any category was enrolled into the study in that or any other category.
6. Any gastrointestinal disease that would interfere with the absorption and/or excretion of dietary products;
7. Any woman who is lactating, pregnant or intending to become pregnant during the course of study;
8. History of substance abuse within about the past 12 months; 9. Current alcohol abuse as defined by more than two "yes" answers to the CAGE questions;
10. Unwilling or unable to discontinue any vitamin or mineral supplement or both;
11. Impairment of intellectual or psychological functioning which would prevent understanding the consent form or having normal psycho-social function; and
12. Currently participating in another study.

All patients are encouraged to drink at least about six to eight glasses, i e., about 1421 to 1894 mL (48 to 64 ounces), of water per day. In addition, patients were allowed to consume non-caloric beverages at their own discretion including black coffee, tea, club soda, diet soda, unflavored seltzer water, or mineral water. Consumption of alcohol was discouraged. However, a maximum of two alcoholic beverages (e.g., about 355 mL (12 ounces) of beer, 148 mL (5 ounces) of wine, or 30 mL (1 ounce) of distilled spirits) per day was allowed for patients whose dietary intervention included greater than about 1500 calories and who wished to consume alcohol. Any alcohol consumption, however, was factored into the prescribed caloric levels for both the prepared and control diets.

If all initial screening criteria were met, patients entered the four week baseline period. Patients were instructed to follow their usual diet and to keep three day food records during the baseline period. All patients had biweekly evaluation visits, and patients whose medication for treatment of one of the disease categories changed or who failed to keep the required food records or failed to cooperate with all components of study, were excluded prior to randomization. If all study criteria were met at Week-2, patients were randomized to receive either the Prepared Diet or to self select foods for their prescribed diet. Patients were unaware to which group they had been assigned until Week 0.

After the baseline period, all patients were given an individually prescribed diet and then were randomized equally into the experimental group which received the Prepared Diet and the control group which self-selected foods. Randomization was done centrally with stratification for each of the diagnostic categories and clinical centers. All individually prescribed dietary intervention was designed for either moderate weight loss or weight maintenance depending on the patient's needs.

The appropriate caloric level for each patient was calculated using age, body weight, height, gender, and level of physical activity. Normal weight patients were prescribed a diet having an appropriate caloric level. If weight loss was needed or desired, the patient and a nutritionist together determined an appropriate weight loss goal to achieve over the 10-week intervention period. This level did not exceed about 0.91 kg. (2 lbs.) per week after the first two weeks for a total not to exceed 10.91 kgs. (24 lbs.) total over the intervention period. The prescribed caloric intake was not lower than about 1200 calories per day for any patient. Using the caloric level determined by the nutritionist according to known equations, and the agreed upon weight loss goal, the appropriate caloric level for weight loss may be determined.

The caloric level is calculated by entering patient specific data into the gender specific Harris-Benedict equation. First, the patient's sex, weight (W) (in kilograms), height (H) (in centimeters), and Age (A) (in years) are determined. The patient's activity level then is determined from the following scale.

| | | |
|---|---|---|
| Very light | 1.3 | (about 10 hours rest, about 14 hours of very light activity) |
| Light | 1.5 | (sedentary job, minimal leisure time activity) |
| Light–moderate | 1.625 | (sedentary job, about 2–3 hours regular leisure-time) activity/week) |

| | | |
|---|---|---|
| Moderate | 1.75 | (sedentary job, > about 3 hours regular leisure-time activity/week) |
| Strenuous | 2 | (light–moderate manual labor) |
| Very Strenuous | 2.3 | (heavy labor) |

The weight, age, height, and activity values are then entered into the following gender-correct equation:

Males:
$[66.5 + (13.8 \times W) + (5.0 \times H)] \times$ activity allowance

Females:
$[655.1 + (9.6 \times W) + (1.8 \times H) - (4.7 \times A)] \times$ activity allowance Patients randomized to the experimental group received the Prepared Diet. Foods provided in the Prepared Diet were formulated in accordance with dietary recommendations specified by the NAS/NRC Recommended Daily Allowances for vitamins and minerals and for protein, carbohydrates, and fiber. These recommendations included a dietary profile that provides less than about 30% of calories from fat, about 15 to 20% of calories from protein, and about 55 to 60% of calories from carbohydrate as well as control of simple sugars. In addition, the Prepared Diet satisfied the recommended dietary levels, including, those for macro- and micronutrients specified above, in quantities that were shown to be important for disease management. These recommended dietary levels include low levels of sodium and refined sugar, and adequate-to-high levels of dietary fiber, potassium, and calcium. Additionally, the dietary guidelines for the Prepared Diet had fat (about 20 to 30% of calories), saturated fat (about 7 to 10% of calories), cholesterol (less than about 300 mg), sodium (less than about 3000 mg), and simple sugars are controlled such that the diet includes less than about 96 grams.

Food intakes for normal weight patients on the Prepared Diet were based on about a 1500 calorie diet in which caloric intake may be increased through the addition of provided adjustors. For all subjects in the Prepared Diet group who consume up to about 2600 calories/day, the number of entree items remained constant, but the number of adjustors, e.g., bagels, pretzels, and low-fat yogurt, was varied according to caloric prescription. These adjustors consisted of about 170 to 200 calories per serving and were low-fat, i e., less than about 3 grams of fat per serving. Patients with high daily caloric needs were permitted to consume additional meals, as shown in FIG. 2.

Food intakes for patients on the Prepared Diet, who were also on a weight loss program, were based on a about 1200 calorie diet. Consumption of the daily entrees yielded an average daily intake of about 1135 calories. The addition of either about 100 calories of supplemental foods selected from the groups consisting of fruits, vegetables, or low or nonfat dairy products provided a total of about 1235 calories.

Patients randomized to the Prepared Diet group were provided with their breakfast, lunch, and dinner entrees and needed adjustors. Patients selected food varieties by specifying a menu selection before hand. These foods provided subjects with nearly all foods that they required to complete the intervention successfully. Supplemental foods were not provided, but included one serving of a low-fat dairy product, a one cup serving of fruit, and a one cup serving of vegetables to be consumed daily.

Patients randomized to the control intervention group followed the AHA and ADA recommendations. These recommendations included a diet consisting of about 20 to 30% of calories from fat, about 15 to 20% of calories from protein, and about 55 to 60% of calories from carbohydrate, as well as control of simple sugars. While patients on the control diet were instructed how to make appropriate food selections to achieve maximum compliance unlike the patients in the Prepared Diet group, these control group patients were not provided the actual foods to comply. The control group did not have the benefit of DFEA fortified foods.

Week 0 begins the ten week intervention period. At this time, all patients met with the nutritionist to receive instructions for an individually prescribed therapeutic diet. During their next study visit, patients met with the nutritionist for follow up and review of diet instructions. No counseling session occurred after Week 2. However, all patients were monitored every two weeks. At each visit, three day food records were collected and reviewed with the nutritionist, and the experimental group ordered their Prepared Diet items from the menu selection for the next two weeks. The Prepared Diet was provided by home delivery or picked-up by the patient at a predetermined site.

The statistical analyses compared the changes from baseline to the end of the treatment periods between the prepared diet and control diet for each of the primary, secondary, safety, and compliance endpoints using a repeated measure ANOVA model. Objectives of the statistical analysis were to determine (1) the effects of the Prepared Diet on selected medical endpoints and (2) the acceptability of following the Prepared Diet in patients with the medical disorders studied herein. The primary endpoints for the effect of this diet included: change in blood pressure, plasma glucose levels, plasma lipid levels, and quality of life. In addition, an analysis was done to determine the safety (e.g., to identify adverse effects) of this diet by assessing change in select vitamin levels, serum iron, and trace minerals. Compliance was assessed by evaluating food records, body weight, and urinary electrolyte excretion. To this end, the proportion of prescribed foods consumed correctly and dietary non-compliance (eating foods outside the prescribed diet) was measured. This rate was assessed weeldy for trends, with non-compliance of greater than about 80% deemed unacceptable. Study dropout rates were also compared between the groups.

The equality of randomization was tested between the treatment groups and among the centers; adjustments were made as appropriate. An intention to treat analysis was performed, including all individuals randomized regardless of compliance or withdrawal. Major sources of variation that may contribute to differences in response included: error in recalling diet, cultural, geographic and climatologic variation among the centers, activity level, seasonal effect, cigarette smoking, alcohol consumption, and prescribed medication.

Blood pressure were measured using a standard mercury sphygmomanometer according to the American Heart Association guidelines. After resting five minutes, two supine followed by two sitting blood pressure measurements were recorded.

Dietary records were collected throughout the study in order to accomplish distinct goals. The first goal was to characterize the usual diet of all subjects during the baseline phase. The second goal was to monitor food intake in order to assess the consumed diet against the prescribed diet. Three-day food records were recorded by patients and collected by the nutritionist beginning baseline Week-2. This resulted in two sets of three day food records recorded during the baseline period and five sets of three day food records during the intervention period. Patients recorded their intake on three non-consecutive days specified by the nutritionist, and were given appropriate forms at each clinical visit. During the study visit, patients were interviewed by the nutritionist for completeness of the food records. Any additions or deletions to the prescribed diet were documented in these records.

Food records then were analyzed using the NCC nutrient data base. Compliance was monitored primarily by subjective measures. These included completion of food records by the patient, nutritionist interviews for food intake, monitoring of menu selections by the intervention group, and attendance at regularly scheduled clinic visits. Objective measures of dietary compliance also were monitored by comparing actual and projected weight maintenance or loss, urinary electrolytes excretion, and analysis of food records.

Acceptability of Prepared Diets was measured, inter alia, by two questionnaires directed to the quality of the diet and satisfaction with the diet administered throughout the study. The questions assessed the quality of life and satisfaction with diet. In addition, the completed scores from the two questionnaires were compared between the control and treatment groups by two sample non-parametric or parametric methods as appropriate. Satisfaction with diet also was assessed by a Diet Satisfaction Scale that was developed to assess global and specific aspects of dietary satisfaction. Additionally, quality of life measurements were effected by a battery of tests. At present, there are no scales specifically designed to measure the impact of nutrition on quality of life. Therefore, a battery of tests consisting of established quality of life instruments along with three new scales that were specifically designed to assess the impact of nutritional interventions on quality of life were selected. This battery provides a broad profile of quality of life that is sensitive to dietary manipulations. The primary indices of quality of life are the Mental Health Index and the General Health Perceptions scale. These instruments were developed by the Rand Corporation for the Health Insurance Study and generally are considered among the best available instruments for measuring quality of life. Additional tests were administered which measure the effects of diet on daily activities, work activities, nutrition hassles, nutrition and social function, nutritional health, and nutrition and affect on diet-responsive conditions. Thus, at least eight quantitative quality of life measurements were obtained for each patient during the baseline and intervention periods.

The clinical trials demonstrated that the system of the invention succeeded in reducing blood pressure for hypertension, reducing serum cholesterol and other lipid levels for hyperlipidemics; reducing or maintaining plasma glucose levels for diabetics; providing positive nutritional balance, as measured by blood and urine analysis; and improving the patients' quality of life, as measured through the questionnaires described above. Results of the clinical trials revealed that over a ten week intervention period, the systems and methods described herein may achieve a reduction in systolic blood pressure of as much as about 7 mmHg and of diastolic blood pressure of as much as about 4 mmHg. Further, in hyperlipidemics, total serum cholesterol may be reduced by as much as about 15 mg/dL, and in particular, triglycerides may be reduced by as much as about 13 mg/dL and LDL may be reduced by as much as about 10 mg/dL. In addition, $HbA_{1c}$ in diabetics may be reduced by as much as about 2%.

Thus, at the conclusion of the clinical trials, it was determined that the therapeutic meals and individual therapeutic food products were well tolerated by the patients. No significant adverse reactions were observed in either the control or Prepared Diet group. In addition to the specific improvements in the quantifiable indicators of diet-responsive conditions discussed above, the clinical trials revealed improvements in the quality of life of patients' consuming therapeutic meals and therapeutic food products according to the dietary health management system of the present invention. Further, these improvements were significant even in comparison to the control diet.

Figure 3A:
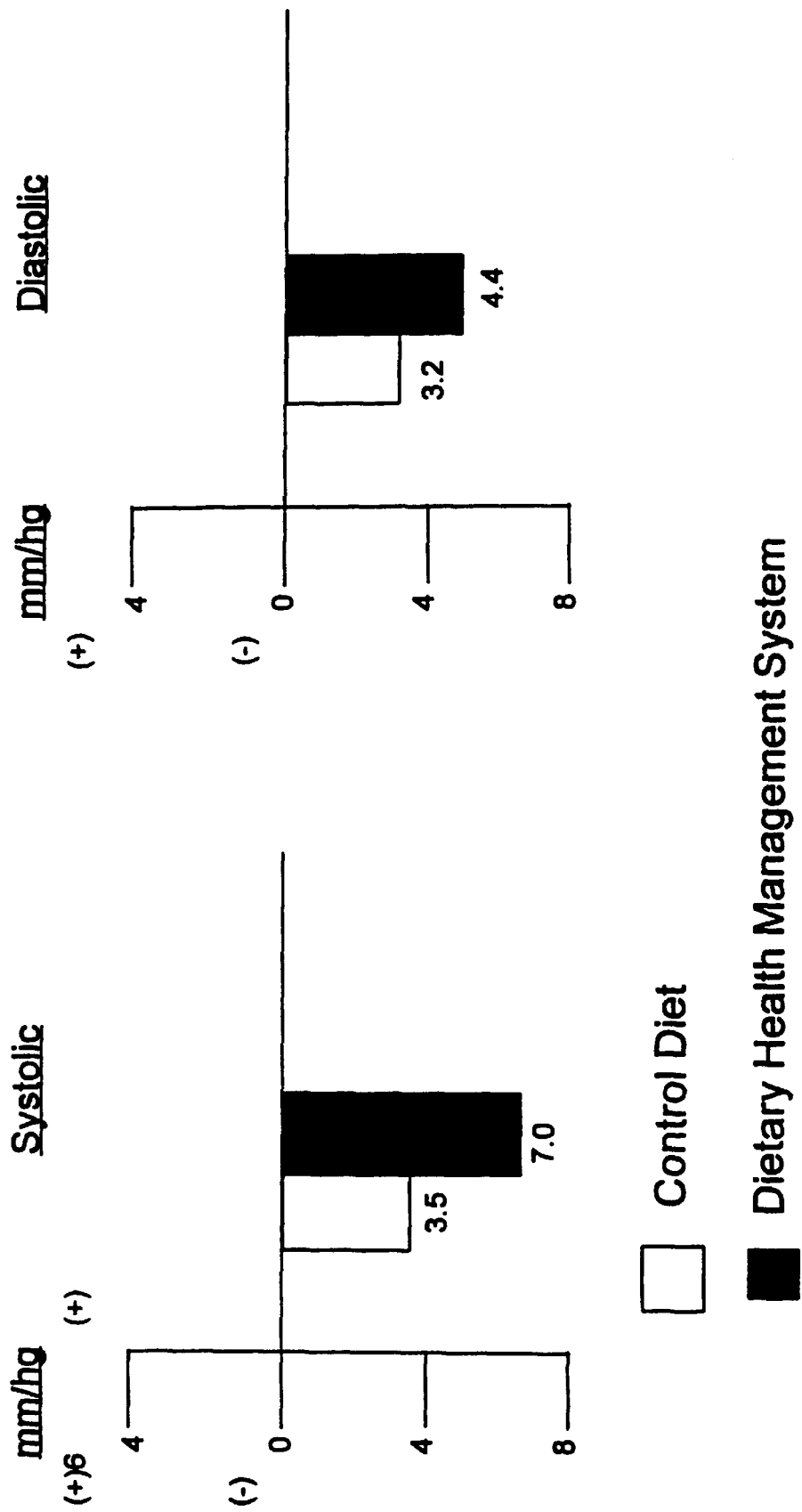
FIGS. 3a–c show charts depicting the reductions in systolic and diastolic blood pressure measurements and cholesterol, triglyceride, high-density lipoprotein (HDL), and low-density lipoprotein (LDL) levels for a patient with hypertension over a ten (10) week clinical trial period.
Figure 3B:
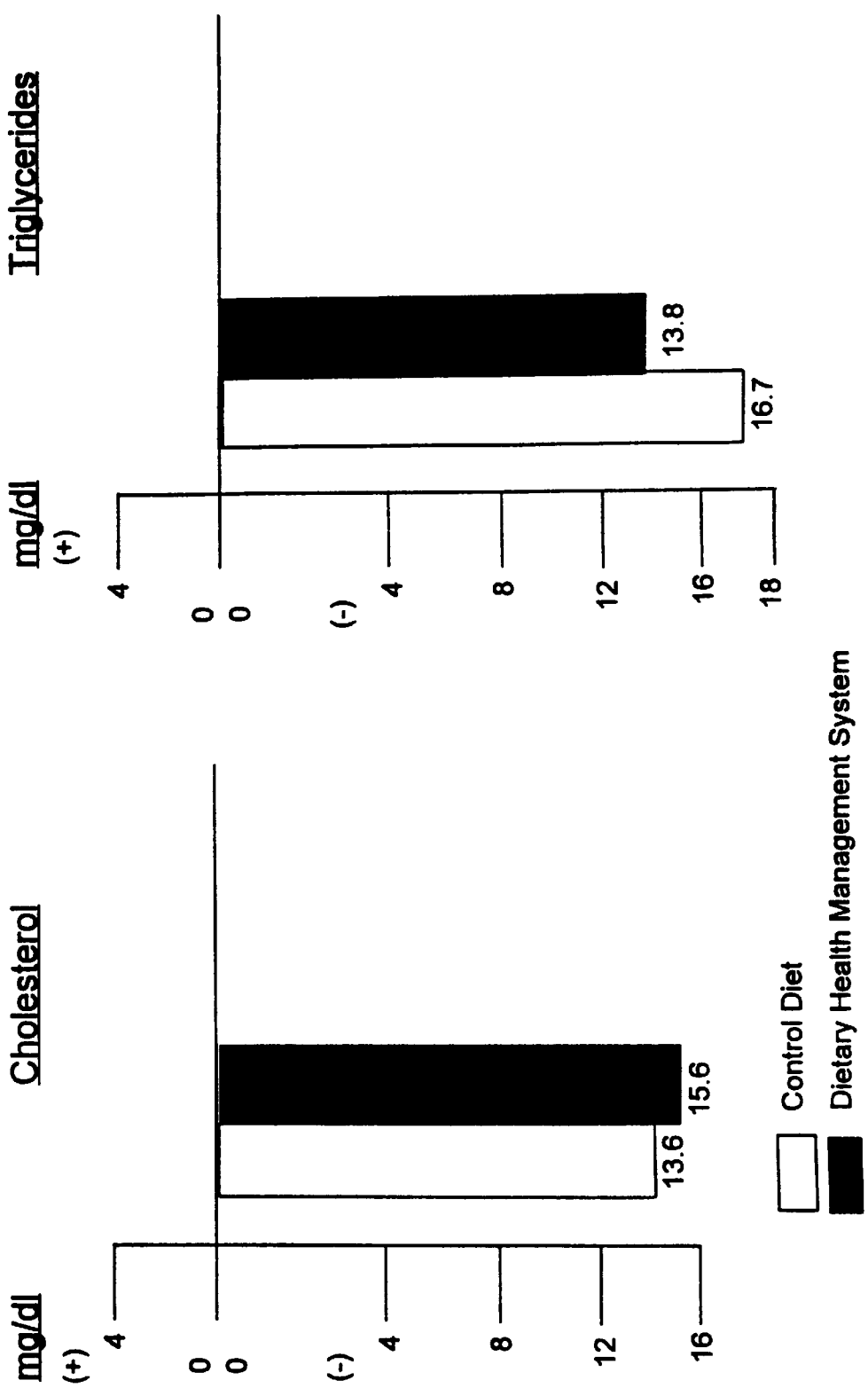
Figure 3C:
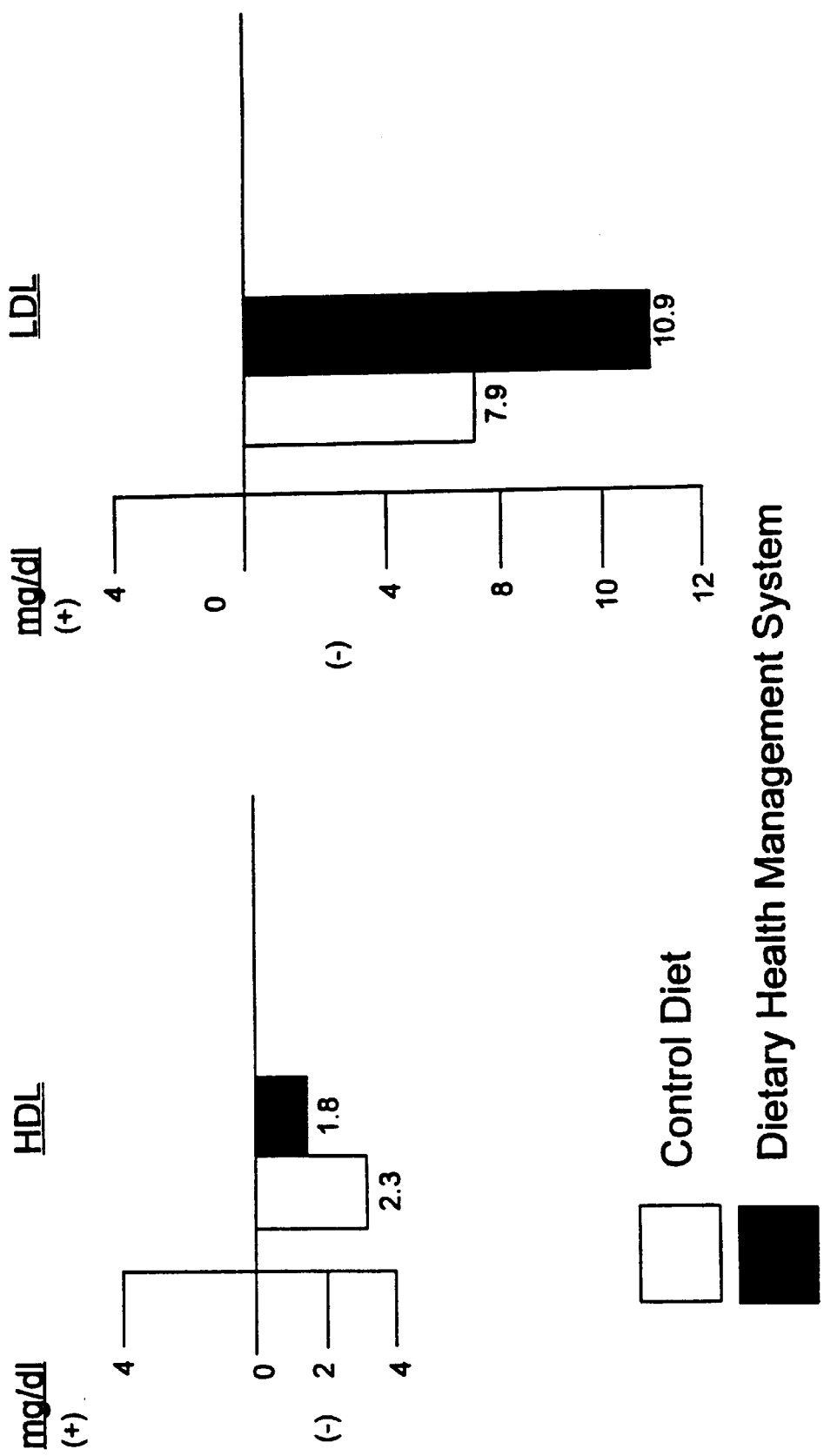

Referring to FIGS. 3a–c, the charts depict the results of the clinical trials with regard to the reduction of blood pressure and cholesterol levels for hypertensives. The charts compare the reduction in systolic and diastolic blood pressure (FIG. 3a), total serum cholesterol and triglycerides (FIG. 3b), and HDL and LDL (FIG. 3c) over a ten week intervention period for the systems and methods of the invention and the control diet. As these charts indicate, the system of the present invention (e.g, the Prepared Diet) achieved significantly greater reductions in the systolic and diastolic blood pressures of hypertensive patients than the control diet. However, the dietary health management system of the invention also reduced total serum cholesterol and LDL in the hypertension patients, e.g., Category $C_1$ or $C_4$, or both.

| DIET-RESPONSIVE CONDITION: HYPERTENSION | | |
|---|---|---|
| | REDUCTION (mmHg) | |
| TREATMENT | SYSTOLIC | DIASTOLIC |
| PREPARED DIET | 7.0 | 4.1 |
| CONTROL DIET | 3.7 | 3.2 |
| ACE INHIBITORS | 8 | 4 |
| BETA-BLOCKERS | 9 | 6 |
| CALCIUM CHANNEL BLOCKERS | 7 | 5 |
| DIURETIC | 11 | 5 |
| PERIPHERAL ANTI-ADVERERGIC AGENT | 5 | 4 |

In Table XXVIII, the reductions in systolic and diastolic blood pressure obtained with the systems and methods of the invention and those of the control diet over a ten week intervention period are compared to the reductions in systolic and diastolic blood pressure achieved through the use of antihypertensive agents over a twelve month treatment period. As may be seen from this table, the reductions obtained through the use of the dietary health management system are comparable to those achieved with several of the hypertensive agents. Nevertheless, the reductions were more rapidly achieved with the systems and methods of the present invention than with any of the identified antihypertensive agents.

Figure 4A:
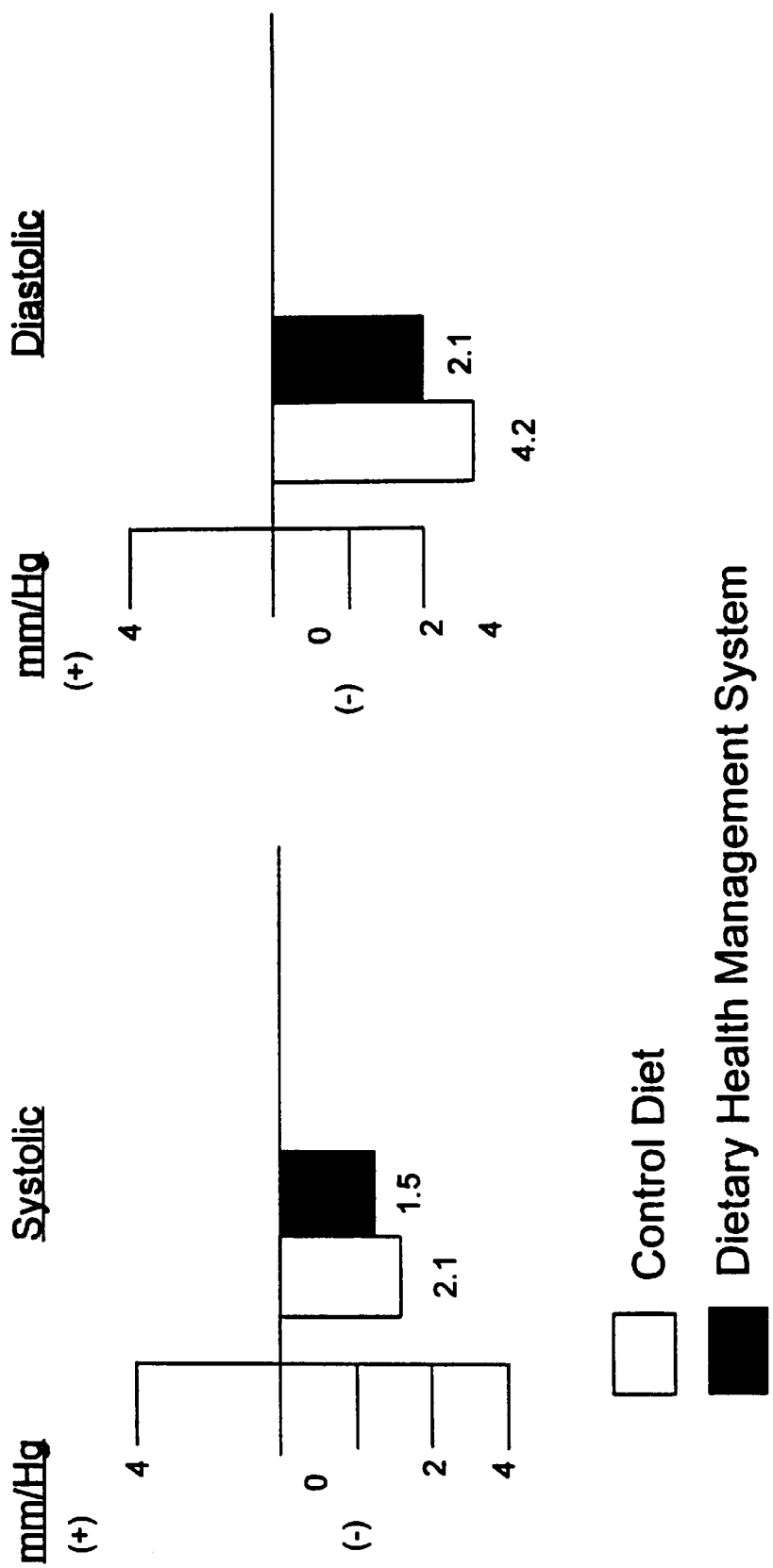
Figure 4B:
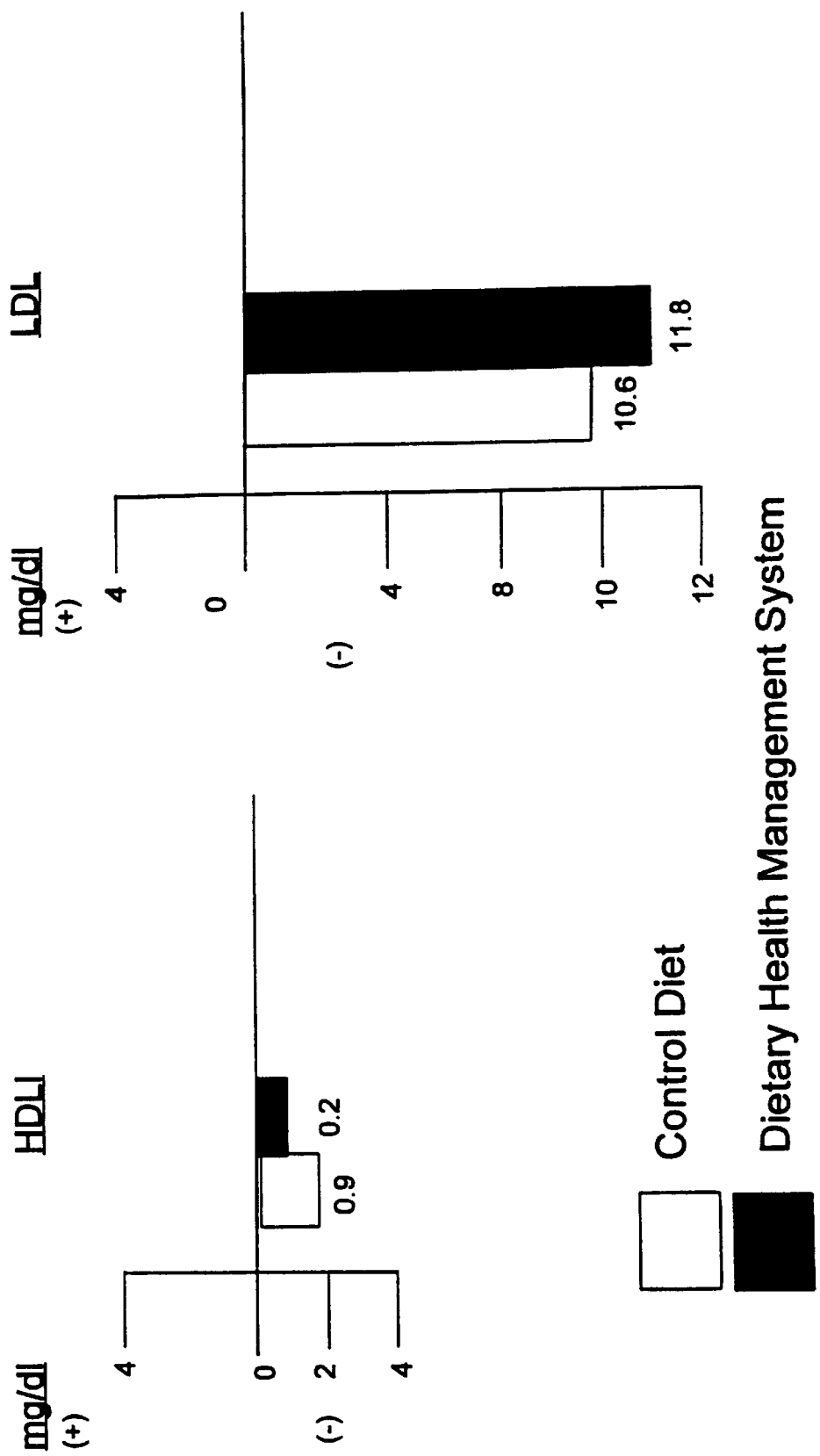

Referring to FIGS. 4a–c, the charts depict the results of the clinical trials with regard to the reduction of blood pressure and cholesterol levels for hyperlipidemics. The charts compare the reduction in systolic and diastolic blood pressure (FIG. 4a), total serum cholesterol and triglycerides (FIG. 4b), and HDL and LDL (FIG. 4c) over a ten week intervention period for the systems and methods of the invention and the control diet. As the charts of FIGS. 4b and 4c indicate, the dietary health management system of the invention achieved significantly greater reductions in total serum cholesterol, triglycerides, and LDL. When considered in combination with the reductions in the other lipid levels, the results achieved by the dietary health management system are clearly superior to those obtained with the control diet. Moreover, the system of the present invention also reduced systolic and diastolic blood pressure in the hyperlipidemia patients, e.g., Category $C_2$ or $C_4$, or both.

| DIET-RESPONSIVE CONDITION: HYPERLIPIDEMIA | | | |
|---|---|---|---|
| | REDUCTION (mg/dl) | | |
| TREATMENT | TRG | HDL | LDL |
| PREPARED DIET | 22 | 0.2 | 12 |
| CONTROL DIET | 14 | 0.9 | 11 |
| BILE ACID SEQUESTRANTS | 15–30 | (+)3–5 | — |
| NICOTINIC ACID | 10–25 | (+)15–35 | 20–50 |
| STATINS | 20–40 | (+)5–15 | 10–20 |
| FIBRIC ACID DERIVATIVES | 10–15 | (+)10–15 | 20–50 |

In Table XXIX, the reductions in serum cholesterol levels obtained with the systems and methods of the invention and those of the control diet over a ten week intervention period are compared to the reductions achieved through the use of anti-hyperlipidemic agents.

As discussed above, the systems and methods of the present invention may achieve reductions in $HbA_{1c}$ levels, as well as stabilization of or reduction in plasma glucose levels. During the clinical trials, $HbA_{1c}$ levels are reduced by amounts in a range of about 1 to 2%. Plasma glucose levels of diabetic patients using stabilizing medication experience stabilization or a trend toward reduction. Patients who control their diabetes without medication generally experience a trend toward the reduction of plasma glucose levels.

As discussed above, quality of life may be measured by various empirical tests. In the clinical trials, these measures included, but were not limited to, the Mental Health Index and the General Health Perception Scale. The Mental Health Index is measured by examining responses to questions designed to quantify the patient's anxiety, depression, loss behavior and positive affect of changed circumstances, and emotional ties. Similarly, General Health Perceptions Scale is measured by examining responses to questions designed to quantify the patients general health, vitality, and sleep disturbance. Additional tests were administered which measure the effects of diet on daily activities, work activities, nutrition hassles, nutrition and social function, nutritional health, and nutrition and affect on diet-responsive conditions. Thus, at least eight quantitative quality of life during the baseline and intervention periods. This enabled comparison of the results of the health management system and method to a patient's the baseline assessment and comparison of the results of the health management system and method to those of the AHA control diet during the intervention period.

The quality of life questionnaires revealed that a statistically significant change, i.e., $p<0.05$ level, was observed for each of the eight factors identified above. This statistically significant improvement in quality of life was observed between the group of patients administered a diet in accordance with the systems and methods of the invention and the control die, as well as between the group of patients administered a diet in accordance with the systems and methods and those patients' baseline assessment.

Other embodiments of the invention will be apparent to the skilled in the art from a consideration of the specification or practice of the invention disclosed herein. It is intended that the specification and examples be considered as exemplary only with the true scope and spirit of the invention being indicated by the following claims.

We claim:

1. A dietary health management system for administration to a patient having at least one diet-responsive condition comprising a meal program containing a plurality of pre-packaged individual meals for each day, each of said individual meals including a plurality of meal components and containing a predetermined level of nutritional enhancement, whereby consumption of a daily diet comprising a plurality of said individual meals supplies said patient with a desired total daily calorie content, wherein the percentage of calories provided in said daily diet by protein and fat, such that about 15 to about 20% of caloric intake derives from protein and such that about 20 to about 30% of caloric intake derives from fat; improved quality of life; and sufficient nutritional enhancement to improve the management of said diet-responsive condition, such that said nutritionally enhanced daily diet of meals includes an added source of dietary fiber providing dietary fiber in the range of about 20 to 30 grams, and a source vitamins and minerals, such that consumption of said daily diet provides vitamins and minerals of at least about 50% USRDA, sodium in an amount less than about 2400 mg; and potassium in a range of about 3000 mg to about 3500 mg; and includes simple sugars in an amount less than about 107 grams.

2. The dietary health management system of claim 1, wherein said diet-responsive condition is selected from the group consisting of obesity, hypertension, hyperlipidemia, cancer, diabetes, cardiovascular disease, and combinations thereof.

3. The dietary health management system of claim 2, wherein said cancer is selected from the group consisting of colo-rectal cancer, breast cancer, stomach cancer, and prostate cancer.

4. The dietary health management system of claim 1, wherein said desired total daily calorie content is in a range of about 1200 to 1500 calories.

5. The dietary health management system of claim 1, wherein said patient has a plurality of said diet-responsive conditions.

6. The dietary health management system of claim 1, wherein said patient has coronary heart disease.

7. The dietary health management system of claim 1, wherein at least one of said prepackaged, individual meals are frozen.

8. The dietary health management system of claim 1, wherein at least one of said prepackaged, individual meals are retorted or shelf-stable.

9. The dietary health management system of claim 1, wherein each of said nutritionally enhanced meals includes at least one meal component, said at least one meal component comprising a material selected from the group consisting of vitamins, minerals, and mixtures thereof, such that consumption of said daily diet includes vitamins and minerals in a range of about 75% to 100% USRDA.

10. The dietary health management system of claim 1, wherein said protein in said meal comprises an adjusted ratio between animal protein and vegetable protein.

11. The dietary health management system of claim 1, said nutritionally enhanced meals include simple sugars, such that consumption of said daily diet includes simple sugars in an amount less than about 96 grams.

12. The dietary health management system of claim 1, wherein each of said nutritionally enhanced meals includes saturated fat, such that consumption of said daily diet provides less than about 10% of caloric intake from saturated fat.

13. The dietary health management system of claim 1, wherein each of said nutritionally enhanced meals includes cholesterol, such that consumption of said daily diet provides less than about 300 mg of cholesterol.

14. The dietary health management system of claim 1, wherein each of said meals comprises a plurality of segregated meal components.

15. The dietary health management system of claim 14, wherein said meal components include at least one meat component.

16. The dietary health management system of claim 1, wherein said daily diet includes at least one of three supplemental foods selected from the group consisting of dairy products, fruits, and vegetables.

17. The dietary health management system of claim 1, wherein consumption of said daily diet of said meals provides vitamins and minerals at least about 100% USRDA.

18. The dietary health management system of claim 1, wherein said diet-responsive condition is obesity and said desired total daily calorie content is less than said patient's maintenance caloric level.

19. A dietary health management system for administration to a patient having at least one diet-responsive condition comprising a meal program containing a plurality of prepackaged individual meals for each day, each of said individual meals including a plurality of meal components and containing a predetermined level of nutritional enhancement, whereby consumption of a daily diet comprising a plurality of said individual meals supplies said patient with a desired total daily calorie content, wherein the percentage of calories provided in said daily diet by protein and fat, such that about 15 to about 20% of caloric intake derives from protein and such that about 20 to about 30% of caloric intake derives from fat; improved quality of life; and sufficient nutritional enhancement to improve the management of said diet-responsive condition, such that said nutritionally enhanced daily diet of meals includes an added source of dietary fiber providing dietary fiber in the range of about 20 to 30 grams, and a source vitamins and minerals, such that consumption of said daily diet provides vitamins and minerals of at least about 50% USRDA, sodium in an amount less than about 2400 mg; and potassium in a range of about 3150 mg to about 3850 mg; and includes simple sugars in an amount less than about 107 grams.

20. The dietary health management system of claim 19, wherein said daily diet includes about 3500 mg of potassium.

21. The dietary health management system of claim 19, wherein said diet-responsive condition is hypertension and said daily diet includes sodium in a range of about 2000 to 2400 mg.

22. The dietary health management system of claim 19, wherein said diet-responsive condition is hyperlipidemia and said daily diet includes cholesterol in a range of about 200 to 300 mg.

23. The dietary health management system of claim 22, wherein said fat comprises saturated fatty acid (SFA) in a range of about 7 to 10%, monounsaturated fatty acid (MUFA) in a range of about 10 to 13%, and polyunsaturated fatty acid (PUFA) of less than about 10%.

24. The dietary health management system of claim 19, wherein said fat comprises saturated fatty acid (SFA) in a range of about 7 to 10%, monounsaturated fatty acid (MUFA) in a range of about 10 to 13%, and polyunsaturated fatty acid (PUFA) of less than about 10%.

25. The dietary health management system of claim 19, wherein said diet-responsive condition is diabetes and said daily diet includes less than about 96 grams of simple sugars.

26. The dietary health management system of claim 25, wherein said fat comprises saturated fatty acid (SFA) in a range of about 7 to 10%, monounsaturated fatty acid (MUFA) in a range of about 10 to 13%, and polyunsaturated fatty acid (PUFA) of less than about 10%.

27. A dietary health management planning and control system for providing nutritionally enhanced dietary management to a patient having at least one diet-responsive condition comprising:
a plurality of prepackaged individual meals for each day wherein each of said meals is included within a group and has a group identifying code corresponding to the type of meal and wherein each of said meals further includes at least one category identifying code corresponding to a particular diet-responsive condition;
each of said individual meals includes a plurality of meal components and contains a predetermined level of nutritional enhancement, whereby consumption of a daily diet comprising a plurality of said individual meals supplies said patient with a desired total daily calorie content, wherein the percentage of calories provided in said daily diet by protein and fat, such that about 15 to about 20% of caloric intake derives from protein and such that about 20 to about 30% of caloric intake derives from fat; improved quality of life; and sufficient nutritional enhancement to improve the management of said diet-responsive condition, such that said nutritionally enhanced daily diet of meals includes an added source of dietary fiber providing dietary fiber in the range of about 20 to 30 grams, and a source vitamins and minerals, such that consumption of said daily diet provides vitamins and minerals of at least about 50% USRDA, sodium in an amount less than about 2400 mg; and potassium in a range of about 3000 mg to about 3500 mg; and includes simple sugars in an amount less than about 107 grams.

28. The planning and control system of claim 27, wherein said type of meal comprises breakfast, lunch, dinner, and snack.

29. The planning and control system of claim 27, wherein said group identifying code is selected from the group consisting of alphabetic indicia, numeric indicia, color indicia, graphic indicia, and combinations thereof.

30. The planning and control system of claim 27, wherein said category identifying code is selected from the group consisting of alphabetic indicia, numeric indicia, color indicia, graphic indicia, and combinations thereof.

31. The planning and control system of claim 27, wherein said diet-responsive condition is selected from the group consisting of obesity, hypertension, hyperlipidemia, cancer, diabetes, cardiovascular disease, and combinations thereof.

32. The planning and control system of claim 31, wherein said cancer is selected from the group consisting of colorectal, breast, stomach, and prostate cancer.

33. The planning and control system of claim 27, wherein said desired total daily calorie content is in a range of about 1200 to 1500 calories.

34. The planning and control system of claim 27, wherein said patient has a plurality of said diet-responsive conditions.

35. The planning and control system of claim 27, wherein at least one of said prepackaged, individual meals are frozen.

36. The planning and control system of claim 27, wherein at least one of said prepackaged, individual meals are retorted or shelf-stable.

37. The planning and control system of claim 27, wherein said daily diet includes three supplemental foods selected from the group containing of dairy products, fruits, and vegetables.

38. The planning and control system of claim 27, wherein each of said nutritionally enhanced meals includes at least one meal component, said at least one meal component comprising a material selected from the group consisting of vitamins, minerals, and mixtures thereof, such that consumption of said daily diet includes vitamins and minerals in a range of about 75% to 100% USRDA.

39. The planning and control system of claim 27, wherein said protein in said meal comprises an adjusted ratio between animal protein and vegetable protein.

40. The planning and control system of claim 27, said nutritionally enhanced meals include simple sugars, such that consumption of said daily diet includes simple sugars in an amount less than about 96 grams.

41. The planning and control system of claim 27, wherein each of said nutritionally enhanced meals includes saturated fat, such that consumption of said daily diet provides less than about 10% of caloric intake from saturated fat.

42. The planning and control system of claim 27, wherein each of said nutritionally enhanced meals includes cholesterol, such that consumption of said daily diet provides less than about 300 mg of cholesterol.

43. The planning and control system of claim 27, wherein each of said meals comprises a plurality of segregated meal components.

44. The planning and control system of claim 27, wherein said meal components include at least one meat component.

45. The planning and control system of claim 27, wherein a full day of meals provide vitamins and minerals at about 100% USRDA.

46. The planning and control system of claim 27, wherein said diet-responsive condition is obesity and said desired total daily caloric content is less than said patient's maintenance caloric level.

47. The planning and control system of claim 27, wherein said diet-responsive condition is hypertension and said daily diet includes sodium in a range of about 2000 to 2400 mg.

48. The planning and control system of claim 27, wherein said diet-responsive condition is hyperlipidemia and said daily diet includes cholesterol in range of about 200 to 300.

49. The planning and control system of claim 48, wherein said fat comprises saturated fatty acid (SFA) in a range of about 7 to 10%, monounsaturated fatty acid (MU FA) in a range of about 10 to 13%, and polyunsaturated fatty acid (PUFA) of less than about 10%.

50. The planning and control system of claim 27, wherein said diet-responsive condition is colo-rectal cancer and wherein said fat comprises saturated fatty acid (SFA) in a range of about 7 to 10%, monounsaturated fatty acid (MUFA)in a range of about 10 to 13%, and polyunsaturated fatty acid (PUFA) of less than about 10%.

51. The planning and control system of claim 27, wherein said diet-responsive condition is diabetes and said daily diet includes less than about 96 grams of simple sugars and wherein less than 30% of daily calories are derived from fat.

52. The planning and control system of claim 51, wherein said fat comprises saturated fatty acid (SFA) in a range of about 7 to 10%, monounsaturated fatty acid (MUFA) is a range of about 10 to 13%, and polyunsaturated fatty acid (PUFA) of less than about 10%.

* * * * *